United States Patent
Pevarello et al.

(10) Patent No.: US 7,037,929 B1
(45) Date of Patent: *May 2, 2006

(54) 2-AMINO-THIAZOLE DERIVATIVES, PROCESS FOR THEIR PREPARATION, AND THEIR USE AS ANTITUMOR AGENTS

(75) Inventors: Paolo Pevarello, Pavia (IT); Raffaella Amici, Piacenza (IT); Gabriella Traquandi, Milan (IT); Manuela Villa, Lurago d'Erba (IT); Anna Vulpetti, Brugherio (IT); Antonella Isacchi, Milan (IT)

(73) Assignee: Pharmacia & Upjohn S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/807,962

(22) PCT Filed: Oct. 27, 1999

(86) PCT No.: PCT/EP99/08306

§ 371 (c)(1),
(2), (4) Date: Apr. 26, 2001

(87) PCT Pub. No.: WO00/26202

PCT Pub. Date: May 11, 2000

(30) Foreign Application Priority Data

Oct. 30, 1998 (GB) .................................. 9823871

(51) Int. Cl.
*A61K 31/426* (2006.01)
*A61K 31/495* (2006.01)
*C07D 277/20* (2006.01)
*C07D 413/02* (2006.01)
*C07D 417/02* (2006.01)

(52) U.S. Cl. ...................... 514/371; 544/133; 544/238; 548/195; 514/235.5; 514/252.1

(58) Field of Classification Search ................ 548/195; 514/371, 252.1, 235.5; 544/133, 238
See application file for complete search history.

(56) References Cited

U.S. PATENT DOCUMENTS 3,374,082 A 3/1968 Lemin
3,427,318 A 2/1969 Barber et al.
3,591,600 A 7/1971 Fancher
4,027,031 A 5/1977 DeBaun et al.
6,407,124 B1 * 6/2002 Rawlins ...................... 514/342

FOREIGN PATENT DOCUMENTS

| DE | 2 128 941 | 12/1971 |
| DE | 1 642 352 | 2/1972 |
| EP | 0 261 503 | 3/1988 |
| EP | 0 412 404 | 2/1991 |
| FR | 1 488 625 | 6/1967 |
| FR | 1 499 557 | 9/1967 |
| WO | WO 98/04536 | 2/1998 |
| WO | WO 99/65884 | 12/1999 |

OTHER PUBLICATIONS

S.R.M. Bushby, et al., Chemical Abstracts, vol. 50, No. 1, p. 964, "The Antitrichomonal Activity of Amidonitrothiazoles", Jan. 10, 1956.

M. Robba, et al., Chemical Abstracts, vol. 61, No. 3, p. 3086, "Synthesis of Thiazoles and Isothiazoles. Their Action on *Tri-Chomonas vaginalis* and *Candida albicans*", Aug. 3, 1964.

(Continued)

*Primary Examiner*—Golam M. M. Shameem
(74) *Attorney, Agent, or Firm*—Scully, Scott, Murphy & Presser

(57) ABSTRACT

Compounds which are 2-amino-1,3-thiazole derivatives of formula (I)

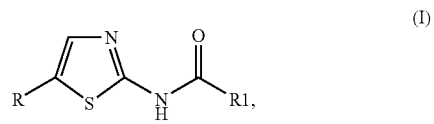

wherein R is a halogen atom, a nitro group, an optionally substituted amino group or it is a group, optionally further substituted, selected from i) straight or branched $C_1$–$C_8$ alkyl, $C_2$–$C_6$ alkenyl or $C_2$–$C_6$ alkynyl; ii) $C_3$–$C_6$ cycloalkyl; iii) aryl or arylalkyl with from 1 to 8 carbon atoms within the straight or branched alkyl chain; $R_1$ is an optionally further substituted group selected from: i) straight or branched $C_1$–$C_8$ alkyl or $C_2$–$C_6$ alkenyl; ii) 3 to 6 membered carbocycle or 5 to 7 membered heterocycle ring; iii) aryl or arylcarbonyl; iv) arylalkyl with from 1 to 8 carbon atoms within the straight or branched alkyl chain; v) arylalkenyl with from 2 to 6 carbon atoms within the straight or branched alkenyl chain; vi) an optionally protected amino acid residue; or a pharmaceutically acceptable salt thereof; are useful for treating cell proliferative disorders associated with an altered cell dependent kinase activity.

13 Claims, No Drawings

OTHER PUBLICATIONS

Peter J. Islip, et al., Journal of Medicinal Chemistry, vol. 15, No. 9, pp. 951-954, "Schistosomicidal 5-Nitro-4-Thiazolines", 1972.

Roger D. Westland, et al., Journal of Medicinal Chemistry, vol. 14, No. 10, pp. 916-920, "Novel Schistosomicides. S-2-{[2-(2-Thiazolylcarbamoyl)Ethyl)]Amino}Ethyl Hydrogen Thiosulfate and Related Compounds", 1971.

Leif Grehn, Journal of Heterocyclic Chemistry, vol. 14, No. 5, pp. 917-919, "A Method for Nitration of Thiazoles", Aug. 1977.

H. Erlenmeyer, et al., Helvetica Chimica Acta., vol. 28, pp. 985-991, "Zur Kenntnis Der Thiazol-4-Sulfonsaeure Und Der Thiazol-5-Sulfonsaeure", Jun. 29, 1945.

Charles D. Hurd, et al., Journal of the American Chemical Society, vol. 71, pp. 4007-4010, "The 2-Aminothiazoles", Dec. 1949.

Timothy N. Birkinshaw, et al., Journal of the Chemical Society, pp. 939-943, "Tautomerism in 2-Trichloro-and 2-Trifluoro-Acetamidothiazoles", 1982.

Chemical Abstracts, vol. 81, No. 5, p. 156, Aug. 5, 1974, JP 48-027467, Aug. 22, 1973.

* cited by examiner

2-AMINO-THIAZOLE DERIVATIVES, PROCESS FOR THEIR PREPARATION, AND THEIR USE AS ANTITUMOR AGENTS

The present invention relates to 2-amino-thiazole derivatives, to a process for their preparation, to pharmaceutical compositions containing them and to their use as therapeutic agents, particularly in the treatment of cancer and cell proliferative disorders.

Several cytotoxic drugs such as, e.g. fluorouracil (5-FU) doxorubicin and camptothecins result to damage DNA or to affect cellular metabolic pathways and thus cause, in many cases, an indirect block of the cell cycle. Therefore, by producing an irreversible damage to both normal and tumor cells, these agents result in a significant toxicity and side-effects. In this respect, compounds capable of being highly specific antitumor agents by selectively leading to tumor cell arrest and apoptosis, with comparable efficacy but reduced toxicity than the currently available drugs, are desirable.

It is well known in the art that progression through the cell cycle is governed by a series of checkpoint controls, otherwise referred to as restriction points, which are regulated by a family of enzymes known as the cyclindependent kinases (cdk). In their turn, the cdks themselves are regulated at many levels such as, for instance, binding to cyclins. A normal progression through the cell cycle is controlled by the coordinated activation and inactivation of different cyclin/cdk complexes. In G1, both cyclin D/cdk4 and cyclin E/cdk2 are thought to mediate the onset of S-phase. Progression through S-phase requires the activity of cyclin A/cdk2 whereas the activation of cyclin A/cdc2 (cdk1) and cyclin B/cdc2 are required for the onset of metaphases.

For a general reference to cyclins and cyclin-dependent kinases see, for instance, Kevin R. Webster et al. in Exp. Opin. Invest. Drugs, 1998, Vol. 7(6), 865–887.

Checkpoint controls are defective in tumor cells due, in part, to disregulation of cdk activity. For example, altered expression of cyclin E and cdk's has been observed in tumor cells, and deletion of the cdk inhibitor p27 KIP gene in mice has been shown to result in a higher incidence of cancer. Increasing evidence supports the idea that the cdks are rate-limiting enzymes in cell cycle progression and, as such, represent molecular targets for therapeutic intervention. In particular, the direct inhibition of cdk/cyclin kinase activity should be helpful in restricting the unregulated proliferation of a tumor cell.

It has now been found that the 2-amino-1,3-thiazoles of the invention are endowed with cdk/cyclin kinase inhibitory activity and are thus useful in therapy as antitumor agents whilst lacking, in terms of both toxicity and side effects, the aforementioned drawbacks known for currently available antitumor drugs. More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma.

Due to the key role of cdks in the regulation of cellular proliferation, these 2-amino-1,3-thiazole derivatives are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis, glomerulonephritis and post-surgical stenosis and restenosis. The compounds of the invention can be useful in the treatment of Alzheimer's disease, as suggested by the fact that cdk5 is involved in the phosphorylation of tau protein (*J. Biochem.*, 117, 741–749, 1995). The compounds of this invention, as modulators of apoptosis, could be useful in the treatment of cancer, viral infections, prevention of AIDS development in HIV-infected individuals, autoimmune diseases and neurodegenerative disorder. The compounds of this invention could be useful in inhibiting tumor angiogenesis and metastasis.

The compounds of this invention may also act as inhibitors of other protein kinases, e.g. protein kinase C, her2, raf1, MEK1, MAP kinase, EGF receptor, PDGF receptor, IGF receptor, PI3 kinase, wee1 kinase, Src, Abl and thus be effective in the treatment of diseases associated with other protein kinases.

Several 2-amino-1,3-thiazole derivatives are known in the art. Just few examples among them are 2-acetamido-, 2-propionamido- or 2-butyramido-1,3-thiazole derivatives further substituted by halogen atoms in position 5 of the thiazole ring, which are reported as herbicides in JP 73027467 (Sankyo Co. Ltd.) or U.S. Pat. No. 3,374,082 (The Upjohn Co.); 5-nitro-2-benzamido-1,3-thiazole is reported as pesticide in Ann. Rech. Vet., 22(4), 359–63, 1991; 5-phenyl-2-acetamido-1,3-thiazoles further substituted onto phenyl ring are reported as synthetic intermediates (Chemical Abstracts, 1980, 92:128793); and 5-dimethylaminomethyl- or 5-diethylaminomethyl-2-acetamido-1,3-thiazole, both reported as herbicides in JP 71018564 (Japan Gas Chem Co.). Several other 2-amino-1,3-thiazole derivatives have been reported in the art as useful therapeutic agents. In particular, 5-methyl-1,3-thiazoles further substituted in position 2 of the thiazole ring by a benzothiazinylcarbonylamino moiety, or derivatives thereof, have been described as cyclooxygenase inhibitors; see, for instance, C.A. 126(1997):301540. 2-Benzamido-1,3-thiazoles are disclosed in EP-A-261503 (Valeas S.p.A.) as antiallergic agents; 5-Alkyl-2-phenylalkylcarbonylamino-1,3-thiazoles further substituted onto the phenyl ring with an alkenylcarbonyl or alkynylcarbonyl moieties are disclosed in WO 98/04536 (Otsuka Pharmaceutical Co.) as protein kinase C inhibitors. 5-Arylthio-2-acylamino-1,3-thiazole derivatives are disclosed in EP-A-412404 (Fujisawa Pharm. Co.) as antitumor agents. In addition, among the compounds reported in the art as therapeutic agents, DE 2128941 (Melle-Bezons) discloses 2-aminomethylcarbonylamino-5-chloro-1,3-thiazoles as antiinflammatory, sedative and analgesic agents; the compound 2-diethylaminomethylcarbonylamino-5-chloro-1,3-thiazole being specifically exemplified therein.

Accordingly, the present invention provides the use of a compound which is a 2-amino-1,3-thiazole derivative of formula (I)

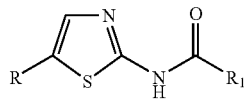

wherein
R is a halogen atom, a nitro group, an optionally substituted amino group or it is a group, optionally further substituted, selected from:
i) straight or branched $C_1$–$C_8$ alkyl, $C_2$–$C_6$ alkenyl or $C_2$–$C_6$ alkynyl;
ii) $C_3$–$C_6$ cycloalkyl;
iii) aryl or arylalkyl with from 1 to 8 carbon atoms within the straight or branched alkyl chain;
$R_1$ is an optionally further substituted group selected from:
i) straight or branched $C_1$–$C_8$ alkyl or $C_2$–$C_6$ alkenyl;
ii) 3 to 6 membered carbocycle or 5 to 7 membered heterocycle ring;
iii) aryl or arylcarbonyl;
iv) arylalkyl with from 1 to 8 carbon atoms within the straight or branched alkyl chain;
v) arylalkenyl with from 2 to 6 carbon atoms within the straight or branched alkenyl chain;
vi) an optionally protected amino acid residue;

or a pharmaceutically acceptable salt thereof; in the manufacture of a medicament for treating cell proliferative disorders associated with an altered cell dependent kinase activity.

According to a preferred embodiment of the invention, the said cell proliferative disorder is selected from the group consisting of cancer, Alzheimer's disease, viral infections, auto-immune diseases or neurodegenerative disorders. Preferably, the cancer is selected from the group consisting of carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xenoderoma pigmentosum, keratoctanthoma, thyroid follicular cancer and Kaposi's sarcoma.

According to another preferred embodiment of the invention, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis.

In addition, being useful in the treatment of cell proliferative disorders associated with an altered cell dependent kinase activity, hence cell cycle inhibition or cdk/cyclin dependent inhibition, the compounds of formula (I) of the invention also enable tumor angiogenesis and metastasis inhibition.

As above reported, some of the compounds of formula (I) of the invention have been reported in the art as useful therapeutic agents, for instance as antiinflammatory, sedative and analgesic agents.

Therefore, it is a further object of the present invention a compound which is a 2-amino-1,3-thiazole derivative of formula (I)

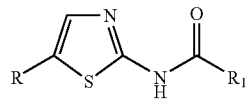

wherein
R is a halogen atom, a nitro group, an optionally substituted amino group or it is a group, optionally further substituted, selected from:
i) straight or branched $C_1$–$C_8$ alkyl, $C_2$–$C_6$ alkenyl or $C_2$–$C_6$ alkynyl;
ii) $C_3$–$C_6$ cycloalkyl;
iii) aryl or arylalkyl with from 1 to 8 carbon atoms within the straight or branched alkyl chain;
$R_1$ is an optionally further substituted group selected from:
i) straight or branched $C_1$–$C_8$ alkyl or $C_2$–$C_6$ alkenyl;
ii) 3 to 6 membered carbocycle or 5 to 7 membered heterocycle ring;
iii) aryl or arylcarbonyl;
iv) arylalkyl with from 1 to 8 carbon atoms within the straight or branched alkyl chain;
v) arylalkenyl with from 2 to 6 carbon atoms within the straight or branched alkenyl chain;
vi) an optionally protected amino acid residue;

or a pharmaceutically acceptable salt thereof; for use as a medicament; provided that each of R and $R_1$, independently, is not a methyl group and that the compound is not 2-diethylaminomethyl-carbonylamino-5-chloro-1,3-thiazole.

Among the compounds of formula (I) above reported, several derivatives result to be novel.

Therefore, the present invention further provides a compound which is a 2-amino-1,3-thiazole derivative of formula (I)

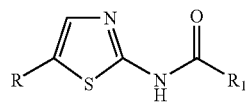

wherein
R is a halogen atom, a nitro group, an optionally substituted amino group or it is a group, optionally further substituted, selected from:
i) straight or branched $C_1$–$C_8$ alkyl, $C_2$–$C_6$ alkenyl or $C_2$–$C_6$ alkynyl;
ii) $C_3$–$C_6$ cycloalkyl;
iii) aryl or arylalkyl with from 1 to 8 carbon atoms within the straight or branched alkyl chain;
$R_1$ is an optionally further substituted group selected from:
straight or branched $C_1$–$C_8$ alkyl or $C_2$–$C_6$ alkenyl;
ii) 3 to 6 membered carbocycle or 5 to 7 membered heterocycle ring;
iii) aryl or arylcarbonyl;
iv) arylalkyl with from 1 to 8 carbon atoms within the straight or branched alkyl chain;

v) arylalkenyl with from 2 to 6 carbon atoms within the straight or branched alkenyl chain;

vi) an optionally protected amino acid residue;

or a pharmaceutically acceptable salt thereof; provided that:
a) R and $R_1$, each independently, are not methyl;
b) when R is bromine or chlorine then, $R_1$ is not unsubstituted $C_2$–$C_4$ alkyl or an optionally substituted aminomethyl;
c) when R is nitro or phenyl, then $R_1$ is not unsubstituted phenyl.

The compounds of formula (I) may have asymmetric carbon atoms and may therefore exist either as racemic admixtures or as individual optical isomers. Accordingly, all the possible isomers and their admixtures and of both the metabolites and the pharmaceutically acceptable bio-precursors (otherwise referred to as pro-drugs) of the compounds of formula (I), as well as the uses thereof, are also within the scope of the present invention.

In the present description, unless otherwise specified, with the term halogen atom we intend a chlorine, bromine, fluorine or iodine atom.

With the term optionally substituted amino group we intend an amino group wherein one or both hydrogen atoms are optionally replaced by other substituents which are the same or different, as set forth below.

With the term straight or branched $C_1$–$C_8$ alkyl we intend a group such as, for instance, methyl, ethyl, n.propyl, isopropyl, n.butyl, isobutyl, sec-butyl, tert-butyl, n.pentyl, n.hexyl, n.heptyl, n.octyl and the like.

With the term straight or branched $C_2$–$C_6$ alkenyl or alkynyl we intend a group such as, for instance, vinyl, allyl, isopropenyl, 1-, 2- or 3-butenyl, isobutylenyl, pentenyl, hexenyl, ethynyl, 1- or 2-propynyl, butynyl, pentynyl, hexynyl and the like.

With the term $C_3$–$C_6$ cycloalkyl we intend a cyclopropyl, cyclobutyl, cyclopentyl or cyclohexyl group.

With the term aryl, either as such or as arylalkyl, arylalkenyl, arylcarbonyl and the like, we intend a mono-, bi- or poly- either carbocyclic as well as heterocyclyc hydrocarbon with from 1 to 4 ring moieties, either fused or linked to each other by single bonds, wherein at least one of the carbocyclic or heterocyclic rings is aromatic. Examples of aryl groups are phenyl, indanyl, biphenyl, α- or β-naphthyl, fluorenyl, 9,10-dihydroanthracenyl, pyridyl, pyrazinyl, pyrimidinyl, pyridazinyl, indolyl, imidazolyl, 1,2-methylenedioxyphenyl, thiazolyl, isothiazolyl, pyrrolyl, pyrrolyl-phenyl, furyl, phenyl-furyl, benzotetrahydrofuran, oxazolyl, isoxazolyl, pyrazolyl, chromenyl, thienyl, benzothienyl, isoindolinyl, benzoimidazolyl, tetrazolyl, tetrazolylphenyl, pyrrolidinyl-tetrazolyl, isoindolinyl-phenyl, quinolinyl, isoquinolinyl, 2,6-diphenyl-pyridyl, quinoxalinyl, pyrazinyl, phenyl-quinolyl, benzofurazanyl, 1,2,3-triazole, 1-phenyl-1,2,3-triazole, and the like.

With the term 3 to 6 membered carbocycle, hence encompassing but not limited to $C_3$–$C_6$ cycloalkyl groups, we also intend an unsaturated carbocyclic hydrocarbon such as, for instance, cyclopentylene or cyclohexylene.

With the term 5 to 7 membered heterocycle, hence encompassing aromatic heterocycles also referred to as aryl groups, we further intend a saturated or partially unsaturated 5 to 7 membered carbocyle wherein one or more carbon atoms are replaced by heteroatoms such as nitrogen, oxygen and sulphur. Examples of 5 to 7 membered heterocycles, optionally benzocondensed or further substituted, are 1,3-dioxolane, pyran, pyrrolidine, pyrroline, imidazolidine, pyrazolidine, pyrazoline, piperidine, piperazine, N-alkyl-piperazine, morpholine, tetrahydrofuran and the like.

With the term amino acid residue we intend the residue of a natural α-amino acid of formula HOOC—$R_1$, wherein $R_1$ is bonded to the thiazole-NH—C(═O)— moiety and is represented by a —CH(Z)NHY group wherein Z is the characterising portion of the amino acid and Y is hydrogen or a suitable amino protecting group such as, for instance, tertbutoxycarbonyl or benzyloxycarbonyl. Examples of α-amino acids are alanine, isoleucine, glycine, lysine, arginine, cystine, histidine, leucine, proline and the like.

According to the above indicated substituent meanings, any of the above R and $R_1$ groups may be optionally substituted in any of the free positions by one or more groups, for instance 1 to 6 groups, selected from: halogen, nitro, oxo groups (═O), carboxy, cyano, alkyl, perfluorinated alkyl, alkenyl, alkynyl, cycloalkyl, aryl, heterocycyl; amino groups and derivatives thereof such as, for instance, alkylamino, alkoxycarbonylalkylamino, dialkylamino, arylamino, diarylamino or arylureido; carbonylamino groups and derivatives thereof such as, for instance, hydrogenocarbonylamino (HCONH—), alkylcarbonylamino, alkenylcarbonylamino, arylcarbonylamino, alkoxycarbonylamino; oxygen-substituted oximes such as, for instance, alkoxycarbonylalkoxyimino or alkoxyimino; hydroxy groups and derivatives thereof such as, for instance, alkoxy, aryloxy, alkylcarbonyloxy, arylcarbonyloxy, cycloalkenyloxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulphonyl, arylsulphonyl, alkylsulphinyl, arylsulphinyl, arylsulphonyloxy, aminosulfonyl, alkylaminosulphonyl or dialkylaminosulphonyl. In their turn, whenever appropriate, each of the above possible substituents on R and $R_1$ may be further substituted by one or more of the aforementioned groups. Examples of compounds of formula (I) wherein R and $R_1$ groups are substituted by one or more of the aforementioned substituents which, in their turn, are optionally further substituted as set forth above, are given below.

Pharmaceutically acceptable salts of the compounds of formula (I) are the acid addition salts with inorganic or organic, e.g. nitric, hydrochloric, hydrobromic, sulphuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid, as well as the salts with inorganic or organic bases, e.g. alkali or alkaline-earth metals, especially sodium, potassium, calcium or magnesium hydroxides, carbonates or bicarbonates, acyclic or cyclic amines, preferably methylamine, ethylamine, diethylamine, triethylamine or piperidine.

The compounds of formula (I) may have asymmetric carbon atoms and may therefore exist either as racemic admixtures or as individual optical isomers. Accordingly, the use as an antitumor agent of all the possible isomers and their admixtures and of both the metabolites and the pharmaceutically acceptable biopresursors (otherwise referred to as pro-drugs) of the compounds of formula (I) are also within the scope of the present invention.

Preferred compounds of formula (I), according to the present invention, are 2-amino-1,3-thiazole derivatives wherein R is a halogen atom or an optionally substituted group selected from a straight or branched $C_1$–$C_4$ alkyl, $C_3$–$C_6$ cycloalkyl, aryl or an arylalkyl with from 1 to 4 carbon atoms within the alkyl chain; $R_1$ is an optionally substituted group selected from straight or branched $C_1$–$C_4$ alkyl or alkenyl, aryl or arylalkyl with from 1 to 4 carbon atoms within the alkyl chain or it is an optionally protected amino acid residue.

Still more preferred compounds, within this class, are the derivatives of formula (I) wherein R is a bromine or chlorine atom or is an optionally substituted group selected from straight or branched $C_1$–$C_4$ alkyl, cyclopropyl, aryl or arylalkyl with from 1 to 2 carbon atoms within the alkyl chain; $R_1$ is an optionally substituted group selected from straight or branched $C_1$–$C_4$ alkyl or alkenyl, aryl or arylalkyl with from 1 to 4 carbon atoms within the alkyl chain or it is an optionally protected amino acid residue.

Another class of preferred compounds of the invention are the compounds of formula (I)

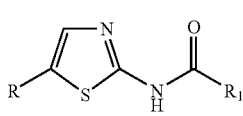

(I)

wherein
R is a halogen atom or is selected from nitro, amino, alkylamino, hydroxyalkylamino, arylamino, $C_3$–$C_6$ cycloalkyl and straight or branched $C_1$–$C_6$ alkyl which is unsubstituted or substituted by hydroxy, alkylthio, alkoxy, amino, alkylamino, alkoxycarbonylamino, alkoxycarbonylalkylamino, alkylcarbonyl, alkylsulfonyl, alkoxycarbonyl, carboxy or aryl which is unsubstituted or substituted by one or more hydroxy, halogen, nitro, alkoxy, aryloxy, alkylthio, arylthio, amino, alkylamino, dialkylamino, N-alkyl-piperazinyl, 4-morpholinyl, arylamino, cyano, alkyl, phenyl, aminosulfonyl, aminocarbonyl, alkylcarbonyl, arylcarbonyl, alkoxycarbonyl or carboxy groups, or R is an aryl group which is unsubstituted or substituted by one or more hydroxy, halogen, nitro, alkoxy, aryloxy, alkylthio, arylthio, amino, alkylamino, dialkylamino, N-alkyl-piperazinyl, 4-morpholinyl, arylamino, cyano, alkyl, phenyl, aminosulphonyl, aminocarbonyl, alkylcarbonyl, arylcarbonyl, alkoxycarbonyl or carboxy groups;
$R_1$ is a straight or branched $C_1$–$C_6$ alkyl group or an aryl group, each being unsubstituted or substituted as defined above for R;

or a pharmaceutically acceptable salt thereof; provided that:
a) R and $R_1$, each independently, are not methyl;
b) when R is bromine or chlorine then, $R_1$ is not unsubstituted $C_2$–$C_4$ alkyl or an optionally substituted aminomethyl;
c) when R is nitro or phenyl, then $R_1$ is not unsubstituted phenyl.

Examples of preferred compounds of the invention, whenever appropriate in the form of pharmaceutically acceptable salts, e.g. hydrobromide or hydrochloride salt, are the following:
1. ethyl 3-[(5-bromo-1,3-thiazol-2-yl)amino]-3-oxopropanoate;
2. N-(5-bromo-1,3-thiazol-2-yl)-2-phenyl-acetamide;
3. N-(5-bromo-1,3-thiazol-2-yl)-benzamide;
4. Ethyl 4-[(5-bromo-1,3-thiazol-2-yl)amino]-4-oxobutanoate;
5. N-(5-Bromo-thiazol-2-yl)-3-hydroxy-propionamide;
6. N-(5-Bromo-thiazol-2-yl)-4-hydroxybutanamide;
7. N-(5-Bromo-thiazol-2-yl)-2-ethoxy-acetamide;
8. 2-N-[2-(3-pyridyl)-acetyl-amino]-5-bromo-thiazole;
9. 2-N-[2-(3-pyridyl)-acetyl-amino]-5-isopropyl-thiazole;
10. N-(5-bromo-1,3-thiazol-2-yl)-2-(3-hydroxyphenyl)acetamide;
11. N-(5-isopropyl-1,3-thiazol-2-yl)-2-(3-hydroxyphenyl)acetamide
12. N-(5-bromo-1,3-thiazol-2-yl)-2-(3-methoxyphenyl)acetamide;
13. N-(5-isopropyl-1,3-thiazol-2-yl)-2-(3-methoxyphenyl)acetamide;
14. N-(5-bromo-1,3-thiazol-2-yl)-2-(3-chorophenyl)acetamide;
15. N-(5-isopropyl-1,3-thiazol-2-yl)-2-(3-chorophenyl)acetamide;
16. N-(5-bromo-1,3-thiazol-2-yl)-2-(4-hydroxyphenyl)acetamide;
17. N-(5-isopropyl-1,3-thiazol-2-yl)-2-(4-hydroxyphenyl)acetamide;
18. N-(5-bromo-1,3-thiazol-2-yl)-2-(3,4-dihydroxyphenyl)acetamide;
19. N-(5-isopropyl-1,3-thiazol-2-yl)-2-(3,4-dihydroxyphenyl)acetamide;
20. N-(5-bromo-1,3-thiazol-2-yl)-2-(4-hydroxy-3-methoxyphenyl)acetamide;
21. N-(5-isopropyl-1,3-thiazol-2-yl)-2-(4-hydroxy-3-methoxyphenyl)acetamide;
22. N-(5-bromo-1,3-thiazol-2-yl)-2-(4-methoxyphenyl)acetamide;
23. N-(5-isopropyl-1,3-thiazol-2-yl)-2-(4-methoxyphenyl)acetamide;
24. N-(5-isopropyl-1,3-thiazol-2-yl)-2-(4-chlorophenyl)acetamide;
25. N-(5-isopropyl-1,3-thiazol-2-yl)-2-phenyl-acetamide;
26. N-(5-bromo-thiazol-2-yl)-4-sulfamoyl-benzamide;
27. N-(5-isopropyl-thiazol-2-yl)-4-sulfamoyl-benzamide;
28. 4-amino-N-(5-bromo-1,3-thiazol-2-yl)butanamide;
29. 3-amino-N-(5-bromo-1,3-thiazol-2-yl) propionamide;
30. N-(5-isopropyl-1,3-thiazol-2-yl)-butanamide;
31. N-(5-bromo-1,3-thiazol-2-yl)-butanamide;
32. N-(5-chloro-1,3-thiazol-2-yl)-butanamide;
33. N-(5-phenyl-1,3-thiazol-2-yl)-butanamide;
34. N-(5-nitro-1,3-thiazol-2-yl)-butanamide;
35. N-(5-methyl-1,3-thiazol-2-yl)-butanamide;
36. N-(5-benzyl-1,3-thiazol-2-yl)-butanamide;
37. N-(5-isobutyl-1,3-thiazol-2-yl)-butanamide;
38. N-(5-cyclopropyl-1,3-thiazol-2-yl)-butanamide;
39. N-{5-[2-(methylsulfonyl)ethyl]-1,3-thiazol-2-yl}-butanamide;
40. N-[5-(2-methylthioethyl)-1,3-thiazol-2-yl]-butanamide;
41. N-{5-[2-(methoxycarbonyl)ethyl]-1,3-thiazol-2-yl}butanamide;
42. N-[5-(3-methoxy-propyl)-1,3-thiazol-2-yl]-butanamide;
43. N-[5-(2-ethoxy-ethyl)-1,3-thiazol-2-yl]-butanamide;
44. N-[5-(indol-3-yl-methyl)-1,3-thiazol-2-yl]-butanamide;
45. N-[5-(3-oxo-butyl)-1,3-thiazol-2 yl]-butanamide;
46. 2-[3-(3-chloropropoxy)phenyl]-N-(5-isopropyl-1,3-thiazol-2-yl)acetamide
47. 2-[3-(2-chloroethoxy)phenyl]-N-(5-isopropyl-1,3-thiazol-2-yl) acetamide
48. 2-(4-aminophenyl)-N-(5-isopropyl-1,3-thiazol-2-yl)acetamide
49. 4-amino-N-(5-isopropyl-1,3-thiazol-2-yl)benzamide
50. 2-(2-amino-1,3-thiazol-4-yl)-N-(5-isopropyl-1,3-thiazol-2-yl)acetamide
51. N-(5-isopropyl-1,3-thiazol-2-yl)-2-{3-[3-(4-morpholinyl)propoxy]phenyl}acetamide 52. N-(5-isopropyl-1,3-thiazol-2'-yl)-2-{3-[2-(4-morpholinyl)ethoxy]phenyl}acetamide
53. N-(5-isopropyl-1,3-thiazol-2-yl)-2-{3-[3-(1-pirrolidinyl)propoxy]phenyl}acetamide
54. N-(5-isopropyl-1,3-thiazol-2-yl)-2-{3-[3-(4-methyl-1-piperazinyl)propoxy]phenyl}acetamide
55. 2-{3-[2-(dimethylamino)ethoxy]phenyl}-N-(5-isopropyl-1,3-thiazol-2-yl)acetamide;
56. 2-{3-[3-(dimethylamino)propoxy]phenyl}-N-(5-isopropyl-1,3-thiazol-2-yl)acetamide
57. 2-[4-(dimethylamino)phenyl]-N-(5-isobutyl-1,3-thiazol-2-yl)acetamide
58. 2-(1,3-benzodioxol-5-yl)-N-(5-isobutyl-1,3-thiazol-2-yl)acetamide
59. N-(5-benzyl-1,3-thiazol-2-yl)-2-[4-(dimethylamino)phenyl]acetamide
60. N-(5-isopropyl-1,3-thiazol-2-yl)-2-[3-(2-methoxyethoxy)-phenyl]acetamide
61. 3-chloro-N-(5-isopropyl-1,3-thiazol-2-yl)-4-(4-methyl-1-piperazinyl)benzamide
62. N-(5-isobutyl-1,3-thiazol-2-yl)-2-(3-pyridinyl)acetamide
63. N-(5-benzyl-1,3-thiazol-2-yl)-2-(3-pyridinyl)acetamide
64. 2'-[N-[2'-N'-(ethoxycarbonyl-methyl)-amino]-acetyl]amino-5-bromo-thiazole
65. 2-anilino-N-(5-isopropyl-1,3-thiazol-2-yl)acetamide
66. (R)-N-(5-isopropyl-1,3-thiazol-2-yl)-2-phenylpropanamide
67. (S)-N-(5-isopropyl-1,3-thiazol-2-yl)-2-phenylpropanamide
68. N-(5-isopropyl-1,3-thiazol-2-yl)benzamide
69. 2,5-dichloro-N-(5-isopropyl-1,3-thiazol-2-yl)benzamide
70. 3,5-dichloro-N-(5-isopropyl-1,3-thiazol-2-yl)benzamide
71. 3,4-dichloro-N-(5-isopropyl-1,3-thiazol-2-yl)benzamide
72. 2,4-dichloro-N-(5-isopropyl-1,3-thiazol-2-yl)benzamide
73. 2,3-dichloro-N-(5-isopropyl-1,3-thiazol-2-yl)benzamide
74. 3-iodio-N-(5-isopropyl-1,3-thiazol-2-yl)benzamide
75. 2-iodio-N-(5-isopropyl-1,3-thiazol-2-yl)benzamide
76. 4-iodio-N-(5-isopropyl-1,3-thiazol-2-yl)benzamide
77. 3-bromo-N-(5-isopropyl-1,3-thiazol-2-yl)benzamide
78. 4-chloro-2-fluoro-N-(5-isopropyl-1,3-thiazol-2-yl)benzamide
79. 5-bromo-2-chloro-N-(5-isopropyl-1,3-thiazol-2-yl)benzamide
80. 3-chloro-N-(5-isopropyl-1,3-thiazol-2-yl)benzamide
81. 2-chloro-N-(5-isopropyl-1,3-thiazol-2-yl)benzamide
82. 4-chloro-N-(5-isopropyl-1,3-thiazol-2-yl)benzamide
83. 3-fluoro-N-(5-isopropyl-1,3-thiazol-2-yl)benzamide
84. 2-fluoro-N-(5-isopropyl-1,3-thiazol-2-yl)benzamide
85. 4-fluoro-N-(5-isopropyl-1,3-thiazol-2-yl)benzamide
86. 2,4-difluoro-N-(5-isopropyl-1,3-thiazol-2-yl)benzamide
87. 3,4-difluoro-N-(5-isopropyl-1,3-thiazol-2-yl)benzamide
88. 2,3,4,5,6-pentafluoro-N-(5-isopropyl-1,3-thiazol-2-yl)benzamide
89. N-(5-isopropyl-1,3-thiazol-2-yl)-4-methyl-3-nitrobenzamide
90. N-(5-isopropyl-1,3-thiazol-2-yl)-5-methyl-2-nitrobenzamide
91. N-(5-isopropyl-1,3-thiazol-2-yl)-3-methyl-2-nitrobenzamide
92. N-(5-isopropyl-1,3-thiazol-2-yl)-3,5-dimethyl-4-nitrobenzamide
93. N-(5-isopropyl-1,3-thiazol-2-yl)-4-methoxy-2-nitrobenzamide
94. N-(5-isopropyl-1,3-thiazol-2-yl)-3-methoxy-2-nitrobenzamide
95. N-(5-isopropyl-1,3-thiazol-2-yl)-4-methoxy-3-nitrobenzamide
96. N-(5-isopropyl-1,3-thiazol-2-yl)-3-methoxy-4-nitrobenzamide
97. N-(5-isopropyl-1,3-thiazol-2-yl)-3,5-dinitrobenzamide
98. 5-{[(5-isopropyl-1,3-thiazol-2-yl)amino]carbonyl}-2-nitrophenyl octanoate
99. N-(5-isopropyl-1,3-thiazol-2-yl)-3-nitrobenzamide
100. N-(5-isopropyl-1,3-thiazol-2-yl)-2-nitrobenzamide
101. N-(5-isopropyl-1,3-thiazol-2-yl)-4-nitrobenzamide
102. N-(5-isopropyl-1,3-thiazol-2-yl)-4-(methylsulfonyl)-3-nitrobenzamide
103. 4-chloro-N-(5-isopropyl-1,3-thiazol-2-yl)-3-nitrobenzamide
104. 6-chloro-N-(5-isopropyl-1,3-thiazol-2-yl)-3-nitrobenzamide
105. 4-chloro-N-(5-isopropyl-1,3-thiazol-2-yl)-2-nitrobenzamide
106. 2-chloro-N-(5-isopropyl-1,3-thiazol-2-yl)-4-nitrobenzamide
107. 5-chloro-N-(5-isopropyl-1,3-thiazol-2-yl)-2-nitrobenzamide
108. 2-bromo-N-(5-isopropyl-1,3-thiazol-2-yl)-5-nitrobenzamide
109. 4-fluoro-N-(5-isopropyl-1,3-thiazol-2-yl)-3-nitrobenzamide
110. 4-fluoro-N-(5-isopropyl-1,3-thiazol-2-yl)-2-nitrobenzamide
111. N-(5-isopropyl-1,3-thiazol-2-yl)-2-nitro-4-(trifluoromethyl)benzamide
112. N-(5-isopropyl-1,3-thiazol-2-yl)-3,5-bis(trifluoromethyl)benzamide
113. N-(5-isopropyl-1,3-thiazol-2-yl)-2,6-bis(trifluoromethyl)benzamide
114. N-(5-isopropyl-1,3-thiazol-2-yl)-2-(trifluoromethyl)benzamide
115. N-(5-isopropyl-1,3-thiazol-2-yl)-3-(trifluoromethyl)benzamide
116. 3-fluoro-N-(5-isopropyl-1,3-thiazol-2-yl)-4-(trifluoromethyl)benzamide
117. 2-fluoro-N-(5-isopropyl-1,3-thiazol-2-yl)-3-(trifluoromethyl)benzamide
118. 5-fluoro-N-(5-isopropyl-1,3-thiazol-2-yl)-3-(trifluoromethyl)benzamide
119. 2-fluoro-N-(5-isopropyl-1,3-thiazol-2-yl)-4-(trifluoromethyl)benzamide
120. 4-fluoro-N-(5-isopropyl-1,3-thiazol-2-yl)-3-(trifluoromethyl)benzamide
121. methyl 4-{[(5-isopropyl-1,3-thiazol-2-yl)amino]carbonyl}benzoate
122. methyl 2-{[(5-isopropyl-1,3-thiazol-2-yl)amino]carbonyl}benzoate
123. 4-cyano-N-(5-isopropyl-1,3-thiazol-2-yl)benzamide
124. 3-cyano-N-(5-isopropyl-1,3-thiazol-2-yl)benzamide
125. N-(5-isopropyl-1,3-thiazol-2-yl)-3-methylbenzamide
126. N-(5-isopropyl-1,3-thiazol-2-yl)-2-methylbenzamide
127. N-(5-isopropyl-1,3-thiazol-2-yl)-2-methylbenzamide
128. N-(5-isopropyl-1,3-thiazol-2-yl)-4-vinylbenzamide
129. N-(5-isopropyl-1,3-thiazol-2-yl)-4-(2-phenylethynyl)benzamide
130. N-(5-isopropyl-1,3-thiazol-2-yl)-3-methoxy-4-methylbenzamide
131. 2-benzyl-N-(5-isopropyl-1,3-thiazol-2-yl)benzamide
132. N-(5-isopropyl-1,3-thiazol-2-yl)-2-phenethylbenzamide
133. N-(5-isopropyl-1,3-thiazol-2-yl)-2-phenylbenzamide
134. N-(5-isopropyl-1,3-thiazol-2-yl)-4-phenylbenzamide 135. 4-(tert-butyl)-N-(5-isopropyl-1,3-thiazol-2-yl)benzamide
136. N-(5-isopropyl-1,3-thiazol-2-yl)-4-isopropylbenzamide
137. N-(5-isopropyl-1,3-thiazol-2-yl)-4-pentylbenzamide
138. 3-fluoro-N-(5-isopropyl-1,3-thiazol-2-yl)-4-methylbenzamide
139. N-(5-isopropyl-1,3-thiazol-2-yl)-3,4-dimethylbenzamide
140. N-(5-isopropyl-1,3-thiazol-2-yl)-3,5-dimethylbenzamide
141. 4-acetyl-N-(5-isopropyl-1,3-thiazol-2-yl)benzamide
142. N-(5-isopropyl-1,3-thiazol-2-yl)-4-(methylsulfonyl)benzamide
143. 5-(aminosulfonyl)-2,4-dichloro-N-(5-isopropyl-1,3-thiazol-2-yl)benzamide
144. 5-(aminosulfonyl)-4-chloro-N-(5-isopropyl-1,3-thiazol-2-yl)benzamide
145. 3-fluoro-N-(5-isopropyl-1,3-thiazol-2-yl)-4-methoxybenzamide
146. 3-chloro-N-(5-isopropyl-1,3-thiazol-2-yl)-4-methoxybenzamide
147. 5-chloro-N-(5-isopropyl-1,3-thiazol-2-yl)-2-methoxybenzamide
148. N-(5-isopropyl-1,3-thiazol-2-yl)-4-methoxybenzamide
149. N-(5-isopropyl-1,3-thiazol-2-yl)-3-methoxybenzamide
150. N-(5-isopropyl-1,3-thiazol-2-yl)-2-methoxybenzamide
151. N-(5-isopropyl-1,3-thiazol-2-yl)-3,4-dimethoxybenzamide
152. N-(5-isopropyl-1,3-thiazol-2-yl)-3,5-dimethoxybenzamide
153. N-(5-isopropyl-1,3-thiazol-2-yl)-2,4-dimethoxybenzamide
154. N-(5-isopropyl-1,3-thiazol-2-yl)-2,3-dimethoxybenzamide
155. N-(5-isopropyl-1,3-thiazol-2-yl)-3-phenoxybenzamide
156. N-(5-isopropyl-1,3-thiazol-2-yl)-2-phenoxybenzamide
157. N-(5-isopropyl-1,3-thiazol-2-yl)-4-phenoxybenzamide
158. 2-ethoxy-N-(5-isopropyl-1,3-thiazol-2-yl)benzamide
159. 4-ethoxy-N-(5-isopropyl-1,3-thiazol-2-yl)benzamide
160. N-(5-isopropyl-1,3-thiazol-2-yl)-3,4,5-trimethoxybenzamide
161. 3,4-diethoxy-N-(5-isopropyl-1,3-thiazol-2-yl)benzamide
162. 3,4,5-triethoxy-N-(5-isopropyl-1,3-thiazol-2-yl)benzamide
163. N-(5-isopropyl-1,3-thiazol-2-yl)-3-methoxy-4-(methoxymethoxy)benzamide
164. 4-butoxy-N-(5-isopropyl-1,3-thiazol-2-yl)benzamide
165. N-(5-isopropyl-1,3-thiazol-2'-yl)-4-propoxybenzamide
166. 4-isopropoxy-N-(5-isopropyl-1,3-thiazol-2-yl)benzamide
167. N-(5-isopropyl-1,3-thiazol-2-yl)-1,3-benzodioxole-5-carboxamide
168. 4-(benzyloxy)-N-(5-isopropyl-1,3-thiazol-2-yl)benzamide
169. 4-(2-cyclohexen-1-yloxy)-N-(5-isopropyl-1,3-thiazol-2-yl)benzamide
170. N-(5-isopropyl-1,3-thiazol-2-yl)-4-(trifluoromethoxy)benzamide
171. 4-(difluoromethoxy)-N-(5-isopropyl-1,3-thiazol-2-yl)benzamide
172. N-(5-isopropyl-1,3-thiazol-2-yl)-4-(methylsulfanyl)benzamide
173. 2-[(4-chlorophenyl)sulfinyl]-N-(5-isopropyl-1,3-thiazol-2-yl)benzamide
174. N-(5-isopropyl-1,3-thiazol-2-yl)-2-[(4-nitrophenyl)sulfinyl]benzamide
175. N-(5-isopropyl-1,3-thiazol-2-yl)-4-[(4-methylphenyl)sulfonyl]-3-nitrobenzamide
176. N-(5-isopropyl-1,3-thiazol-2-yl)-3-[(trifluoromethyl)sulfanyl]benzamide
177. N-(5-isopropyl-1,3-thiazol-2-yl)-2-methoxy-4-(methylsulfanyl)benzamide
178. 2-[(2-cyanophenyl)sulfanyl]-N-(5-isopropyl-1,3-thiazol-2-yl)benzamide
179. N~1,N~1~-diethyl-3,6-difluoro-N~2~-(5-isopropyl-1,3-thiazol-2-yl)phthalamide
180. 4-formyl-N-(5-isopropyl-1,3-thiazol-2-yl)benzamide
181. 2-formyl-N-(5-isopropyl-1,3-thiazol-2-yl)benzamide
182. 4-{[(2,5-dimethoxyanilino)carbonyl]amino}-N-(5-isopropyl-1,3-thiazol-2-yl)benzamide
183. 4-(hydroxymethyl)-N-(5-isopropyl-1,3-thiazol-2-yl)benzamide
184. 4-{[(5-isopropyl-1,3-thiazol-2-yl)amino]carbonyl}-2-nitrobenzyl acetate
185. 4-{[(5-isopropyl-1,3-thiazol-2-yl)amino]carbonyl}-2-nitrobenzyl 4-(acetylamino)-3-iodobenzoate
186. 4-(acetylamino)-N-(5-isopropyl-1,3-thiazol-2-yl)benzamide
187. N-(5-isopropyl-1,3-thiazol-2-yl)-4-[(2-phenylacetyl)amino]benzamide
188. 4-(acetylamino)-3-iodo-N-(5-isopropyl-1,3-thiazol-2-yl)benzamide
189. 4-amino-N-(5-isopropyl-1,3-thiazol-2-yl)benzamide
190. 4-(dimethylamino)-N-(5-isopropyl-1,3-thiazol-2-yl)benzamide
191. 3-(dimethylamino)-N-(5-isopropyl-1,3-thiazol-2-yl)benzamide
192. 2-(methylamino)-N-(5-isopropyl-1,3-thiazol-2-yl)benzamide
193. N-(5-isopropyl-1,3-thiazol-2-yl)-2-[3-(trifluoromethyl)anilino]benzamide
194. 3-{[5-bromo-1,3-dioxo-1,3-dihydro-2H-isoindol-2-yl)methyl]amino}-N-(5-isopropyl-1,3-thiazol-2-yl)benzamide
195. N-(5-isopropyl-1,3-thiazol-2-yl)-4-(1H-pyrrol-1-yl)benzamide
196. 2,6-dichloro-N-(5-isopropyl-1,3-thiazol-2-yl)isonicotinamide
197. 2-(4-bromophenyl)-6-(4-iodophenyl)-N-(5-isopropyl-1,3-thiazol-2-yl)isonicotinamide
198. N-(5-isopropyl-1,3-thiazol-2-yl)-2-[3-(trifluoromethyl)anilino]nicotinamide
199. 2,6-dichloro-N-(5-isopropyl-1,3-thiazol-2-yl)nicotinamide
200. 5,6-dichloro-N-(5-isopropyl-1,3-thiazol-2-yl)nicotinamide
201. 2-chloro-N-(5-isopropyl-1,3-thiazol-2-yl)-6-methylnicotinamide
202. 2,6-dichloro-5-fluoro-N-(5-isopropyl-1,3-thiazol-2-yl)nicotinamide
203. N-(5-isopropyl-1,3-thiazol-2-yl)-2-phenoxynicotinamide
204. N-(5-isopropyl-1,3-thiazol-2-yl)-6-(2,2,2-trifluoroethoxy)nicotinamide
205. N-(5-isopropyl-1,3-thiazol-2-yl)-2,6-dimethoxynicotinamide
206. N-(5-isopropyl-1,3-thiazol-2-yl)-2-quinoxalinecarboxamide
207. N-(5-isopropyl-1,3-thiazol-2-yl)-5-methyl-2-pyrazinecarboxamide 208. N-(5-isopropyl-1,3-thiazol-2-yl)-8-quinolinecarboxamide
209. N-(5-isopropyl-1,3-thiazol-2-yl)-2-phenyl-4-quinolinecarboxamide
210. N-(5-isopropyl-1,3-thiazol-2-yl)-5-methyl-1-phenyl-1H-pyrazole-4-carboxamide
211. N-(5-isopropyl-1,3-thiazol-2-yl)-5-methyl-1H-pyrazole-3-carboxamide
212. N-(5-isopropyl-1,3-thiazol-2-yl)-1H-pyrazole-4-carboxamide
213. N-(5-isopropyl-1,3-thiazol-2-yl)-5-methyl-2-phenyl-2H-1,2,3-triazole-4-carboxamide
214. 2-[(2,1,3-benzoxadiazol-5-yloxy)methyl]-N-(5-isopropyl-1,3-thiazol-2-yl)-4-methyl-1,3-thiazole-5-carboxamide
215. N-(5-isopropyl-1,3-thiazol-2-yl)-9H-fluorene-1-carboxamide
216. N-(5-isopropyl-1,3-thiazol-2-yl)-7-methoxy-1-benzofuran-2-carboxamide
217. N-(5-isopropyl-1,3-thiazol-2-yl)-1-[(4-methylphenyl)sulfonyl]-1H-pyrrole-3-carboxamide
218. 2-ethoxy-N-(5-isopropyl-1,3-thiazol-2-yl)-1-naphthamide
219. 4-fluoro-N-(5-isopropyl-1,3-thiazol-2-yl)-1-naphthamide
220. N-(5-isopropyl-1,3-thiazol-2-yl)-2-naphthamide
221. N-(5-isopropyl-1,3-thiazol-2-yl)-9,10-dioxo-9,10-dihydro-2-anthracenecarboxamide
222. N-(5-isopropyl-1,3-thiazol-2-yl)-9-oxo-9H-fluorene-4-carboxamide
223. N-(5-isopropyl-1,3-thiazol-2-yl)-9-oxo-9H-fluorene-1-carboxamide
224. N-(5-isopropyl-1,3-thiazol-2-yl)-8-oxo-5,6,7,8-tetrahydro-2-naphthalenecarboxamide
225. N-(5-isopropyl-1,3-thiazol-2-yl)-1,3-dioxo-1,3-dihydro-2-benzofuran-5-carboxamide
226. N-(5-isopropyl-1,3-thiazol-2-yl)-1H-indole-5-carboxamide
227. N-(5-isopropyl-1,3-thiazol-2-yl)-1H-indole-4-carboxamide
228. N-(5-isopropyl-1,3-thiazol-2-yl)-1-methyl-2-phenyl-1H-indole-5-carboxamide
229. 2-butyl-N-(5-isopropyl-1,3-thiazol-2-yl)-1-methyl-1H-indole-5-carboxamide
230. N-(5-isopropyl-1,3-thiazol-2-yl)-1H-indole-6-carboxamide
231. N-(5-isopropyl-1,3-thiazol-2-yl)-5-methoxy-1H-indole-2-carboxamide
232. 1-allyl-2-butyl-N-(5-isopropyl-1,3-thiazol-2-yl)-1H-indole-5-carboxamide
233. N-(5-isopropyl-1,3-thiazol-2-yl)-1-methyl-1H-indole-2-carboxamide
234. 1-benzyl-N-(5-isopropyl-1,3-thiazol-2-yl)-2-phenyl-1H-indole-5-carboxamide
235. N-(5-isopropyl-1,3-thiazol-2-yl)-1H-1,2,3-benzotriazole-5-carboxamide
236. N-(5-isopropyl-1,3-thiazol-2-yl)-3,5-dimethyl-4-isoxazolecarboxamide
237. N-(5-isopropyl-1,3-thiazol-2-yl)-3-thiophenecarboxamide
238. N-(5-isopropyl-1,3-thiazol-2-yl)-3-methyl-2-thiophenecarboxamide
239. N-(5-isopropyl-1,3-thiazol-2-yl)-5-methyl-2-thiophenecarboxamide
240. 5-bromo-N-(5-isopropyl-1,3-thiazol-2-yl)-2-thiophenecarboxamide
241. N-(5-isopropyl-1,3-thiazol-2-yl)-3-[(2,3,3-trichloroacryloyl)amino]-2-thiophenecarboxamide
242. 5-bromo-N-(5-isopropyl-1,3-thiazol-2-yl)-2-furamide
243. N-(5-isopropyl-1,3-thiazol-2-yl)-2-furamide
244. N-(5-isopropyl-1,3-thiazol-2-yl)-5-(4-nitrophenyl)-2-furamide
245. N-(5-isopropyl-1,3-thiazol-2-yl)-5-(2-nitrophenyl)-2-furamide
246. 5-(4-chlorophenyl)-N-(5-isopropyl-1,3-thiazol-2-yl)-2-furamide
247. N-(5-isopropyl-1,3-thiazol-2-yl)-5-[3-(trifluoromethyl)phenyl]-2-furamide
248. 5-(4-chloro-2-nitrophenyl)-N-(5-isopropyl-1,3-thiazol-2-yl)-2-furamide
249. N-(5-isopropyl-1,3-thiazol-2-yl)-5-(4-methyl-2-nitrophenyl)-2-furamide
250. 5-[2-chloro-5-(trifluoromethyl)phenyl]-N-(5-isopropyl-1,3-thiazol-2-yl)-2-furamide
251. tert-butyl (1R)-2-[(5-isopropyl-1,3-thiazol-2-yl)amino]-2-oxo-1-phenylethylcarbamate
252. (1R)-2-[(5-isopropyl-1,3-thiazol-2-yl)amino]-2-oxo-1-phenylethyl acetate
253. (1S)-2-[(5-isopropyl-1,3-thiazol-2-yl)amino]-2-oxo-1-phenylethyl acetate
254. (R,S)-2-fluoro-N-(5-isopropyl-1,3-thiazol-2-yl)-2-phenylacetamide
255. (R)-2-fluoro-N-(5-isopropyl-1,3-thiazol-2-yl)-2-phenylacetamide
256. (S)-2-fluoro-N-(5-isopropyl-1,3-thiazol-2-yl)-2-phenylacetamide
257. 2-(acetylamino)-N-(5-isopropyl-1,3-thiazol-2-yl)-2-phenylacetamide
258. (R,S)-2-(methoxy)-N-(5-isopropyl-1,3-thiazol-2-yl)-2-phenylacetamide
259. (R)-2-(methoxy)-N-(5-isopropyl-1,3-thiazol-2-yl)-2-phenylacetamide
260. (S)-2-(methoxy)-N-(5-isopropyl-1,3-thiazol-2-yl)-2-phenylacetamide
261. 3,3,3-trifluoro-N-(5-isopropyl-1,3-thiazol-2-yl)-2-methoxy-2-phenylpropanamide
262. N-(5-isopropyl-1,3-thiazol-2-yl)-2-(1-naphthyl)acetamide
263. N-(5-isopropyl-1,3-thiazol-2-yl)-2-(2-naphthyl)acetamide
264. 2-(1H-indol-3-yl)-N-(5-isopropyl-1,3-thiazol-2-yl)acetamide
265. 2-(1,3-benzodioxol-4-yl)-N-(5-isopropyl-1,3-thiazol-2-yl)acetamide
266. 2-(2,4-dinitrophenyl)-N-(5-isopropyl-1,3-thiazol-2-yl)acetamide
267. N-(5-isopropyl-1,3-thiazol-2-yl)-2-(2-methyl-1H-indol-3-yl)acetamide
268. N-(5-isopropyl-1,3-thiazol-2-yl)-2-(1-methyl-1H-indol-3-yl)acetamide
269. N-(5-isopropyl-1,3-thiazol-2-yl)-2-(5-methoxy-1H-indol-3-yl)acetamide
270. N-(5-isopropyl-1,3-thiazol-2-yl)-2-(5-benzyloxy-1H-indol-3-yl)acetamide
271. N-(5-isopropyl-1,3-thiazol-2-yl)-2-(3-methoxy-2-methyl-1H-indol-3-yl)acetamide
272. 2-(1H-indol-3-yl)-N-(5-isopropyl-1,3-thiazol-2-yl)-2-oxoacetamide
273. 2-(5-bromo-1H-indol-3-yl)-N-(5-isopropyl-1,3-thiazol-2-yl)acetamide
274. 2-(5-fluoro-1H-indol-3-yl)-N-(5-isopropyl-1,3-thiazol-2-yl)acetamide 275. 2-[1-(4-chlorobenzoyl)-5-methoxy-2-methyl-1H-indol-3-yl]-N-(5-isopropyl-1,3-thiazol-2-yl)acetamide
276. 3-(1H-indol-3-yl)-N-(5-isopropyl-1,3-thiazol-2-yl)propanamide
277. 4-(1H-indol-3-yl)-N-(5-isopropyl-1,3-thiazol-2-yl)butanamide
278. N-(5-isopropyl-1,3-thiazol-2-yl)-3-(2-thienyl)propanamide
279. N-(5-isopropyl-1,3-thiazol-2-yl)-2-(2-thienyl)acetamide
280. N-(5-isopropyl-1,3-thiazol-2-yl)-2-oxo-2-(2-thienyl)acetamide
281. N-(5-isopropyl-1,3-thiazol-2-yl)-2-(3-thienyl)acetamide
282. 2-(5-chloro-1-benzothiophen-3-yl)-N-(5-isopropyl-1,3-thiazol-2-yl)acetamide
283. 2-(1-benzothiophen-3-yl)-N-(5-isopropyl-1,3-thiazol-2-yl)acetamide
284. 2-[2-(formylamino)-1,3-thiazol-4-yl]-N-(5-isopropyl-1,3-thiazol-2-yl)-2-(methoxyimino)acetamide
285. 2-{2-[(2-chloroacetyl)amino]-1,3-thiazol-4-yl}-N-(5-isopropyl-1,3-thiazol-2-yl)-2-(methoxyimino)acetamide
286. 2-chloro-N-(4-{2-[(5-isopropyl-1,3-thiazol-2-yl)amino]-2-oxoethyl}-1,3-thiazol-2-yl)acetamide
287. ethyl 2-({[2-[(5-isopropyl-1,3-thiazol-2-yl)amino]-2-oxo-1-(1H-pyrazol-3-yl)ethylidene]amino}oxy)acetate
288. 2-(2-furyl)-N-(5-isopropyl-1,3-thiazol-2-yl)-2-oxoacetamide
289. 2-(5-bromo-3-pyridinyl)-N-(5-isopropyl-1,3-thiazol-2-yl)acetamide
290. N-(5-isopropyl-1,3-thiazol-2-yl)-2-(7-methoxy-2-oxo-2H-chromen-4-yl)acetamide
291. N-(5-isopropyl-1,3-thiazol-2-yl)-4-phenyl-3-butenamide
292. N-(5-isopropyl-1,3-thiazol-2-yl)-4-oxo-4-(4-methylphenyl)butanamide
293. N-(5-isopropyl-1,3-thiazol-2-yl)-4-(4-nitrophenyl)butanamide
294. N-(5-isopropyl-1,3-thiazol-2-yl)-4-phenylbutanamide
295. benzyl 4-[(5-isopropyl-1,3-thiazol-2-yl)amino-4-oxobutylcarbamate
296. methyl 5-[(5-isopropyl-1,3-thiazol-2-yl)amino]-5-oxopentanoate
297. 4-(1,3-dioxo-1,3-dihydro-2H-isoindol-2-yl)-N-(5-isopropyl-1,3-thiazol-2-yl)butanamide
298. N-(5-isopropyl-1,3-thiazol-2-yl)-4-(4-methoxy-1-naphthyl)-4-oxobutanamide
299. 3-(2-chlorophenoxy)-N-(5-isopropyl-1,3-thiazol-2-yl)propanamide
300. 3-(4-methylphenoxy)-N-(5-isopropyl-1,3-thiazol-2-yl)propanamide
301. 3-cyclopentyl-N-(5-isopropyl-1,3-thiazol-2-yl)propanamide
302. 3-cyclohexyl-N-(5-isopropyl-1,3-thiazol-2-yl)propanamide
303. N-(5-isopropyl-1,3-thiazol-2-yl)-4-methylpentanamide
304. 3-(4-chlorophenyl)-N-(5-isopropyl-1,3-thiazol-2-yl)propanamide
305. 3-(4-methoxyphenyl)-N-(5-isopropyl-1,3-thiazol-2-yl)propanamide
306. 3-chloro-N-(5-isopropyl-1,3-thiazol-2-yl)propanamide
307. 3-phenyl-N-(5-isopropyl-1,3-thiazol-2-yl)propanamide
308. 2-cyclohexyl-N-(5-isopropyl-1,3-thiazol-2-yl)acetamide
309. N-(5-isopropyl-1,3-thiazol-2-yl)-3-methylbutanamide
310. N-(5-isopropyl-1,3-thiazol-2-yl)-5-oxo-5-phenylpentanamide
311. 2-[(5-isopropyl-1,3-thiazol-2-yl)amino]-2-oxo-1-phenylethyl acetate
312. N-(5-isopropyl-1,3-thiazol-2-yl)-2-[4-(1-oxo-1,3-dihydro-9H-isoindol-2-yl)phenyl]propanamide
313. 1-(4-chlorophenyl)-N-(5-isopropyl-1,3-thiazol-2-yl)cyclopentanecarboxamide
314. 1-phenyl-N-(5-isopropyl-1,3-thiazol-2-yl)cyclopentanecarboxamide
315. 2-(3-bromo-4-methoxyphenyl)-N-(5-isopropyl-1,3-thiazol-2-yl)acetamide
316. 2-(2-nitro-4-trifluoromethylphenyl)-N-(5-isopropyl-1,3-thiazol-2-yl)acetamide
317. 5-cyclohexyl 1-(4-{2-[(5-isopropyl-1,3-thiazol-2-yl)amino]-2-oxoethyl}benzyl)(2S)-2-[(tert-butoxycarbonyl)amino]pentanedioate
318. 2-(5,6-dimethyl-1H-benzimidazol-1-yl)-N-(5-isopropyl-1,3-thiazol-2-yl)acetamide
319. 2'-[5-(4-chlorophenyl)-2H-1,2,3,4-tetraazol-2-yl]-N-(5-isopropyl-1,3-thiazol-2-yl)acetamide
320. N-(5-isopropyl-1,3-thiazol-2-yl)-2-[5-(1-pyrrolidinyl)-2H-1, 2, 3, 4-tetraazol-2-yl]acetamide
321. N-(5-isopropyl-1,3-thiazol-2-yl)-2-(3-methyl-1-benzothiophen-2-yl)acetamide
322. N-(5-isopropyl-1,3-thiazol-2-yl)-4,4-bis(4-methylphenyl)-3-butenamide
323. 2-cyclopropyl-N-(5-isopropyl-1,3-thiazol-2-yl)acetamide
324. N-{4-bromo-6-[(5-isopropyl-1,3-thiazol-2-yl)amino]-6-oxohexyl}benzamide
325. 2-cyclopentyl-N-(5-isopropyl-1,3-thiazol-2-yl)acetamide
326. benzyl 6-[(5-isopropyl-1,3-thiazol-2-yl)amino]-6-oxohexylcarbamate
327. N-1—(5-isopropyl-1,3-thiazol-2-yl)~N~4~-(2-propynyl)-2-butenediamide
328. 4-(2,4-dimethylphenyl)-N-(5-isopropyl-1,3-thiazol-2-yl)-4-oxobutanamide
329. 4-(4-benzyloxyphenyl)-N-(5-isopropyl-1,3-thiazol-2-yl)-4-oxobutanamide
330. 4-(thiphen-2-yl)-N-(5-isopropyl-1,3-thiazol-2-yl)-4-oxobutanamide
331. benzyl 2-{[(benzyloxy)carbonyl]amino}-5-[(5-isopropyl-1,3-thiazol-2-yl)amino]-5-oxopentanoate
332. 4-(1H-indol-3-yl)-N-{3-[(5-isopropyl-1,3-thiazol-2-yl)amino]-3-oxopropyl}butanamide
333. 4-{[(5-isopropyl-1,3-thiazol-2-yl)amino]carbonyl}phenyl 4-chlorobenzenesulfonate
334. N-(5-isopropyl-1,3-thiazol-2-yl)-4-{[(2-methoxyanilino)carbonyl]amino}benzamide
335. 4-{[2-(isopropylsulfonyl)acetyl]amino}-N-(5-isopropyl-1,3-thiazol-2-yl)benzamide
336. N-(5-isopropyl-1,3-thiazol-2-yl)-4-{[2-(phenylsulfanyl)acetyl]amino}benzamide
337. 4-[(diethylamino)sulfonyl]-N-(5-isopropyl-1,3-thiazol-2-yl)benzamide
338. 2-bromo-N-(5-isopropyl-1,3-thiazol-2-yl)benzamide
339. 3,5-difluoro-N-(5-isopropyl-1,3-thiazol-2-yl)benzamide
340. 3-{[(2-fluoroanilino)carbonyl]amino}-N-(5-isopropyl-1,3-thiazol-2-yl)benzamide
341. N-(5-isopropyl-1,3-thiazol-2-yl)-1-phenyl-5-propyl-1H-pyrazole-4-carboxamide
342. 3-chloro-4-(isopropylsulfonyl)-N-(5-isopropyl-1,3-thiazol-2-yl)-5-(methylsulfanyl)-2-thiophenecarboxamide
343. 3-iodo-4-(isopropylsulfonyl)-N-(5-isopropyl-1,3-thiazol-2-yl)-5-(methylsulfanyl)-2-thiophenecarboxamide 344. 2-{[(4-chlorophenyl)sulfonyl]methyl}-N-(5-isopropyl-1,3-thiazol-2-yl)-4-methyl-1,3-thiazole-5-carboxamide
345. 5-(4-chlorophenyl)-N-(5-isopropyl-1,3-thiazol-2-yl)-2-(trifluoromethyl)-3-furamide
346. N-(5-isopropyl-1,3-thiazol-2-yl)-2-(2,3,4,5,6-pentafluorophenyl)acetamide
347. N-(5-isopropyl-1,3-thiazol-2-yl)-2-(2-fluorophenyl)acetamide
348. N-(5-isopropyl-1,3-thiazol-2-yl)-2-(2-bromophenyl)acetamide
349. N-(5-isopropyl-1,3-thiazol-2-yl)-2-(2-chlorophenyl)acetamide
350. N-(5-isopropyl-1,3-thiazol-2-yl)-2-(2-nitrophenyl)acetamide
351. N-(5-isopropyl-1,3-thiazol-2-yl)-2-(2-trifluoromethylphenyl)acetamide
352. N-(5-isopropyl-1,3-thiazol-2-yl)-2 (2-methoxyphenyl)acetamide
353. N-(5-isopropyl-1,3-thiazol-2-yl)-2-(2,5-dimethoxyphenyl)acetamide
354. N-(5-isopropyl-1,3-thiazol-2-yl)-2-(2,5-difluorophenyl)acetamide
355. N-(5-isopropyl-1,3-thiazol-2-yl)-2-(3,4,5-trimethoxyphenyl) acetamide
356. N-(5-isopropyl-1,3-thiazol-2-yl)-2-(2,6-dichlorophenyl)acetamide
357. N-(5-isopropyl-1,3-thiazol-2-yl)-2-(2-chloro-6-fluorophenyl)acetamide
358. N-(5-isopropyl-1,3-thiazol-2-yl)-2-(3,5-dimethoxyphenyl)acetamide
359. N-(5-isopropyl-1,3-thiazol-2-yl)-2-(3,5-difluorophenyl)acetamide
360. N-(5-isopropyl-1,3-thiazol-2-yl)-2-(2,5-bis-trifluoromethylphenyl)acetamide
361. N-(5-isopropyl-1,3-thiazol-2-yl)-2-(4-methylthiophenyl)acetamide
362. N-(5-isopropyl-1,3-thiazol-2-yl)-2-(4-methoxyphenyl)acetamide
363. N-(5-isopropyl-1,3-thiazol-2-yl)-2-(4-bromophenyl)acetamide
364. N-(5-isopropyl-1,3-thiazol-2-yl)-2-(4-chlorophenyl)acetamide
365. N-(5-isopropyl-1,3-thiazol-2-yl)-2-(4-fluorophenyl)acetamide
366. N-(5-isopropyl-1,3-thiazol-2-yl)-2-(4-nitrophenyl)acetamide
367. N-(5-isopropyl-1,3-thiazol-2-yl)-2-(4-trifluoromethylphenyl)acetamide
368. N-(5-isopropyl-1,3-thiazol-2-yl)-2-(4-methylphenyl)acetamide
369. N-(5-isopropyl-1,3-thiazol-2-yl)-2-(4-dimethylaminophenyl)acetamide
370. 2-[1,1'-biphenyl]-4-yl-N-(5-isopropyl-1,3-thiazol-2-yl)acetamide
371. N-(5-isopropyl-1,3-thiazol-2-yl)-2-(3-trifluoromethylphenyl)acetamide
372. N-(5-isopropyl-1,3-thiazol-2-yl)-2-(3-bromophenyl)acetamide
373. N-(5-isopropyl-1,3-thiazol-2-yl)-2-(3-chlorophenyl)acetamide
374. N-(5-isopropyl-1,3-thiazol-2-yl)-2-(3-nitrophenyl)acetamide
375. N-(5-isopropyl-1,3-thiazol-2-yl)-2-(3-methoxyphenyl)acetamide
376. N-(5-isopropyl-1,3-thiazol-2-yl)-2-(2,4-dinitrophenyl)acetamide
377. N-(5-isopropyl-1,3-thiazol-2-yl)-2-(2,4-dichlorophenyl)acetamide
378. N-(5-isopropyl-1,3-thiazol-2-yl)-2-(2,4-difluorophenyl)acetamide
379. N-(5-isopropyl-1,3-thiazol-2-yl)-2-(4-benzyloxy-3-methoxyphenyl)acetamide
380. N-(5-isopropyl-1,3-thiazol-2-yl)-2-(3,4-dichlorophenyl)acetamide
381. N-(5-isopropyl-1,3-thiazol-2-yl)-2-(3,4-difluorophenyl)acetamide
382. N-(5-isopropyl-1,3-thiazol-2-yl)-2-(3,4-dimethoxyphenyl)acetamide
383. 2-(2,3-dihydro-1H-inden-5-yl)-N-(5-isopropyl-1,3-thiazol-2-yl)acetamide
384. N-(5-isopropyl-1,3-thiazol-2-yl)-1-phenylcyclopropanecarboxamide
385. 2-cyclopentyl-N-(5-isopropyl-1,3-thiazol-2-yl)-2-phenylacetamide
386. 2-cyclohexyl-N-(5-isopropyl-1,3-thiazol-2-yl)-2-phenylacetamide
387. N-(5-isopropyl-1,3-thiazol-2-yl)-2,2-diphenylacetamide
388. N-(5-isopropyl-1,3-thiazol-2-yl)-2-(2-nitrophenoxy)acetamide
389. N-(5-isopropyl-1,3-thiazol-2-yl)-2-(4-nitrophenyl)propanamide
390. N-(5-isopropyl-1,3-thiazol-2-yl)-2-phenyl)propanamide
391. N-(5-isopropyl-1,3-thiazol-2-yl)-2-(4-isobutylphenyl)propanamide
392. N-(5-isopropyl-1,3-thiazol-2-yl)-2-oxo-2-phenylacetamide
393. N-(5-isopropyl-1,3-thiazol-2-yl)-3-methyl-2-phenylpentanamide
394. (E, Z)-N-(5-isopropyl-1,3-thiazol-2-yl)-2-phenyl-2-butenamide
395. N-(5-isopropyl-1,3-thiazol-2-yl)bicyclo[4.2.0]octa-1,3,5-triene-7-carboxamide
396. N-(5-isopropyl-1,3-thiazol-2-yl)-3-oxo-1-indanecarboxamide
397. N-(5-isopropyl-1,3-thiazol-2-yl)-2-phenyl)butanamide
398. tert-butyl (1S)-2-[(5-isopropyl-1,3-thiazol-2-yl)amino]-1-methyl-2-oxoethylcarbamate
399. tert-butyl (1S,2S)-1-{[(5-isopropyl-1,3-thiazol-2-yl)amino]carbonyl}-2-methylbutylcarbamate
400. tert-butyl 2-[(5-isopropyl-1,3-thiazol-2-yl)amino]-2-oxoethylcarbamate
401. tert-butyl (1S)-5-amino-1-{[(5-isopropyl-1,3-thiazol-2-yl)amino]carbonyl}pentylcarbamate
402. tert-butyl 4-[(imino{[(4-methylphenyl)sulfonyl]amino}methyl)amino]-1-{[(5-isopropyl-1,3-thiazol-yl)amino]carbonyl}butylcarbamate
403. tert-butyl 1-{[(5-isopropyl-1,3-thiazol-2-yl)amino]carbonyl}-3-(tritylamino)propylcarbamate
404. tert-butyl (1S)-1-(benzyloxymethyl)-2-[(5-isopropyl-1,3-thiazol-2-yl)amino]-2-oxoethylcarbamate
405. tert-butyl (1S)-1-benzyl-2-[(5-isopropyl-1,3-thiazol-2-yl)amino]-2-oxoethylcarbamate
406. tert-butyl (1R)-2-[(5-isopropyl-1,3-thiazol-2-yl)amino]-2-oxo-1-(benzylthiomethyl)ethylcarbamate
407. benzyl (3S)-3-[(tert-butoxycarbonyl)amino]-4-[(5-isopropyl-1,3-thiazol-2-yl) amino]-4-oxobutanoate
408. tert-butyl (2S)-2-{[(5-isopropyl-1,3-thiazol-2-yl)amino]carbonyl}-1-pyrrolidinecarboxylate
409. tert-butyl (1S)-1-(1H-indol-3-ylmethyl)-2-[(5-isopropyl-1,3-thiazol-2-yl) amino]-2-oxoethylcarbamate 410. tert-butyl (1S)-1-([(5-isopropyl-1,3-thiazol-2-yl)amino]carbonyl}-3-(methylsulfanyl)propylcarbamate
411. tert-butyl (1S)-2-benzyloxy-1-{[(5-isopropyl-1,3-thiazol-2-yl)amino]carbonyl}propylcarbamate
412. tert-butyl (1S)-1-(4-benzyloxybenzyl)-2-[(5-isopropyl-1,3-thiazol-2-yl) amino]-2-oxoethylcarbamate
413. tert-butyl (1S)-1-{[(5-isopropyl-1,3-thiazol-2-yl)amino]carbonyl}-2-methylpropylcarbamate
414. tert-butyl (1S)-1-{[(5-isopropyl-1,3-thiazol-2-yl)amino]carbonyl}-3-methylbutylcarbamate
415. benzyl (4S)-4-[(tert-butoxycarbonyl)amino]-5-[(5-isopropyl-1,3-thiazol-2-yl)amino]-5-oxopentanoate;

and the pharmaceutically acceptable salts thereof.

The compounds of formula (I) object of the present invention and the salts thereof can be obtained, for instance, by a process comprising reacting a compound of formula (II)

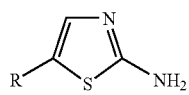
(II)

with a compound of formula (III)

(III)

wherein R and $R_1$ are as defined above and X is hydroxy or a suitable leaving group;

and, if desired, converting a 2-amino-1,3-thiazole derivative of formula (I) into another such derivative of formula (I), and/or into a salt thereof.

Examples of specific compounds of formula (III) wherein X is a suitable leaving group are those wherein X represents a halogen atom, preferably chlorine or bromine.

It is clear to the man skilled in the art that if the compound of formula (I), prepared according to the above process is obtained as an admixture of isomers, its separation into the single isomers according to conventional techniques is still within the scope of the present invention. Likewise, the conversion into the free compound (I) of a corresponding salt thereof, according to well-known procedures in the art, is still within the scope of the invention.

The above process is an analogy process which can be carried out according to well known methods. The reaction between a compound of formula (II) and a carboxylic acid of formula (III) wherein X is a hydroxy group, can be carried out in the presence of a coupling agent or a polymer supported coupling agent such as, for instance, carbodiimide, i.e. 1,3-dicyclohexylcarbodiimide, 1,3-diisopropylcarbodiimide, 1-(3-dimethylaminopropyl)-3-ethylcarbodiimide, or N-Cyclohexylcarbodiimide N'-methylpolystyrene in a suitable solvent such as, for instance, dichloromethane, chloroform, tetrahydrofuran, diethyl ether, 1,4-dioxane, acetonitrile, toluene, or N,N-dimethylformamide at a temperature ranging from about –10° C. to reflux for a suitable time, i.e. from about 30 min. to about 96 hours. The reaction between a compound of formula (II) and a compound of formula (III) can be also carried out, for example, by a mixed anhydride method, using an alkyl chloroformate, such as ethyl, iso-butyl, or iso-propyl chloroformate, in the presence of a tertiary base, such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about –30° C. to room temperature. The reaction between a compound of formula (II) and a carboxylic acid derivative of formula (III) wherein X is a suitable leaving group can be carried out in the presence of a tertiary base, such as triethylamine, N,N-diisopropylethylamine or pyridine, in a suitable solvent, such as toluene, dichloromethane, chloroform, diethyl ether, tetrahydrofuran, acetonitrile, or N,N-dimethylformamide, at a temperature ranging from about 10° C. to reflux.

Also the optional conversion of a compound of formula (I) into another compound of formula (I) can be carried out according to known methods. As an example, the nitro group of a compound of formula (I) may be converted into an amino group by treatment, for example, with stannous chloride in concentrated hydrochloric acid and by using, if necessary, an organic solvent such as acetic acid, 1,4-dioxane and tetrahydrofuran, at a temperature varying between room temperature and about 100° C. Likewise, an alkylthio or an arylthio group may be converted into the corresponding alkylsulfonyl and arylsulfonyl group by reaction, for example, with mchloroperbenzoic acid in a suitable solvent such as dichloromethane or chloroform, at a temperature varying between about –5° C. and room temperature. The optional salification of a compound of formula (I) or the conversion of a salt into the free compound as well as the separation of a mixture of isomers into the single isomers may be carried out by conventional methods.

The compounds of formula (II) and (III) according to the process object of the present invention are known compounds or can be obtained according to known methods.

For example, a compound of formula (II) wherein R is as defined above can be obtained by reacting a compound of formula (IV)

(IV)

wherein Z is a bromine or chlorine atom, with thiourea in a suitable solvent such as methanol, ethanol, tetrahydrofuran, 1,4-dioxane or toluene, at a temperature varying between room temperature and reflux, for a suitable time ranging from about 1 hour to about 24 hours. A compound of formula (III) wherein X is a leaving group as defined above can be obtained according to conventional techniques from the corresponding carboxylic acids of formula (III) wherein X is hydroxy. When preparing the compounds of formula (I) according to the process object of the present invention, optional functional groups within both the starting materials or the intermediates thereof, which could give rise to unwanted side reactions, need to be properly protected according to conventional techniques. Likewise, the conversion of these latter into the free deprotected compounds may be carried out according to known procedures.

Pharmacology

The compounds of formula (I) are active as cdk/cyclin inhibitors as they gave positive results when tested according to the following procedure.

The inhibiting activity of putative cdk/cyclin inhibitors and the potency of selected compounds was determined through a method of assay based on the use of the Multi-Screen-PH 96 well plate (Millipore), in which a phosphocellulose filter paper was placed at each well bottom allowing binding of positive charged substrate after a washing/filtration step.

When a radioactivity labelled phosphate moiety was transferred by the ser/threo kinase to the filter-bound histone, light emitted was measured in a scintillation counter. The inhibition assay of cdk2/Cyclin A activity was performed according to the following protocol:

Kinase reaction: 1.5 µM histone H1 substrate, 25 µM ATP (0.5 µCi $P^{33}\gamma$-ATP), 30 ng Cyclin A/cdk2 complex, 10 µM 10 inhibitor in a final volume of 100 µl buffer (TRIS HCl 10 mM pH 7.5, $MgCl_2$ 10 mM, 7.5 mM DTT) were added to each well of a 96 U bottom well plate. After 10 min at 37° C. incubation, reaction was stopped by 20 µl EDTA 120 mM.

Capture: 100 µl were transferred from each well to MultiScreen plate, to allow substrate binding to phosphocellulose filter. Plates were then washed 3 times with 150 µl/well PBS $Ca^{++}/Mg^{++}$ free and filtered by MultiScreen filtration system.

Detection: filters were allowed to dry at 37° C., then 100 µl/well scintillant were added and $^{33}P$ labelled histone H1 was detected by radioactivity counting in the Top-Count instrument.

Results: data were analysed and expressed as % inhibition referred to total activity of enzyme (=100%). All compounds showing inhibition ≧50% were further analysed in order to study and define potency (IC50) as well as the kinetic-profile of inhibitor through Ki calculation.

IC50 determination: the protocol used was the same described above, where inhibitors were tested at concentrations ranging from 0.0045 to 10 µM. Experimental data were analyzed by the computer program GraphPad Prizm.

Ki calculation: either the concentration of ATP and histone H1 substrate were varied: 4, 8, 12, 24, 48 µM for ATP (containing proportionally diluted $P^{13}\gamma$-ATP) and 0.4, 0.8, 1.2, 2.4, 4.8 µM for histone were used in absence and presence of two different, properly chosen inhibitor concentrations. Experimental data were analysed by the computer program SigmaPlot for Ki determination, using a random bireactant system equation:

$$v = \frac{V_{max} \frac{(A)(B)}{aK_AK_B}}{1 + \frac{(A)}{K_A} + \frac{(B)}{K_B} + \frac{(A)(B)}{aK_AK_B}}$$

where A=ATP and B=histone H1.

Following the method above described, a representative compound of formula (I) of the invention, which is 2-[4-(dimethylamino)phenyl]-N-(5-isopropyl-1,3-thiazol-2-yl) acetamide, showed an inhibiting activity towards the cdk2/cyclin A complex corresponding to 0.1 µM (Ki).

In addition, the inhibiting activity of putative cdk/cyclin inhibitors and the potency of selected compounds was determined through a method of assay based on the use of a SPA (Scintillation Proximity Assay) 96 well plate assay. The assay is based on the ability of streptavidin coated SPA beads to capture a biotinylated peptide derived from a phosphorylation site of histone. When a radioactivity labelled phosphate moiety was transferred by the ser/threo kinase to the biotinylated histone peptide, light emitted was measured in a scintillation counter. The inhibition assay of cdk5/p25 activity was performed according to the following protocol:

Kinase reaction: 1.0 µM biotinylated histone peptide substrate, 0.25 uCi P33g-ATP, 4 nM cdk2/p25 complex, 0–100 µM inhibitor in a final volume of 100 µl buffer (Hepes 20 mM pH 7.5, MgCl2 15 mM, 1 mM DTT) were added to each well of a 96 U bottom well plate. After 20 min at 37° C. incubation, the reaction was stopped by the addition of 500 ug SPA beads in phosphate-buffered saline containing 0.1% Triton X-100, 50 uM ATP and 5 mM EDTA. The beads were allowed to settle, and the radioactivity incorporated in the 33P-labelled peptide was detected in a Top Count scintillation counter.

Results: Data were analyzed and expressed as % Inhibition using the formula:

100×(1−(Unknown−Bkgd)/(Enz. Control−Bkgd))

IC50 values were calculated using a variation of the four parameter logistics equation:

$Y=100/[1+10^{((LogEC50-X)*Slope)}]$

Where X=log(uM) and Y % Inhibition.

The compounds of formula (I) are therefore useful to restrict the unregulated proliferation of tumor cells, hence in therapy in the treatment of various tumors such as, for instance, carcinomas, e.g. mammary carcinoma, lung carcinoma, bladder carcinoma, colon carcinoma, ovary and endometrial tumors, sarcomas, e.g. soft tissue and bone sarcomas, and the hematological malignancies such as, e.g., leukemias. In addition, the compounds of formula (I) are also useful in the treatment of other cell proliferative disorders such as psoriasis, vascular smooth cell proliferation associated with atherosclerosis and post-surgical stenosis and restenosis and in the treatment of Alzheimer's disease.

The compounds of the present invention can be administered either as single agents or, alternatively, in combination with known anticancer treatments such as radiation therapy or chemotherapy regimen in combination with cytostatic or cytotoxic agents. As an example, the above compounds can be administered in combination with one or more chemotherapeutic agents such as, for instance, taxane, taxane derivatives, CPT-11, camptothecin derivatives, anthracycline glycosides, e.g. doxorubicin or epirubicin, etoposide, navelbine, vinblastine, carboplatin, cisplatin and the like, optionally within liposomal formulations thereof.

The compounds of formula (I) of the present invention, suitable for administration to a mammal, e.g. to humans, can be administered by the usual routes and the dosage level depends upon the age, weight, conditions of the patient and the administration route. For example, a suitable dosage adopted for oral administration of a compound of formula (I) may range from about 10 to about 500 mg pro dose, from 1 to 5 times daily.

The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous and/or intrathecal and/or intraspinal injection or infusion.

The present invention also includes pharmaceutical compositions comprising a compound of formula (I), or a pharmaceutically acceptable salt thereof, in association with a pharmaceutically acceptable excipient (which can be a carrier or a diluent). The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic acid, magnesium or calcium stearate, and/or polyethylene glycols; binding agents, e.g. starches, arabic gum, gelatine, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes. The liquid dispersions for oral administration may be e.g. syrups, emulsions and suspensions. The syrups may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as carrier, for example, sterile water or preferably they may be in the form of sterile, aqueous, isotonic saline solutions or they may contain as a carrier propylene glycol. The suppositories may contain together with the active compound a pharmaceutically acceptable carrier, e.g. cocoa butter, polyethylene glycol, a polyoxyethylene sorbitan fatty acid ester surfactant or lecithin.

The following examples illustrate but do not limit the present invention.

EXAMPLE 1

Preparation of Ethyl 3-[(5-bromo-1,3-thiazol-2-yl) amino]-3-oxopropanoate

Ethyl malonyl chloride (0.88 ml; 6.99 mmol) was added to a mixture of 2-amino-5-bromothiazole hydrobromide (1.30 g; 5.00 mmol) and Et3N (2.08 ml; 14.94 mmol) in THF (6 ml) at 0–5° C. The mixture was stirred at room temperature overnight, then the reaction was quenched with potassium sarcosinate (0.25 g; 2.00 mmol) and water (12 ml). The product was isolated by filtration as a white solid (0.75 g, 51%): m.p. 165–166° C.

$^1$H-NMR (CDCl$_3$) δ ppm: 10.80 (bs, 1H, CONH); 7.38 (s, 1H, thiazole CH); 4.28 (q, J=7.3 Hz, 2H, COOCH2CH3); 3.56 (s, 2H, COCH2CO); 1.32 (t, J=7.3 Hz, 2H, COOCH2CH3).

Analogously, the following products can be prepared:
N-(5-bromo-1,3-thiazol-2-yl)-2-phenyl-acetamide
 m.p. 206–207° C.
 $^1$H.NMR (DMSO-D) δ ppm: 3.76 (s, 2H, COCH2Ph); 7.2–7.3 (m, 5H, Ph); 7.54 (s, 1H, thiazole CH); 12.80 (bs, 1H, CONH);
N-(5-bromo-1,3-thiazol-2-yl)-benzamide
 m.p. 126–128° C.
 $^1$H-NMR (DMSO-d$_6$) δ ppm: 12.90 (bs, 1H, CONH); 8.07, 7.93 (m, 2H, o-Ph hydrogens); 7.63 (s, 1H, thiazole CH); 7.62, 7.53, 7.48 (m, 3H, m- and p-Ph hydrogens);
Ethyl 4-[(5-bromo-1,3-thiazol-2-yl)amino]-4-oxobutanoate.

EXAMPLE 2

Preparation of
N-(5-Bromo-thiazol-2-yl)-3-hydroxypropionamide

A mixture of LiBH4 (44 mg, 2.02 mmol), ethyl 3-[(5-bromo-1,3-thiazol-2-yl)amino]-3-oxopropanoate (340 mg, 1.16 mmol), ethanol (0.082 ml, 2.02 mmol), and Et2O (50 ml) was refluxed for 20 min. The reaction was quenched with 1 N hydrochloric acid with ice-cooling. The mixture was then diluted with water and extracted with dichloromethane. The extract was dried and the solvent was evaporated under reduced pressure. Purification by silica gel chromatography (dichloromethane/methanol=98:2 and then 95:5) yielded the title compound as a white solid (0.17 g; 52%).

m.p. 182–184° C. (dec.)
$^1$H-NMR (CDCl$_3$) δ ppm: 10.20 (bs, 1H, CONH); 7.35 (s, 1H, thiazole CH); 4.04 (t, J=5.4 Hz, 2H, COCH2CH2OH); 2.74 (t, J=5.4 Hz, 2H, COCH2CH$_2$OH).

Analogously, starting from the corresponding ester derivative the following product can be prepared:
N-(5-Bromo-1,3-thiazol-2-yl)-4-hydroxybutanamide.

EXAMPLE 3

Preparation of
N-(5-Bromo-thiazol-2-yl)-2-ethoxy-acetamide

EDCI (0.53 g, 2.78 mmol) was added to a solution of ethoxyacetic acid (0.29 g, 2.78 mmol) in CH2Cl2 (5 ml) under ice-cooling. After stirring for 1 h, a solution of 2-amino-5-bromothiazole hydrobromide (0.60 g, 2.31 mmol) and diisopropylethylamine (0.40 ml, 2.34 mmol) in CH2Cl2 (5 ml) was added dropwise, and the entire mixture was kept at 0° C. for 1 h, then at room temperature overnight. The solution was evaporated and the residue partitioned between ethyl acetate and water. The ethyl acetate layer was further washed with water, 5% citric acid, water, saturated sodium bicarbonate, and water. Drying over sodium sulfate and evaporation gave a solid which was triturated with isopropyl ether to give the title compound as a beige solid (0.43 g; 70%)

m.p. 100–102° C.
$^1$H-NMR (CDCl$_3$) δ ppm: 9.64 (bs, 1H, CONH); 7.38 (s, 1H, thiazole CH); 4.16 (s, 2H, COCH2O); 3.65 (q, J=6.8 Hz, 2H, OCH2CH3); 1.29 (t, J=6.8 Hz, 3H, OCH2CH3).

Analogously, the following products can be prepared:
tert-butyl 3-[(5-bromo-1,3-thiazol-2-yl)amino]-3-oxopropylcarbamate;
Benzyl 4-[(5-bromo-1,3-thiazol-2-yl)amino]-4-oxobutylcarbamate;
tert-butyl 4-{2-[(5-isopropyl-1,3-thiazol-2-yl)amino]-2-oxoethyl}phenylcarbamate
tert-butyl 4-{[(5-isopropyl-1,3-thiazol-2-yl)amino] carbonyl}phenylcarbamate
tert-butyl 4-{2-[(5-isopropyl-1,3-thiazol-2-yl)amino]-2-oxoethyl}-1,3-thiazol-2-ylcarbamate;
N-(5-bromo-1,3-thiazol-2-yl)-2-bromoacetamide;
N-(5-isopropyl-1,3-thiazol-2-yl)-2-bromoacetamide;
2-N-[2-(3-pyridyl)-acetyl-amino]-5-bromo-thiazole
 m.p. 232–235° C.
 $^1$H-NMR (DMSO-d$_6$): 3.82 (s, 2H, COCH2Ph); 7.34 (dd, J=4.4, 7.7 Hz, 1H, H5 Py); 7.55 (s, 1H, thiazole CH); 7.71 (ddd, J=1.6, 2.2, 7.7 Hz, 1H, H4 Py); 8.45 (dd, J=1.6, 4.9 Hz, 1H, H6 Py); 8.49 (d, J=2.2 Hz, 1H, H2 Py); 12.65 (s, 1H, CONH);

2-N-[2-(3-pyridyl)-acetyl-amino]-5-isopropyl-thiazole
m.p. 178–180° C. (dec.)
¹H-NMR (DMSO–d₆) δ ppm: 12.20 (bs, 1H, CONH); 8.45, 7.7, 7.35 (m, 4H, Py); 7.17 (s, 1H, thiazole CH); 3.78 (s, 2H, COCH2); 3.14 (m, 1H, CHMe₂); 1.22 (d, 6H, CHMe₂);

N-(5-bromo-1,3-thiazol-2-yl)-2-(3-hydroxyphenyl) acetamide;

N-(5-isopropyl-1,3-thiazol-2-yl)-2-(3-hydroxyphenyl)acetamide
m.p. 206–208° C.
¹H-NMR (DMSO–d₆) δ ppm: 12.1 (bs, 1H, CONH); 9.34 (s, 1H, OH); 7.14 (s, 1H, thiazole CH); 7.1 (t, 1H, H5 Ph); 6.6—6.7 (m, 3H, 2H, h4, H6, Ph); 3.6 (s, 2H, COH₂); 3.08 (ept, 1H CHMe₂); 1.22 (d, 6H, CHMe₂);

N-(5-bromo-1,3-thiazol-2-yl)-2-(3-methoxyphenyl) acetamide;

N-(5-isopropyl-1,3-thiazol-2-yl)-2-(3-methoxyphenyl)acetamide
m.p. 97–98° C.
¹H-NMR (DMSO–d₆) δ ppm: 12.12 (s, 1H, CONH); 7.21 (dd, 1H, H5 Ph); 7.14 (d, 1H, thiazole CH); 6.87 (m, 2H, H2, H6 Ph); 6.81 (ddd, 1H, H4 Ph); 3.72 (s, 3H, OMe); 3.67 (s, 2H, COCH₂); 3.07 (m, 1H, CHMe₂); 1.22 (d, 6H, CHMe₂);

N-(5-bromo-1,3-thiazol-2-yl)-2-(3-chorophenyl)acetamide;

N-(5-isopropyl-1,3-thiazol-2-yl)-2-(3-chorophenyl)acetamide
m.p. 116–118° C.
¹H-NMR (CDCl₃) δ ppm: 11.8 (bs, 1H, CONH); 7.32 (s, 1H, H2 Ph); 7.24 (m, 3H, H4, H5, H6 Ph); 7.04 (s, 1H, thiazole CH); 3.76 (s, 2H, COCH₂); 3.13 (m, 1H, CHMe₂); 1.31 (d, 6H, CHMe₂);

N-(5-bromo-1,3-thiazol-2-yl)-2-(4-hydroxyphenyl)acetamide;

N-(5-isopropyl-1,3-thiazol-2-yl)-2-(4-hydroxyphenyl)acetamide
¹H-NMR (DMSO–d₆) δ ppm: 12.07 (bs, 1H, CONH); 9.33 (sb, 1H, OH); 7.17–6.7 (m, 5H, Ar+ CHthiazole); 3.60 (s, 2H, COCH₂) 3.1 (m, 1H, CHMe₂); 1.23 (d, 6H, CHMe₂)

N-(5-bromo-1,3-thiazol-2-yl)-2-(3,4-dihydroxyphenyl)acetamide;

N-(5-isopropyl-1,3-thiazol-2-yl)-2-(3,4-dihydroxyphenyl) acetamide
m.p. 168–169° C.
¹H-NMR (DMSO–d₆) δ ppm: 12.01 (bs, 1H, CONH); 8.79 (sb, 2H, 2 OH); 7.12 (s, 1H, thiazole CH); 6.69 (d, 1H, H2 Ph); 6.63 (d, 1H, H5 Ph); 6.52 (dd, 1H, H6 Ph); 3.48 (s, 2H, COCH₂) 3.06 (m, 1H, CHMe₂); 1.22 (d, 6H, CHMe₂);

N-(5-bromo-1,3-thiazol-2-yl)-2-(4-hydroxy-3-methoxyphenyl)acetamide;

N-(5-isopropyl-1,3-thiazol-2-yl)-2-(4-hydroxy-3-methoxyphenyl)acetamide
m.p. 115–116° C.
¹H-NMR (DMSO–d₆) δ ppm: 12.0 (bs, 1H, CONH); 8.80 (s, 1H, OH); 7.12 (d, 1H, thiazole CH); 6.88 (s, 1H, H2 Ph); 6.68 (m, 2H, H5, H6 Ph); 3.73 (s, 3H, OMe); 3.56 (s, 2H, COCH₂) 3.07 (m, 1H, CHMe₂); 1.22 (d, 6H, CHMe₂)

N-(5-bromo-1,3-thiazol-2-yl)-2-(4-methoxyphenyl)acetamide;

N-(5-isopropyl-1,3-thiazol-2-yl)-2-(4-methoxyphenyl)acetamide
m.p. 129–130° C.
¹H-NMR (DMSO–d₆) δ ppm: 12.08 (s, 1H, CONH); 7.21 (dd, 2H, H2, H6 Ph); 7.13 (d, 1H, thiazole CH); 6.87 (dd, 2H, H3, H5 Ph); 3.70 (s, 3H, OMe); 3.62 (s, 2H, COCH); 3.06 (m, 1H, CHMe₂); 1.22 (d, 6H, CHMe₂);

N-(5-isopropyl-1,3-thiazol-2-yl)-2-phenyl-acetamide
m.p. 135–137° C.
¹H-NMR (DMSO–d₆) δ ppm: 12.20 (bs, 1H, CONH); 7.29 (m, 5H, Ph); 7.13 (s, 1H, thiazole CH); 3.70 (s, 2H, COCH₂); 3.07 (m, 1H, CHMe₂); 1.22 (d, 6H, CHMe₂);

2-[3-(3-chloropropoxy)pheny]-N-(5-isopropyl-1,3-thiazol-2-yl)acetamide
m.p. 91–92° C.
¹H-NMR (DMSO–d₆) δ ppm: 12.08 (bs, 1H, CONH); 7.21 (t, 1H, H5 Ph); 7.13 (s, 1H, thiazole CH); 6.8–6.9 (m, 3H, H2, H4, H6 Ph); 4.05 (t, 2H, OCH₂CH₂CH₂Cl); 3.77 (t, 2H, OCH₂CH₂CH₂Cl) 3.67 (s, 2H, COCH₂); 3.07 (ept, 1H, CHMe₂); 2.14 (quint, 2H, OCH₂CH₂CH₂Cl); 1.22 (d, 6H, CHMe₂); and 2-[3-(2-chloroethoxy)phenyl]-N-(5-isopropyl-1,3-thiazol-2-yl)acetamide
m.p. 134–135° C.
¹H-NMR (DMSO–d₆) δ ppm: 12.09 (bs, 1H, CONH); 7.22 (t, 1H, H5 Ph); 7.13 (s, 1H, thiazole CH); 6.8–6.9 (m, 3H, H2, H4, H6 Ph); 4.2 (t, 2H, OCH₁CH₂Cl); 3.91 (t, 2H, OCH₂CH₂Cl); 3.67 (s, 2H, COCH₂); 3.07 (ept, 1H, CHMe₂); 1.22 (d, 6H, CHMe₂)

EXAMPLE 4

Preparation of
N-(5-bromo-thiazol-2-yl)-4-sulfamoylbenzamide

To a mixture of 4-sulfamoylbenzoic acid (1.0 g, 4.97 mmol), Et3N (1.5 ml, 10.78 mmol), DMF (5 ml) and THF (5 ml) isobutyl choroformate (0.70 ml, 5.36 mmol) was added dropwise at –10° C. After stirring for 1 h, a solution of 2-amino-5-bromothiazole hydrobromide (1,55 g, 5.96=mol) and Et3N (0.83 ml, 5.96 mmol) in DMF (6 ml) and THF (4 ml) was added dropwise to the mixture at the same temperature.

The resulting mixture was gradually warmed to room temperature over a period of 3 h and then concentrated by evaporation of the solvent in vacuo. To the resultant residue AcOEt and 5% aqueous NaHCO3 were added. The separated organic phase was washed with water, dried over anhydrous Na2SO4, and concentrated under reduced pressure. The residual solid was purified by flash cromatography (dichloromethane/methanol/30% aqueous ammonia=95:5: 0.5) to afford the title compound as a yellow solid (0.77 g, 43%)
m.p. 268–270° C.
¹H-NMR (DMSO-d) δ ppm: 7.54 (s, 2H, SO2NH2); 7.67 (s, 1H, thiazole CH); 7.94 (d, J=8.8 Hz, 2H, H3 and H5 Ph); 8.21 (d, J=8.8 Hz, 2H, H2 and H6 Ph); 13.10 (bs, 1H, CONH).

Analogously, the following product can be prepared:
N-(5-isopropyl-thiazol-2-yl)-4-sulfamoyl-benzamide
m.p. 222–224° C.
¹H-NMR (DMSO–d₆) δ ppm: 12.65 (bs, 1H, CONH); 8.18 (dd, 2H, H2, H6 Ph); 7.92 (dd, 2H, H3, H5 Ph); 7.51 (s, 2H, SO₂NH₂); 7.25 (s, 1H, thiazole CH); 3.13 (m, 1H, CHMe₂); 1.28 (d, 6H, CHMe₂).

EXAMPLE 5

Preparation of
4-amino-N-(5-bromo-1,3-thiazol-2-yl)butanamide hydrobromide

A solution (1.3 ml) of hydrogen bromide in glacial acetic acid (33%) was added to benzyl 4-[(5-bromo-1,3-thiazol-2- yl)amino]-3-oxobutylcarbamate (0.72 g, 1.81 mmol) and the mixture was stirred at room temperature for 1 h.

Ether was added and the solid was filtered and washed with ether. The crude product was recrystallized from MeOH/ether to afford the title compound as a beige solid (0.38 g, 61%), m.p. 211–213° C. (dec.)

$^1$H-NMR (DMSO-$d_6$) δ ppm: 1.84 (m, 2H, COCH2CH2CH2NH2); 2.53 (t, J=6.8 Hz, 2H, COCH2CH2CH2NH2); 2.81 (m, 2H, COCH2CH2CH2NH2); 7.68 (bs, 3H, NH3+); 12.42 (s, 1H, CONH)

EXAMPLE 6

Preparation of 3-amino-N-(5-bromo-1,3-thiazol-2-yl)propionamide hydrochloride A solution 3.6 N HCl in isopropanol (14 ml) was added to tert-butyl 3-[(5-bromo-1,3-thiazol-2-yl)amino]-4-oxopropylcarbamte (0.90 g, 2.57 mmol) and the mixture was stirred at room temperature overnight. The solvent was evaporated and the residual solid was triturated in ether, filtered and dried in vacuo to afford the title compound as a white solid (0.73 g, quantitative yield)

m.p. 255° C. ca.(dec.)

$^1$H-NMR (DMSO-$d_6$) δ ppm: 2.83 (t, J=6.8 Hz, 2H, COCH$_2$CH$_2$NH$_2$); 3.07 (q, J=6.4 Hz, 2H, COCH$_2$CH$_2$NH$_2$); 7.55 (s, 1H, thiazole CH); 7.96 (bs, 3H, NH3+); 12.58 (s, 1H, CONH).

Analogously, the following compounds can be prepared:
2-(4-aminophenyl)-N-(5-isopropyl-1,3-thiazol-2-yl)acetamide $^1$H-NMR (DMSO-$d_6$) δ ppm: 1.22 (d, 6H, CHMe$_2$); 3.07 (m, 1H, CHMe$_2$); 3.47 (s, 2H, COCH$_2$); 4.94 (s, 2H, NH$_2$); 6.48 (m, 2H, H3, H5 Ph); 6.93 (m, 2H, H2, H6 Ph); 7.12 (d, 1H, CH thiazole); 12.00 (s, 1H, CONH).

4-amino-N-(5-isopropyl-1,3-thiazol-2-yl)benzamide $^1$H-NMR (DMSO-$d_6$) δ ppm: 1.29 (d, 6H, CHMe$_2$); 3.12 (m, 1H, CHMe$_2$); 6.58 (m, 2H, H3, H5 Ph); 7.18 (d, 1H, CH thiazole) 7.82 (m, 2H, H2, H6 Ph); 12.80 (bs, 1H, CONH).

2-(2-amino-1,3-thiazol-4-yl)-N-(5-isopropyl-1,3-thiazol-2-yl)acetamide m.p. 204–206° C. ca.(dec.)

$^1$H-NMR (DMSO-$d_6$) δ ppm: 1.24 (d, 6H, CHMe$_2$); 3.10 (m, 1H, CHMe$_2$); 3.54 (s, 2H, COCH$_2$); 6.30 (s, 1H, H5 thiazole); 6.88 (s, 2h, NH$_2$); 7.13 (s, 1H, H4 thiazole); 11.90 (s, 1H, ONH).

EXAMPLE 7

Preparation of N-(5-isopropyl-1,3-thiazol-2-yl)-butanamide

Triethylamine (0.97 ml; 6.34 mmol) and butanoyl chloride (0.52 ml; 5.07 mmol) were added in this order to a solution of 2-amino-5-isopropyl-1,3-thiazole (0.6 g; 4.23 mmol) in dichloromethane (8 ml), cooled to −5° C. The reaction mixture was stirred at −5° C. for 2 hours and then warmed to room temperature. After additional 4 hours, the organic layer was washed with water, saturated sodium bicarbonate, 1N hydrochloric acid, brine, dried over sodium sulfate and evaporated. The residue was recrystallized from cyclohexane to yield 0.45 g (50%) of the title compound as a colourless solid (m.p. 95–97° C.)

$^1$H-NMR (DMSO-$d_6$) δ ppm: 11.82 (s, 1H, CONH); 7.11 (s, 1H, thiazole CH); 3.08 (m, 1H, CHMe2); 2.34 (t, J=7.1 Hz, 2H, COCH2CH2CH3); 1.58 (m, 2H, COCH2CH2CH3); 1.23 (d, J=6.6 Hz, 6H, (CH3)$_2$CH); 0.87 (t, J=7.1 Hz, 3H, COCH2CH2CH3).

Analogously, the following compounds can be prepared:
N-(5-bromo-1,3-thiazol-2-yl)-butanamide
  m.p. 163–164° C.
  $^1$H-NMR (DMSO-$d_6$) δ ppm: 12.27 (bs, 1H, CONH); 7.50 (s, 1H, thiazole CH); 2.39 (t, 2H, COCH2CH2CH3); 1.59 (m, 2H, COCH2CH2CH3); 0.87 (t, 3H, COCH2CH2CH3);

N-(5-chloro-1,3-thiazol-2-yl)-butanamide
  m.p. 170–171° C.
  $^1$H-NMR (DMSO-$d_6$) δ ppm: 12.25 (bs, 1H, CONH); 7.46 (s, 1H, thiazole CH); 2.38 (t, 2H, COCH2CH2CH3); 1.59 (m, 2H, COCH2CH2CH3); 0.87 (t, 3H, COCH2CH2CH3);

N-(5-phenyl-1,3-thiazol-2-yl)-butanamide
  m.p. 183–184° C.
  $^1$H-NMR (DMSO-$d_6$) δ ppm: 12.13 (s, 1H, CONH), 7.84 (s, 1H, thiazole CH); 7.58 (d, J=6.8 Hz, 2H, o-Ph hydrogens); 7.39 (dd, J 6.8 and 7.8 Hz, 2H, m-Ph hydrogens); 7.28 (t, J=7.8 Hz, 1H, p-Ph hydrogens); 2.41 (t, J=7.3 Hz, 2H, COCH2CH2CH3); 1.61 (m, 2H, COCH2CH2CH3); 0.89 (t, J=7.3 Hz, 3H, COCH2CH2CH3);

N-(5-nitro-1,3-thiazol-2-yl)-butanamide
  m.p. 175–176° C.
  $^1$H-NMR (DMSO-$d_6$) δ ppm: 13.02 (s, 1H, CONH); 8.60 (s, 1H, thiazole CH); 2.48 (t, J=7.3 Hz, 2H, COCH2CH2CH3); 1.62 (m, 2H, COCH2CH2CH3); 0.89 (t, J=7.3 Hz, 3H, COCH2CH2CH3);

N-(5-methyl-1,3-thiazol-2-yl)-butanamide
  m.p. 137–138° C.
  $^1$H-NMR (CDCl$_3$) δ ppm: 11.89 (s, 1H, CONH); 7.04 (s, 1H, thiazole CH); 2.48 (t, J=7.3 Hz, 2H, COCH2CHCH3); 2.41 (s, 3H, CH3); 1.80 (m, 2H, COCH2CH2CH3); 1.02 (t, J=7.3 Hz, 3H, COCH2CH2CH3);

N-(5-benzyl-1,3-thiazol-2-yl)-butanamide
  m.p. 147–149° C.
  $^1$H-NMR (CDCl$_3$) δ ppm: 7.23 (m, 5H, Ph); 7.07 (s, 1H, thiazole CH); 4.08 (s, 2H, CH2Ph); 2.45 (t, J=7.8 Hz, 2H, COCH2CH2CH3); 1.76 (m, 2H, COCH2CH2CH3); 0.97 (t, J=7.8 Hz, 2H, COCH2CH2CH3);

N-(5-isobutyl-1,3-thiazol-2-yl)-butanamide
  m.p. 58–60° C.
  $^1$H-NMR (CDCl$_3$) δ ppm: 7.03 (s, 1H, thiazole CH); 2.61 (d, J=7.3 Hz, 2H, Me2CHCH2); 2.45 (t, J=7.8 Hz, 2H, COCH2CH2CH3); 1.81 (m, 1H, Me2CHCH2); 1.78 (m, 2H, COCH2CH2CH3); 1.01 (t, J=7.8 Hz, 3H, COCH2CH2CH3); 0.95, 0.93 (s, 6H, Me2CHCH2);

N-(5-cyclopropyl-1,3-thiazol-2-yl)-butanamide;
N-{5-[2-(methylsulfonyl)ethyl]-1,3-thiazol-2-yl}-butanamide
  m.p. 153–155° C.
  $^1$H-NMR (CDCl$_3$) δ ppm: 11.01 (s, 1H, CONH); 7.21 (s, 1H, thiazole CH); 3.34 (m, 4H, CH3SO2CH2CH2); 2.90 (s, 3H, H3SO$_2$); 2.48 (t, J=7.3 Hz, 2H, COCH2CH2CH3); 1.80 (m, H, COCH2CH2CH3); 1.02 (t, J=7.3 Hz, 3H, COCH2CH2CH3);

N-[5-(2-methylthioethyl)-1,3-thiazol-2-yl]-butanamide
  m.p. 67–69° C.
  $^1$H-NMR (CDCl$_3$) δ ppm: 11.63 (bs, 1H, NHCO), 7.26 (s, 1H, thiazole CH), 3.06 (t, J=7.0 Hz, 2H, CH3SCH2CH2); 2.77 (t, J=7.0 Hz, 2H, CH3SCH2CH2); 2.48 (t, J=7.3 Hz, 2H, COCH2CH2CH3); 2.14 (s, 3H, CH3S); 1.80 (m, 2H, COCH2CH2CH3); 1.02 (t, J=7.3 Hz, 3H, COCH2CH2CH3);

N-{5-[2-(methoxycarbonyl)ethyl]-1,3-thiazol-2-yl}-butanamide;

N-[5-(3-methoxy-propyl)-1,3-thiazol-2-yl]-butanamide
m.p. 80–82° C.
$^{1}$H-NMR (CDCl$_3$) δ ppm: 11 (sb, 1H, NHCO); 7.07 (s, 1H, H4 thiazole); 3.41 (t, 2H, CH$_2$CH$_2$CH$_2$OMe); 3.34 (s 3H, OCH$_3$); 2.85 (t, 2H, CH$_2$CH$_2$CH$_2$OMe); 2.46 (t, 2H, NHCOCH$_2$); 1.91 (m, 2H, CH$_2$CH$_2$CH$_2$OMe); 1.80 (t, 2H. NHCOCH$_2$CH$_2$CH$_3$); 1.01 (t, 3H, NHCOCH$_2$CH$_2$CH$_3$);

N-[5-(2-ethoxy-ethyl)-1,3-thiazol-2-yl]-butanamide
m.p. 74–76° C.
$^{1}$H-NMR (CDCl$_3$) δ ppm: 7.14 (s, 1H, H4 thiazole); 3.64 (t, 2H, CH$_2$CH$_2$OEt); 3.52 (q 2H, OCH$_2$CH$_3$); 3.02 (t, 2H, CH$_2$CH$_2$OEt); 2.47 (t, 2H, NHCOCH$_2$); 1.80 (m, 2H, NHCOCH$_2$CH$_2$); 1.23 (t, 3H. OCH$_2$CH$_3$); 1.02 (t, 3H, NHCOCH$_2$CH$_2$CH$_3$);

N-[5-(indol-3-yl-methyl)-1,3-thiazol-2-yl]-butanamide
m.p. 240–242° C.
$^{1}$H-NMR (CDCl$_3$) δ ppm: 9.95 (bs, 1H, CONH); 8.00 (bs, 1H, NH indole); 7.54 (d, 1H, H4 indole); 7.36 (d, 1H, H7 indole); 7.19 (m, 1H, H6 indole); 7.17 (s, 1H, thiazole CH); 7.09 (m, 1H, H5 indole); 7.07 (s, 1H, H2 indole); 4.23 (s, 2H, CH$_2$); 2.39 (m 2H, CH$_2$CO); 1.73 (m, 2H, CH$_2$CH$_2$); 0.96 (t, 3H, CH$_3$CH$_2$CH$_2$).

N-[5-(3-dimethylaminoimino-butyl)-1,3-thiazol-2-yl]butanamide.

EXAMPLE 8

2-amino-5-isopropyl-1,3-thiazole 2 ml (18.6 mmol) of 3-methylbutyraldehyde were dissolved in 15 ml of dioxane. 40.4 ml (18.6 mmol) of a solution 2% v/v of bromine in dioxane was dropped therein at 0° C. The mixture was maintained at room temperature under stirring for 2 hours, then 2.83 g (37.2 mmol) of thiourea and 5 ml of ethanol were added. After 6 hours at room temperature the solution was evaporated to dryness, the residue was dissolved in methylene chloride and the product extracted with 1M hydrochloric acid; the aqueous layer was made basic by using 30% ammonium hydrate and extracted again with methylene chloride. The organic phase was dried over sodium sulfate and evaporated under vacuum. The residue was chromatographed on a silica gel column, eluting with cyclohexane-ethylacetate to give 1.1 g (42% yield) of the title compound.
$^{1}$H-NMR (DMSO-D$_6$) δ ppm: 6.6 (s, 2H, NH2); 6.58 (s, 1H, thiazole CH); 2.9 (m, 1H, CHMe2); 1.18 (s, 3H, MeCHMe); 1.17 (s, 3H, MeCHMe).

Analogously the following products can be prepared starting from the suitable aldehyde:
2-amino-5-isobutyl-1,3-thiazole
$^{1}$H-NMR (DMSO-d$_6$) δ ppm: 6.61 (sb, 2H, NH2); 6.56 (s, 1H, thiazole CH); 2.39 (dd, 2H, CH$_2$CHMe$_2$); 1.65 (m, 1H, CHMe$_2$); 0.85 (d, 6H, CHMe$_2$);
2-amino-5-phenyl-1,3-thiazole;
2-amino-5-benzyl-1,3-thiazole;
$^{1}$H-NMR (DMSO-d$_6$) δ ppm: 7.3–7.2 (m, 5H, Ph); 6.68 (s, 1H, thiazole CH); 6.67 (sb, 2H, NH2); 3.87 (s, 2H, CH$_2$Ph)
2-amino-5-(3-indolylmethyl)-1,3-thiazole;
2-amino-5-ethoxyethyl-1,3-thiazole;
2-amino-5-methoxypropyl-1,3-thiazole;
2-amino-5-cyclopropyl-1,3-thiazole;
2-amino-5-methylthioethyl-1,3-thiazole;
2-amino-5-formyl-1,3-thiazole;
2-amino-5-(3-dimethylaminoimino)butyl-1,3-thiazole.

EXAMPLE 9

4-ethoxy-1-butanol 85 mg (0.004 mmol) of sodium were dissolved in 50 ml of methanol and 8.7 g (0.23 mol) of sodium borohydride were added. A solution of 4.6 g (0.032 mol) of methyl 4-ethoxybutanoate in 20 ml of methanol was dropped to the mixture under stirring. The reaction is maintained at reflux for 6 hours, then 300 ml of brine were added and the product was extracted with methylene chloride. The organic layer was dried over anhydrous sodium sulfate and evaporated to dryness to give 2.25 g (61% yield) of the title compound.

Analogously the following products can be prepared starting from the suitable ester:
2-cyclopropyl-1-ethanol;
3-(3-indolyl)-1-propanol; and
5-dimethylaminoimino-1-hexanol.

EXAMPLE 10

Methyl 3-(3-indolyl)-propanoate 2 g (10.57 mmol) of 3-indolepropionic acid were dissolved in 50 ml of methanol. The solution was cooled to 0° C. and 5 ml of sulfuric acid 96% were dropped under stirring. The solution was maintained at room temperature overnight and then poured onto ice-water, basified with 30% ammonium hydrate and finally extracted with methylene chloride. The organic layer was dried over anhydrous sodium sulfate and evaporated to dryness to give 2.3 g of an oily product (93% yield).

Analogously the following products can be prepared starting 35 from the suitable carboxylic acid:
Methyl 4-ethoxy butanoate;
Methyl cyclopropylacetate; and
5-methoxycarbonylethyl-2-amino-1,3-thiazole.

EXAMPLE 11

4-methyl-pentanal 1.24 ml (14.18 mmol) of oxalyl chloride were dissolved in 10 ml of methylene chloride and after cooling to −60° C., 2.31 ml of DMSO (35 mmoles) were dropped. After 5 minutes at the same temperature, a solution of 1 ml (11.9 mmol) of 4-methyl-1-pentanol in 10 ml of methylene chloride was slowly dropped. The mixture was maintained under stirring for 30 minutes at the same temperature, then 8.3 ml (59.5 mmol) of triethylamine were added. After 2 hours at 0° C. water was added. The mixture was diluted with methylene chloride and washed successively with 1M hydrochloric acid, water, saturated sodium bicarbonate and finally with brine. The organic layer was dried over anhydrous sodium sulfate and evaporated to dryness to give 0.7 g (25% yield) of the title compound.

Analogously the following products can be prepared starting from the suitable alcohol:
2-cyclopropyl-1-ethanal;
4-methylthio-1-butanal;
4-ethoxy-1-butanal;
5-methoxy-1-pentanal; and
5-dimethylaminoimino-1-hexanal.

EXAMPLE 12

5-benzyloxy-1-methoxy-pentane 1.6 g (0.039 mol) of 55% sodium hydride in oil were added to 50 ml of dimethylformamide under stirring at room temperature. 5 ml (0.026 mol) of 5-benzyloxy-1-pentanol and 2.43 ml (0.039 mol) of methyl iodide were then added successively. After a night the excess of sodium hydride was decomposed with water and the solvent evaporated under vacuum. The residue was redissolved with methylene chloride and washed with water. The organic layer was finally dried over anhydrous sodium sulfate and evaporated to give 3.5 g (70% yield) of the title compound.

Analogously, by using ethyl iodide, the following compound can be prepared:
4-ethoxy-butanoic acid.

EXAMPLE 13

5-methoxy-1-pentanol 3.5 g (0.018 mol) of 5-benzyloxy-1-methoxy-pentane were dissolved in 50 ml of ethanol and 400 mg of 10% palladium on activated charcoal were added. The mixture was hydrogenated at 40 psi at room temperature for 5 hours, then filtered on celite and evaporated under vacuum to give 1.77 g (84% yield) of the title compound.

EXAMPLE 14

15 Ethyl 5-dimethylaminoimino-hexanoate 15.8 g (100 mmol) of ethyl 4-acetyl-butanoate and 6 g (100 mmol) of anhydrous N,N-dimethyl hydrazine in 50 ml of toluene containing 0.1 ml of trifluoroacetic acid were heated at 70° C. for 5 hours. The mixture was then washed 20 with water, dried over anhydrous sodium sulfate and evaporated to give 12.3 g (79% yield) of the title compound.

EXAMPLE 15

25 N-[5-(3-oxo-butyl)-1,3-thiazol-2-yl]-butanamide

To a stirred solution of 200 mg (1 mmol) of cupric acetate in 10 ml of water 141 mg (0.5 mmol) of N-[5-(3-dimethylaminoimino-butyl)-1,3-thiazol-2-yl]-butanamide in 10 ml of tetrahydrofuran were added. After 2 hours the solvent was removed under reduced pressure, a mixture of aqueous ammonium chloride and ammonium hydroxide was added and the product extracted with methylene chloride to give after drying and concentration 114 mg (95% yield) of the title compound.

EXAMPLE 16

2-benzyloxycarbonylamino-5-formyl-1,3-thiazole 1 g (7.8 mmol) of 2-amino-5-formyl-1,3-thiazole was dissolved in 25 ml of tetrahydrofuran and 1.35 ml (9.36mmol) of triethylamine and 1.33 ml (9.36 mmol) of benzylchloroformate were added at 0° C. under stirring. After 8 hours at room temperature the solvent was evaporated, the residue redissolved with methylene chloride and washed with saturated tartaric acid and then with water. The solvent was dried over anhydrous sodium sulfate and evaporated. The residue was purified by chromatography on silica gel using cyclohexane-ethylacetate as eluent to give 1.3 g (65% yield) of the title compound.

EXAMPLE 17

5-hydroxymethyl-2-benzyloxycarbonylamino-1,3-thiazole 530 mg (14 mmol) of sodium borohydride were added in small portions to a stirred solution of 7 g (27 mmol) of 2-benzyloxycarbonylamino-5-formyl-1,3-thiazole in 80 ml of methanol at room temperature. The reaction went on for 2 hours. After evaporation of the solvent the residue was purified by chromatography (cyclohexane-ethylacetate) to give 5.05 g (71% yield) of the title compound.

EXAMPLE 18

2-benzyloxycarbonylamino-5-(4-phenyl-1-sulfonyloxy)methyl-1,3-thiazole

To a solution of 1 g (3.78 mmol) of 2-benzyloxycarbonylamino-5-hydroxymethyl-1,3-thiazole in 25 ml of pyridine 0.86 g (4.54 mmol) of tosyl chloride in 10 ml of pyridine were dropped at 0° C. After stirring at room temperature for 6 hours the solvent was evaporated under vacuum, the residue redissolved with methylene chloride, washed with 1M hydrochloric acid and finally with water.

The organic layer was dried over anhydrous sodium sulfate and evaporated. The residue was purified by chromatography on silica gel (cyclohexane-ethylacetate) to give 1.2 g (80% yield) of the title compound.

EXAMPLE 19

2-benzyloxycarbonylamino-5-(2-ethoxycarbonyl-3-ethoxycarbonylethyl)-1,3-thiazole To a suspension of 321 mg of 55% sodium hydride in oil (7.4 mmol) in 20 ml of tetrahydrofuran 1.12 ml (7.4 mmol) of diethylmalonate were added. After 30 minutes, a solution of 1.5 g (3.7 mmol) of 2-benzyloxycarbonylamino-5-(4-phenyl-1-sulphonyloxy)methyl-1,3-thiazole in 10 ml of the same solvent was dropped under stirring. After 6 hours the solvent was evaporated and the residue redissolved with methylene chloride and washed with water. The organic layer was dried over anhydrous sodium sulfate and evaporated. The residue was chromatographed on a silica gel column (cyclohexane-ethylacetate) to give 1.05 g (70% yield) of the title compound.

EXAMPLE 20

2-benzyloxycarbonylamino-5-ethoxycarbonylethyl-1,3-thiazole

To a solution of 4.06 g (10 mmol) of 2-benzyloxycarbonylamino-5-(2-ethoxycarbonyl-3-ethoxycarbonylethyl)-1,3-thiazole in 10 ml of dimethylsulphoxide 0.64 g (11 mmol) of sodium chloride and 0.36 (20 mmol) of water were added under stirring. The mixture was heated at 160° C. for 8 hours and then the solvent removed under vacuum. The residue was redissolved with methylene chloride and washed with brine. After drying and concentration the residue was chromatographed on a silica gel column (cyclohexane-ethylacetate) to give 2.67 g (80% yield) of the title compound.

EXAMPLE 21

2-amino-5-carboxyethyl-1,3-thiazole 1 g (2.9 mmol) of 2-benzyloxycarbonylamino-5-ethoxycarbonylethyl-1,3-thiazole was dissolved in 20 ml of 33% hydrobromic acid in acetic acid. After 2 hours at room temperature, the solvent was evaporated under vacuum. The residue was redissolved in the minimum amount of water and the hydrobromide of the title compound was precipitated by adding diethylether (75% yield).

EXAMPLE 22

Preparation of methyl 2-[3-(3-chloropropoxy)phenyl]acetate

A mixture of methyl (m-hydroxyphenyl)acetate ((5 g, 0.03 moles), 1-bromo-3-chloropropane (3.26 ml, 0.03 moles) and anhydrous potassium carbonate (6.4 g) in anhydrous acetone (60 ml) was refluxed for 40 hours. After cooling, the precipitate was filtered off and the solution was evaporated to dryness to give the product as an oil, which was purified by flash chromatography with hexane:AcOEt (97:3) as eluent (6.2 g, 85% yield).

Analogously, the following product can be prepared:
methyl 2-[3-(2-chloroethoxy)phenyl]acetate.

EXAMPLE 23

Preparation of 2-[3-(3-chloropropoxy)phenyl]acetic acid

A mixture of methyl 2-[3-(3-chloropropoxy)phenyl]acetate (4.95 g, 0.02 moles) and a solution of 1N sodium hydroxide (0.02 moles) was stirred at room temperature for 24 hours. After acidification the acid separated as white powder (4.53 g, 97% yield)

m.p. 83–84° C.

Analogously, the following product can be prepared:
2-[3-(2-chloroethoxy)phenyl]acetic acid m.p. 100–101° C.

EXAMPLE 24

Preparation of N-(5-isopropyl-1,3-thiazol-2-yl)-2-{3-[3-(4-morpholinyl) propoxy]phenyl}acetamide A mixture of 2-[3-(3-chloropropoxy)phenyl]-N-(5-isopropyl-1,3-thiazol-2-yl)acetamide (1.00 g, 2.8 mmoles), morpholine (1.24 ml, 14.2 mmoles), potassium iodide (0.24 g, 1.4 mmoles) in anhydrous dimethylformamide (3.5 ml) was heated at 100° C. for 6 hours. The solution was acidified and extracted with ether to eliminate unreacted products; then the solution was basified and extracted with ether. The solvent was evaporated to dryness to give the product as an oily semisolid which was purified by flash chromatography with dichloromethane:methanol (97:3) as eluent (1.0 g, 87% yield)

$^1$H-NMR (DMSO-d$_6$) δ ppm: 12.09 (bs, 1H, CONH); 7.21 (t, 1H, H5 Ph); 7.13 (s, 1H, thiazole CH); 6.8–6.9 (m, 3H, H2, H4, H6 Ph); 3.97 (t, 2H, OCH$_2$CH$_2$CH$_2$N); 3.66 (s, 2H, COCH$_2$); 3.54 (t, 2H, OCH$_2$CH$_2$N); 3.07 (ept, 1H, CHMe$_2$); 2.39 (t, 2H, OCH$_2$CH$_2$CH$_2$N); 2.33 (t, 2H, OCH$_2$CH$_2$N); 2.14 (quint, 2H, OCH$_2$CH$_2$CH$_2$N); 1.22 (d, 6H, CHMe$_1$)

Analogously, the following product can be prepared:
N-(5-isopropyl-1,3-thiazol-2-yl)-2-{3-[2-(4-morpholinyl) ethoxy]phenyl}acetamide $^1$H-NMR (DMSO-d$_6$) δ ppm: 12.11 (bs, 1H, CONH); 7.20 (t, 1H, H5 Ph); 7.13 (d, 1H, thiazole CH); 6.7–6.9 (m, 3H, H2, H4, H6 Ph); 4.04 (t, 2H, OCH$_2$CH$_2$N); 3.66 (s, 2H, COCH$_2$); 3.55 (m, 4H, OCH$_2$CH$_2$N morpholine); 3.08 (m, 1H, CHMe$_2$); 2.66 (t, 2H, OCH$_2$CH$_2$N); 2.44 (m, 4H, OCH$_2$CH$_2$N morpholine); 1.22 (d, 6H, CHMe$_2$);

N-(5-isopropyl-1,3-thiazol-2-yl)-2-{3-[3-(1-pirrolidinyl) propoxy]phenyl}acetamide $^1$H-NMR (DMSO-d$_6$) δ ppm: 12.1 (bs, 1H, CONH); 7.19 (t, 1H, H5 Ph); 7.13 (d, 1H, thiazole CH); 6.7–6.9 (m, 3H, H2, H4, H6 Ph); 3.97 (t, 2H, OCH$_2$CH$_2$CH$_2$N); 3.66 (s, 2H, COCH$_2$); 3.08 (m, 1H, CHMe$_2$); 2.50 (m, 2H, OCH$_2$CH$_2$CH$_2$N); 2.41 (m, 4H, CH$_2$N pirrolidine); 1.85 (m, 2H, OCH$_2$CH$_2$CH$_2$N); 1.65 (m, 4H, CH$_2$CH$_2$N pirrolidine); 1.23 (d, 6H, CHMe$_2$);

N-(5-isopropyl-1,3-thiazol-2-yl)-2-{3-[3-(4-methyl-1-piperazinyl)propoxy]phenyl}acetamide $^1$H-NMR (DMSO-d$_6$) δ ppm: 12.1 (bs, 1H, CONH); 7.19 (t, 1H, H5 Ph); 7.13 (d, 1H, thiazole CH); 6.7–6.9 (m, 3H, H2, H4, H6 Ph); 3.95 (t, 2H, OCH$_2$CH$_2$CH$_2$N); 3.66 (s, 2H, COCH$_2$); 3.08 (m, 1H, CHMe$_2$); 2.15–2.45 (m, 10H, OCH$_2$CH$_2$CH$_2$N+piperazine); 2.11 (s, 3H, NMe); 1.82 (m, 2H, OCH$_2$CH$_2$CH$_2$N); 1.22 (d, 6H, CHMe$_2$).

2-{3-[2-(dimethylamino)ethoxy]phenyl}-N-(5-isopropyl-1,3-thiazol-2-yl)acetamide $^1$H-NMR (DMSO-d$_6$) δ ppm: 12.08 (bs, 1H, CONH); 7.2–6.90 (m, 5H, Ph+thiazole CH); 4.00 (t, 2H, OCH$_2$CH$_2$N); 3.66 (s, 2H, COCH$_2$); 3.07 (m, 1H, CHMe$_2$); 2.59 (t, 2H, OCH$_2$CH$_2$N); 2.11 (s, 3H, NMe); 2.19 (s, 6H, Me$_2$N); 1.22 (d, 6H, CHMe$_2$);

2-{3-[3-(dimethylamino)propoxy]phenyl}-N-(5-isopropyl-1,3-thiazol-2-yl)acetamide $^1$H-NMR (DMSO-d$_6$) δ ppm: 12.05 (bs, 1H, CONH); 7.19–6.79 (m, 5H, Ph+thiazole CH); 3.95 (t, 2H, OCH$_2$CH$_2$CH$_2$N); 3.66 (s, 2H, COCH$_2$); 3.08 (m, 1H, CHMe$_2$); 2.32 (t, 2H, OCH$_2$CH$_2$CH$_2$N); 2.11 (s, 3H, NMe$_2$); 1.81 (m, 2H, OCH$_2$CH$_2$CH$_2$N); 1.22 (d, 6H, CHMe$_2$)

EXAMPLE 25

Preparation of 2-[N-[2'-N'-(ethoxycarbonyl-methyl)-amino]acetyl]-amino-5-bromo-thiazole A solution of N-(5-bromo-1,3-thiazol-2-yl)-2-bromoacetamide (0.35 g, 1.17 mmol) in DMF (5 ml) was added dropwise to a solution of glycine ethyl ester hydrochloride (0.33 g, 2.33 mmol) and triethylamine (0.49 ml, 3.5 mmol) in DMF (10 ml). After 3 hours at room temperature, the reaction mixture was heated at 40° C. for about 5 hours and then diluted with water and extracted with methylene chloride. The combined organic layers were washed with brine, dried, concentrated and chromatographed on silica gel using cyclohexane:ethyl acetate 7:3 as eluent. The title compound was obtained as a colourless solid (0.15 g, 43%)

m.p. 115–116° C.

$^1$H-NMR (DMSO-d$_6$) δ ppm: 7.46 (s, 1H, H4thiaz), 4.05 (q, 2H, OCH2CH$_3$), 3.49 (s, 2H, NHCOCH$_2$), 3.4 (s, 2H, NHCH$_2$), 1.18 (t, 3H, OCH$_2$CH$_3$).

Analogously, the following compound can be prepared:
2-anilino-N-(5-isopropyl-1,3-thiazol-2-yl)acetamide: m.p. 143–145° C.

¹H-NMR (DMSO-d⁶) δ ppm: 11.92 (s, 1H, NHCO), 7.13 (s, 1H, H4thiaz), 7.06–6.6 (m, 5H, Ph), 6.0 (t, 1H, N<u>H</u>CH₂), 3.95 (d, 2H, NHC<u>H</u>₂), 3.08 (m, 1H, C<u>H</u>Me₂), 1.23 (d, 6H, CH<u>Me</u>₂)

EXAMPLE 26

Preparation of N-(5-isopropyl-1,3-thiazol-2-yl)-2-(2-bromophenyl)acetamide

To a suspension of resin N-Cyclohexylcarbodiimide N'-methylpolystyrene (0.251 g, 2.39 mmol g, 0.6 mmol), previously washed with DCM (3×5 ml), in DCM (4 ml) at room temperature, 2-bromophenylacetic acid (0.086 g, 0.4 mmol) was added. After 10 min., a solution of 2-amino-5-isopropyl-1,3-thiazole (0.0284 g, 0.2 mmol) in DCM (4 ml) was added. The mixture was shaked for 24 hours at room temperature, the resin filtered and washed with DCM (3×10 ml). The filtrated were combined, washed with water, 5% HCl, water, saturated sodium bicarbonate and water, dried over sodium sulfate and evaporated.

¹H-NMR (DMSO-d₅) δ ppm:10.05 (s broad, 1H, N<u>H</u>COCH₂), 7.6–7.2 (m, 4H, Ar), 7.08 (s, 1H, H4thiaz), 3.98 (s, 2H, NHCOC<u>H</u>₂), 3.11 (m, 1H, C<u>H</u>Me₂), 1.31 (d, 6H, CH<u>Me</u>₂)

All the compounds were characterised by Mass Spectroscopy (MS). LC-MS confirmed that in each case the principle component had a molecular ion corresponding to the expected product.

Chromatography: Reverse phase HPLC with UV detection were run.
Mobile A: water (0.1% TFA)
Mobile B: acetonitrile:water 95:5 (0.1% TFA)
Flow rate: 1 ml/min
Gradient: 10–100% B in 12 minutes, hold 100% B 3 min, return 10% B in 5 min
Detection: UV monitor 215, 254 and 300 nm
Sample were prepared as dilute solutions in acetonitrile (1—1.5 mM).
The compounds showed an HPLC area % ranging from 40 to 100%.

Starting from the suitable carboxylic acid, the following compounds can be prepared:
N-(5-isopropyl-1,3-thiazol-2-yl)-2-(2,3,4,5,6-pentafluorophenyl)acetamide;
N-(5-isopropyl-1,3-thiazol-2-yl)-2-(2-chlorophenyl)acetamide;
N-(5-isopropyl-1,3-thiazol-2-yl)-2-(2-nitrophenyl)acetamide;
N-(5-isopropyl-1,3-thiazol-2-yl)-2-(2-trifluoromethylphenyl)acetamide;
N-(5-isopropyl-1,3-thiazol-2-yl)-2-(2-methoxyphenyl)acetamide;
N-(5-isopropyl-1,3-thiazol-2-yl)-2-(2,5-dimethoxyphenyl)acetamide;
N-(5-isopropyl-1,3-thiazol-2-yl)-2-(2,5-difluorophenyl)acetamide;
N-(5-isopropyl-1,3-thiazol-2-yl)-2-(3,4,5-trimethoxyphenyl)acetamide;
N-(5-isopropyl-1,3-thiazol-2-yl)-2-(2,6-dichlorophenyl)acetamide;
N-(5-isopropyl-1,3-thiazol-2-yl)-2-(2-chloro-6-fluorophenyl)acetamide;
N-(5-isopropyl-1,3-thiazol-2-yl)-2-(3,5-dimethoxyphenyl)acetamide;
N-(5-isopropyl-1,3-thiazol-2-yl)-2-(3,5-difluorophenyl)acetamide;
N-(5-isopropyl-1,3-thiazol-2-yl)-2-(2,5-bis-trifluoromethylphenyl)acetamide;
N-(5-isopropyl-1,3-thiazol-2-yl)-2-(4-methylthiophenyl)acetamide;
N-(5-isopropyl-1,3-thiazol-2-yl)-2-(4-methoxyphenyl)acetamide;
N-(5-isopropyl-1,3-thiazol-2-yl)-2-(4-bromophenyl)acetamide;
N-(5-isopropyl-1,3-thiazol-2-yl)-2-(4-chlorophenyl)acetamide;
N-(5-isopropyl-1,3-thiazol-2-yl)-2-(4-nitrophenyl)acetamide;
N-(5-isopropyl-1,3-thiazol-2'-yl)-2-(4-trifluoromethylphenyl)acetamide;
N-(5-isopropyl-1,3-thiazol-2-yl)-2-(4-methylphenyl)acetamide;
N-(5-isopropyl-1,3-thiazol-2-yl)-2-(3-trifluoromethylphenyl)acetamide;
N-(5-isopropyl-1,3-thiazol-2-yl)-2-(3-chlorophenyl)acetamide;
N-(5-isopropyl-1,3-thiazol-2-yl)-2-(3-methoxyphenyl)acetamide;
N-(5-isopropyl-1,3-thiazol-2-yl)-2-(2,4-dinitrophenyl)acetamide;
N-(5-isopropyl-1,3-thiazol-2-yl)-2-(2,4-dichlorophenyl)acetamide;
N-(5-isopropyl-1,3-thiazol-2-yl)-2-(2,4-difluorophenyl)acetamide;
N-(5-isopropyl-1,3-thiazol-2-yl)-2-(4-benzyloxy-3-methoxyphenyl)acetamide;
N-(5-isopropyl-1,3-thiazol-2-yl)-2-(3,4-dichlorophenyl)acetamide;
N-(5-isopropyl-1,3-thiazol-2-yl)-2-(3,4-difluorophenyl)acetamide;
2-cyclopentyl-N-(5-isopropyl-1,3-thiazol-2-yl)-2-phenylacetamide;
2-cyclohexyl-N-(5-isopropyl-1,3-thiazol-2-yl)-2-phenylacetamide;
N-(5-isopropyl-1,3-thiazol-2-yl)-2,2-diphenylacetamide;
N-(5-isopropyl-1,3-thiazol-2-yl)-2-(2-nitrophenoxy)acetamide;
N-(5-isopropyl-1,3-thiazol-2-yl)-2-(4-nitrophenyl)propanamide;
N-(5-isopropyl-1,3-thiazol-2-yl)-2-(4-isobutylphenyl)propanamide;
N-(5-isopropyl-1,3-thiazol-2-yl)-2-oxo-2-phenylacetamide;
N-(5-isopropyl-1,3-thiazol-2-yl)-3-methyl-2-phenylpentanamide;
(E, Z)-N-(5-isopropyl-1,3-thiazol-2-yl)-2-phenyl-2-butenamide;
N-(5-isopropyl-1,3-thiazol-2-yl)bicyclo[4.2.0]octa-1,3,5-triene-7-carboxamide;
N-(5-isopropyl-1,3-thiazol-2-yl)-2-phenyl)butanamide;
tert-butyl (1R)-2-[(5-isopropyl-1,3-thiazol-2-yl)amino]-2-oxo-1-phenylethylcarbamate;
(1R)-2-[(5-isopropyl-1,3-thiazol-2-yl)amino]-2-oxo-1-phenylethyl acetate;
(1S)-2-[(5-isopropyl-1,3-thiazol-2-yl)amino]-2-oxo-1-phenylethyl acetate;
2-(acetylamino)-N-(5-isopropyl-1,3-thiazol-2-yl)-2-phenylacetamide;
(R)-2-(methoxy)-N-(5-isopropyl-1,3-thiazol-2-yl)-2-phenylacetamide;
3,3,3-trifluoro-N-(5-isopropyl-1,3-thiazol-2-yl)-2-methoxy-2-phenylpropanamide;
2-(2,4-dinitrophenyl)-N-(5-isopropyl-1,3-thiazol-2-yl)acetamide;

N-(5-isopropyl-1,3-thiazol-2-yl)-2-(5-benzyloxy-1H-indol-3-yl)acetamide;
N-(5-isopropyl-1,3-thiazol-2-yl)-2-(3-methoxy-2-methyl-1H-indol-3-yl)acetamide;
2-(1H-indol-3-yl)-N-(5-isopropyl-1,3-thiazol-2-yl)-2-oxoacetamide;
2-[1-(4-chlorobenzoyl)-5-methoxy-2-methyl-1H-indol-3-yl]-N-(5-isopropyl-1,3-thiazol-2-yl)acetamide;
4-(1H-indol-3-yl)-N-(5-isopropyl-1,3-thiazol-2-yl)butanamide;
N-(5-isopropyl-1,3-thiazol-2-yl)-3-(2-thienyl)propanamide
2-(5-chloro-1-benzothiophen-3-yl)-N-(5-isopropyl-1,3-thiazol-2-yl)acetamide;
2-(1-benzothiophen-3-yl)-N-(5-isopropyl-1,3-thiazol-2-yl)acetamide;
2-[2-(formylamino)-1,3-thiazol-4-yl]-N-(5-isopropyl-1,3-thiazol-2-yl)-2-(methoxyimino)acetamide;
2-{2-[(2-chloroacetyl)amino]-1,3-thiazol-4-yl}-N-(5-isopropyl-1,3-thiazol-2-yl)-2-(methoxyimino)acetamide;
2-chloro-N-(4-{2-[(5-isopropyl-1,3-thiazol-2-yl)amino]-2-oxoethyl}-1,3-thiazol-2-yl)acetamide;
Ethyl 2-({[2-[(5-isopropyl-1,3-thiazol-2-yl)amino]-2-oxo-1-(1H-pyrazol-3-yl)ethylidene]amino}oxy)acetate;
N-(5-isopropyl-1,3-thiazol-2-yl)-4-oxo-4-(4-methylphenyl)butanamide;
N-(5-isopropyl-1,3-thiazol-2-yl)-4-(4-nitrophenyl)butanamide;
N-(5-isopropyl-1,3-thiazol-2-yl)-4-phenylbutanamide;
benzyl 4-[(5-isopropyl-1,3-thiazol-2-yl)amino]-4-oxobutyl-carbamate;
4-(1,3-dioxo-1,3-dihydro-2H-isoindol-2-yl)-N-(5-isopropyl-1,3-thiazol-2-yl)butanamide;
N-(5-isopropyl-1,3-thiazol-2-yl)-4-(4-methoxy-1-naphthyl)-4-oxobutanamide;
3-(2-chlorophenoxy)-N-(5-isopropyl-1,3-thiazol-2-yl)propanamide;
3-(4-methylphenoxy)-N-(5-isopropyl-1,3-thiazol-2-yl)propanamide;
3-cyclopentyl-N-(5-isopropyl-1,3-thiazol-2-yl)propanamide;
3-cyclohexyl-N-(5-isopropyl-1,3-thiazol-2-yl)propanamide;
N-(5-isopropyl-1,3-thiazol-2-yl)-4-methylpentanamide;
3-(4-chlorophenyl)-N-(5-isopropyl-1,3-thiazol-2-yl)propanamide;
3-(4-methoxyphenyl)-N-(5-isopropyl-1,3-thiazol-2-yl)propanamide;
3-chloro-N-(5-isopropyl-1,3-thiazol-2-yl)propanamide;
3-phenyl-N-(5-isopropyl-1,3-thiazol-2-yl)propanamide;
N-(5-isopropyl-1,3-thiazol-2-yl)-5-oxo-5-phenylpentanamide;
2-[(5-isopropyl-1,3-thiazol-2-yl)amino]-2-oxo-1-phenylethyl acetate;
N-(5-isopropyl-1,3-thiazol-2-yl)-2-[4-(1-oxo-1,3-dihydro-2H-isoindol-2-yl)phenyl]propanamide;
1-(4-chlorophenyl)-N-(5-isopropyl-1,3-thiazol-2-yl)cyclopentanecarboxamide;
1-phenyl-N-(5-isopropyl-1,3-thiazol-2-yl)cyclopentanecarboxamide;
2-(3-bromo-4-methoxyphenyl)-N-(5-isopropyl 1,3-thiazol-2-yl)acetamide;
2-(2-nitro-4-trifluoromethylphenyl)-N-(5-isopropyl-1,3-thiazol-2-yl)acetamide;
5-cyclohexyl 1-(4-{2-[(5-isopropyl-1,3-thiazol-2-yl)amino]-2-oxoethylbenzyl) (2S)-2-[(tert-butoxycarbonyl)amino]pentanedioate;
2-(5,6-dimethyl-1H-benzimidazol-1-yl)-N-(5-isopropyl-1,3-thiazol-2-yl)acetamide;
2-[5-(4-chlorophenyl)-2H-1,2,3,4-tetraazol-2-yl]-N-(5-isopropyl-1,3-thiazol-2-yl)acetamide;
N-(5-isopropyl-1,3-thiazol-2-yl)-2-[5-(1-pyrrolidinyl)-2H-1,2,3,4-tetraazol-2-yl]acetamide;
N-(5-isopropyl-1,3-thiazol-2-yl)-2-(3-methyl-1-benzothiophen-2-yl)acetamide;
N-(5-isopropyl-1,3-thiazol-2-yl)-4,4-bis(4-methylphenyl)-3-butenamide;
2-cyclopropyl-N-(5-isopropyl-1,3-thiazol-2-yl)acetamide;
N-{4-bromo-6-[(5-isopropyl-1,3-thiazol-2-yl)amino]-6-oxohexyl}benzamide;
2-cyclopentyl-N-(5-isopropyl-1,3-thiazol-2-yl)acetamide;
benzyl 6-[(5-isopropyl-1,3-thiazol-2-yl)amino]-6-oxohexyl-carbamate;
N~1~-(5-isopropyl-1,3-thiazol-2-yl)-N~4~-(2-propynyl)-2-butenediamide
4-(2,4-dimethylphenyl)-N-(5-isopropyl-1,3-thiazol-2-yl)-4-oxobutanamide;
4-(4-benzyloxyphenyl)-N-(5-isopropyl-1,3-thiazol-2-yl)-4-oxobutanamide;
4-(thiphen-2-yl)-N-(5-isopropyl-1,3-thiazol-2-yl)-4-oxobutanamide;
benzyl 2-{[(benzyloxy)carbonyl]amino}-5-[(5-isopropyl-1,3-thiazol-2-yl)amino]-5-oxopentanoate;
4-(1H-indol-3-yl)-N-{3-[(5-isopropyl-1,3-thiazol-2-yl)amino]-3-oxopropyl}butanamide;
4-{[(5-isopropyl-1,3-thiazol-2-yl)amino]carbonyl}phenyl 4-chlorobenzenesulfonate;
N-(5-isopropyl-1,3-thiazol-2-yl)-4-{[(2-methoxyanilino)carbonyl]amino}benzamide;
4-{[2-(isopropylsulfonyl)acetyl]amino}-N-(5-isopropyl-1,3-thiazol-2-yl)benzamide;
N-(5-isopropyl-1,3-thiazol-2-yl)-4-{[2-(phenylsulfanyl)acetyl]amino}benzamide;
4-[(diethylamino)sulfonyl]-N-(5-isopropyl-1,3-thiazol-2-yl)benzamide;
2-bromo-N-(5-isopropyl-1,3-thiazol-2-yl)benzamide;
3,5-difluoro-N-(5-isopropyl-1,3-thiazol-2-yl)benzamide;
3-{[(2-fluoroanilino)carbonyl]amino}-N-(5-isopropyl-1,3-thiazol-2-yl)benzamide;
N-(5-isopropyl-1,3-thiazol-2-yl)-1-phenyl-5-propyl-1H-pyrazole-4-carboxamide;
3-chloro-4-(isopropylsulfonyl)-N-(5-isopropyl-1,3-thiazol-2-yl)-2-(methylsulfanyl)-2-thiophenecarboxamide;
3-iodo-4-(isopropylsulfonyl)-N-(5-isopropyl-1,3-thiazol-2-yl)-5-(methylsulfanyl)-2-thiophenecarboxamide;
2-{[(4-chlorophenyl)sulfonyl]methyl}-N-(5-isopropyl-1,3-thiazol-2-yl)-4-methyl-1,3-thiazole-5-carboxamide;
5-(4-chlorophenyl)-N-(5-isopropyl-1,3-thiazol-2-yl)-2-(trifluoromethyl)-3-furamide;
3,5-dichloro-N-(5-isopropyl-1,3-thiazol-2-yl)benzamide;
3,4-dichloro-N-(5-isopropyl-1,3-thiazol-2-yl)benzamide;
2,4-dichloro-N-(5-isopropyl-1,3-thiazol-2-yl)benzamide;
2,3-dichloro-N-(5-isopropyl-1,3-thiazol-2-yl)benzamide;
3-iodio-N-(5-isopropyl-1,3-thiazol-2-yl)benzamide;
2-iodio-N-(5-isopropyl-1,3-thiazol-2-yl)benzamide;
4-iodio-N-(5-isopropyl-1,3-thiazol-2-yl)benzamide;
3-bromo-N-(5-isopropyl-1,3-thiazol-2-yl)benzamide;
4-chloro-2-fluoro-N-(5-isopropyl-1,3-thiazol-2-yl)benzamide;
5-bromo-2-chloro-N-(5-isopropyl-1,3-thiazol-2-yl)benzamide;
3-chloro-N-(5-isopropyl-1,3-thiazol-2-yl)benzamide;
2-chloro-N-(5-isopropyl-1,3-thiazol-2-yl)benzamide;
3-fluoro-N-(5-isopropyl-1,3-thiazol-2-yl)benzamide;
2-fluoro-N-(5-isopropyl-1,3-thiazol-2-yl)benzamide;
2,4-difluoro-N-(5-isopropyl-1,3-thiazol-2-yl)benzamide;

3,4-difluoro-N-(5-isopropyl-1,3-thiazol-2-yl)benzamide;
2,3,4,5,6-pentafluoro-N-(5-isopropyl-1,3-thiazol-2-yl)benzamide;
N-(5-isopropyl-1,3-thiazol-2-yl)-4-methyl-3-nitrobenzamide;
N-(5-isopropyl-1,3-thiazol-2-yl)-5-methyl-2-nitrobenzamide;
N-(5-isopropyl-1,3-thiazol-2-yl)-3-methyl-2-nitrobenzamide;
N-(5-isopropyl-1,3-thiazol-2-yl)-3,5-dimethyl-4-nitrobenzamide;
N-(5-isopropyl-1,3-thiazol-2-yl)-4-methoxy-2-nitrobenzamide;
N-(5-isopropyl-1,3-thiazol-2-yl)-3-methoxy-2-nitrobenzamide;
N-(5-isopropyl-1,3-thiazol-2-yl)-4-methoxy-3-nitrobenzamide;
N-(5-isopropyl-1,3-thiazol-2-yl)-3-methoxy-4-nitrobenzamide;
N-(5-isopropyl-1,3-thiazol-2-yl)-3,5-dinitrobenzamide;
5-{[(5-isopropyl-1,3-thiazol-2-yl)amino]carbonyl}-2-nitrophenyl octanoate;
N-(5-isopropyl-1,3-thiazol-2-yl)-2-nitrobenzamide;
N-(5-isopropyl-1,3-thiazol-2-yl)-4-nitrobenzamide;
4-chloro-N-(5-isopropyl-1,3-thiazol-2-yl)-3-nitrobenzamide;
4-chloro-N-(5-isopropyl-1,3-thiazol-2-yl)-2-nitrobenzamide;
2-chloro-N-(5-isopropyl-1,3-thiazol-2-yl)-4-nitrobenzamide;
5-chloro-N-(5-isopropyl-1,3-thiazol-2-yl)-2-nitrobenzamide;
2-bromo-N-(5-isopropyl-1,3-thiazol-2-yl)-5-nitrobenzamide;
4-fluoro-N-(5-isopropyl-1,3-thiazol-2-yl)-3-nitrobenzamide;
4-fluoro-N-(5-isopropyl-1,3-thiazol-2-yl)-2-nitrobenzamide;
N-(5-isopropyl-1,3-thiazol-2-yl)-2-nitro-4-(trifluoromethyl)benzamide;
N-(5-isopropyl-1,3-thiazol-2-yl)-3,5-bis(trifluoromethyl)benzamide;
N-(5-isopropyl-1,3-thiazol-2-yl)-2,6-bis(trifluoromethyl)benzamide;
N-(5-isopropyl-1,3-thiazol-2-yl)-2-(trifluoromethyl)benzamide;
N-(5-isopropyl-1,3-thiazol-2-yl)-3-(trifluoromethyl)benzamide;
3-fluoro-N-(5-isopropyl-1,3-thiazol-2-yl)-4-(trifluoromethyl)benzamide;
2-fluoro-N-(5-isopropyl-1,3-thiazol-2-yl)-3-(trifluoromethyl)benzamide;
5-fluoro-N-(5-isopropyl-1,3-thiazol-2-yl)-3-(trifluoromethyl)benzamide;
2-fluoro-N-(5-isopropyl-1,3-thiazol-2-yl)-4-(trifluoromethyl)benzamide;
4-fluoro-N-(5-isopropyl-1,3-thiazol-2-yl)-3-(trifluoromethyl)benzamide;
methyl 2-{[(5-isopropyl-1,3-thiazol-2-yl)amino]carbonyl}benzoate;
4-cyano-N-(5-isopropyl-1,3-thiazol-2-yl)benzamide;
3-cyano-N-(5-isopropyl-1,3-thiazol-2-yl)benzamide;
N-(5-isopropyl-1,3-thiazol-2-yl)-3-methylbenzamide;
N-(5-isopropyl-1,3-thiazol-2-yl)-2-methylbenzamide;
N-(5-isopropyl-1,3-thiazol-2-yl)-4-methylbenzamide;
N-(5-isopropyl-1,3-thiazol-2-yl)-4-vinylbenzamide;
N-(5-isopropyl-1,3-thiazol-2-yl)-4-(2-phenylethynyl)benzamide;
N-(5-isopropyl-1,3-thiazol-2-yl)-3-methoxy-4-methylbenzamide;
2-benzyl-N-(5-isopropyl-1,3-thiazol-2-yl)benzamide;
N-(5-isopropyl-1,3-thiazol-2-yl)-2-phenethylbenzamide;
N-(5-isopropyl-1,3-thiazol-2-yl)-2-phenylbenzamide;
N-(5-isopropyl-1,3-thiazol-2-yl)-4-phenylbenzamide;
4-(tert-butyl)-N-(5-isopropyl-1,3-thiazol-2-yl)benzamide;
N-(5-isopropyl-1,3-thiazol-2-yl)-4-isopropylbenzamide;
N-(5-isopropyl-1,3-thiazol-2-yl)-4-pentylbenzamide;
3-fluoro-N-(5-isopropyl-1,3-thiazol-2-yl)-4-methylbenzamide;
N-(5-isopropyl-1,3-thiazol-2-yl)-3,4-dimethylbenzamide;
N-(5-isopropyl-1,3-thiazol-2-yl)-3,5-dimethylbenzamide;
N-(5-isopropyl-1,3-thiazol-2-yl)-4-(methylsulfonyl)benzamide;
3-fluoro-N-(5-isopropyl-1,3-thiazol-2-yl)-4-methoxybenzamide;
3-chloro-N-(5-isopropyl-1,3-thiazol-2-yl)-4-methoxybenzamide;
5-chloro-N-(5-isopropyl-1,3-thiazol-2-yl)-2-methoxybenzamide;
N-(5-isopropyl-1,3-thiazol-2-yl)-4-methoxybenzamide;
N-(5-isopropyl-1,3-thiazol-2-yl)-3-methoxybenzamide;
N-(5-isopropyl-1,3-thiazol-2-yl)-2-methoxybenzamide;
N-(5-isopropyl-1,3-thiazol-2-yl)-3,4-dimethoxybenzamide;
N-(5-isopropyl-1,3-thiazol-2-yl)-3,5-dimethoxybenzamide;
N-(5-isopropyl-1,3-thiazol-2-yl)-2,4-dimethoxybenzamide;
N-(5-isopropyl-1,3-thiazol-2-yl)-2,3-dimethoxybenzamide;
N-(5-isopropyl-1,3-thiazol-2-yl)-3-phenoxybenzamide;
N-(5-isopropyl-1,3-thiazol-2-yl)-2-phenoxybenzamide;
N-(5-isopropyl-1,3-thiazol-2-yl)-4-phenoxybenzamide;
2-ethoxy-N-(5-isopropyl-1,3-thiazol-2-yl)benzamide;
4-ethoxy-N-(5-isopropyl-1,3-thiazol-2-yl)benzamide;
N-(5-isopropyl-1,3-thiazol-2-yl)-3,4,5-trimethoxybenzamide;
3,4-diethoxy-N-(5-isopropyl-1,3-thiazol-2-yl)benzamide;
3,4,5-triethoxy-N-(5-isopropyl-1,3-thiazol-2-yl)benzamide
N-(5-isopropyl-1,3-thiazol-2-yl)-3-methoxy-4-(methoxymethoxy)benzamide;
4-butoxy-N-(5-isopropyl-1,3-thiazol-2-yl)benzamide;
N-(5-isopropyl-1,3-thiazol-2-yl)-4-propoxybenzamide;
4-isopropoxy-N-(5-isopropyl-1,3-thiazol-2-yl)benzamide;
N-(5-isopropyl-1,3-thiazol-2-yl)-1,3-benzodioxole-5-carboxamide;
4-(benzyloxy)-N-(5-isopropyl-1,3-thiazol-2-yl)benzamide;
4-(2-cyclohexen-1-yloxy)-N-(5-isopropyl-1,3-thiazol-2-yl)benzamide;
N-(5-isopropyl-1,3-thiazol-2-yl)-4-(trifluoromethoxy) benzamide;
4-(difluoromethoxy)-N-(5-isopropyl-1,3-thiazol-2-yl)benzamide;
N-(5-isopropyl-1,3-thiazol-2-yl)-4-(methylsulfanyl)benzamide;
2-[(4-chlorophenyl)sulfinyl]-N-(5-isopropyl-1,3-thiazol-2-yl)benzamide;
N-(5-isopropyl-1,3-thiazol-2-yl)-2-[(4-nitrophenyl)sulfinyl]benzamide;
N-(5-isopropyl-1,3-thiazol-2-yl)-4-[(4-methylphenyl)sulfonyl]-3-nitrobenzamide;
N-(5-isopropyl-1,3-thiazol-2-yl)-3[(trifluoromethyl)sulfanyl]benzamide;
N-(5-isopropyl-1,3-thiazol-2-yl)-2-methoxy-4-(methylsulfanyl)benzamide;
2-[(2-cyanophenyl)sulfanyl]-N-(5-isopropyl-1,3-thiazol-2-yl)benzamide;

N~1~,N~1~-diethyl-3,6-difluoro-N~2~-(5-isopropyl-1,3-thiazol-2-yl)phthalamide;
4-formyl-N-(5-isopropyl-1,3-thiazol-2-yl)benzamide;
2-formyl-N-(5-isopropyl-1,3-thiazol-2-yl)benzamide;
4-{[(2,5-dimethoxyanilino)carbonyl]amino}-N-(5-isopropyl-1,3-thiazol-2-yl)benzamide;
4-(hydroxymethyl)-N-(5-isopropyl-1,3-thiazol-2-yl)benzamide;
4-{[(5-isopropyl-1,3-thiazol-2-yl)amino]carbonyl}-2-nitrobenzyl acetate;
4-{[(5-isopropyl-1,3-thiazol-2-yl)amino]carbonyl}-2-nitrobenzyl 4-(acetylamino)-3-iodobenzoate;
4-(acetylamino)-N-(5-isopropyl-1,3-thiazol-2-yl)benzamide;
N-(5-isopropyl-1,3-thiazol-2-yl)-4-[(2-phenylacetyl)amino]benzamide;
4-(acetylamino)-3-iodo-N-(5-isopropyl-1,3-thiazol-2-yl)benzamide;
4-amino-N-(5-isopropyl-1,3-thiazol-2-yl)benzamide;
4-(dimethylamino)-N-(5-isopropyl-1,3-thiazol-2-yl)benzamide;
3-(dimethylamino)-N-(5-isopropyl-1,3-thiazol-2-yl)benzamide;
2-(methylamino)-N-(5-isopropyl-1,3-thiazol-2-yl)benzamide;
N-(5-isopropyl-1,3-thiazol-2-yl)-2-[3-(trifluoromethyl)anilino]benzamide;
3-{[(5-bromo-1,3-dioxo-1,3-dihydro-2H-isoindol-2-yl)methyl]amino}-N-(5-isopropyl-1,3-thiazol-2-yl)benzamide;
N-(5-isopropyl-1,3-thiazol-2-yl)-4-(1H-pyrrol-1-yl)benzamide;
2,6-dichloro-N-(5-isopropyl-1,3-thiazol-2-yl)isonicotinamide;
2-(4-bromophenyl)-6-(4-iodophenyl)-N-(5-isopropyl-1,3-thiazol-2-yl)isonicotinamide;
N-(5-isopropyl-1,3-thiazol-2-yl)-2-[3-(trifluoromethyl)anilino]nicotinamide;
5,6-dichloro-N-(5-isopropyl-1,3-thiazol-2-yl)nicotinamide;
2-chloro-N-(5-isopropyl-1,3-thiazol-2-yl)-6-methylnicotinamide;
2,6-dichloro-5-fluoro-N-(5-isopropyl-1,3-thiazol-2-yl)nicotinamide
N-(5-isopropyl-1,3-thiazol-2-yl)-2-phenoxynicotinamide;
N-(5-isopropyl-1,3-thiazol-2-yl)-6-(2,2,2-trifluoroethoxy)nicotinamide;
N-(5-isopropyl-1,3-thiazol-2-yl)-2,6-dimethoxynicotinamide;
N-(5-isopropyl-1,3-thiazol-2-yl)-2-quinoxalinecarboxamide;
N-(5-isopropyl-1,3-thiazol-2-yl)-5-methyl-2-pyrazinecarboxamide;
N-(5-isopropyl-1,3-thiazol-2-yl)-8-quinolinecarboxamide;
N-(5-isopropyl-1,3-thiazol-2-yl)-2-phenyl-4-quinolinecarboxamide;
N-(5-isopropyl-1,3-thiazol-2-yl)-5-methyl-1-phenyl-1H-pyrazole-4-carboxamide;
N-(5-isopropyl-1,3-thiazol-2-yl)-5-methyl-1H-pyrazole-3-carboxamide;
N-(5-isopropyl-1,3-thiazol-2-yl)-1H-pyrazole-4-carboxamide;
N-(5-isopropyl-1,3-thiazol-2-yl)-5-methyl-2-phenyl-2H-1,2,3-triazole-4-carboxamide;
2-[(2,1,3-benzoxadiazol-5-yloxy)methyl]-N-(5-isopropyl-1,3-thiazol-2-yl)-4-methyl-1,3-thiazole-5-carboxamide;
N-(5-isopropyl-1,3-thiazol-2-yl)-9H-fluorene-1-carboxamide;
N-(5-isopropyl-1,3-thiazol-2-yl)-7-methoxy-1-benzofuran-2-carboxamide;
N-(5-isopropyl-1,3-thiazol-2-yl)-1-[(4-methylphenyl)sulfonyl]-1H-pyrrole-3-carboxamide;
2-ethoxy-N-(5-isopropyl-1,3-thiazol-2-yl)-1-naphthamide;
4-fluoro-N-(5-isopropyl-1,3-thiazol-2-yl)-1-naphthamide;
N-(5-isopropyl-1,3-thiazol-2-yl)-2-naphthamide;
N-(5-isopropyl-1,3-thiazol-2-yl)-9,10-dioxo-9,10-dihydro-2-anthracenecarboxamide;
N-(5-isopropyl-1,3-thiazol-2-yl)-9-oxo-9H-fluorene-4-carboxamide
N-(5-isopropyl-1,3-thiazol-2-yl)-9-oxo-9H-fluorene-1-carboxamide;
N-(5-isopropyl-1,3-thiazol-2-yl)-8-oxo-5,6,7,8-tetrahydro-2-naphthalenecarboxamide;
N-(5-isopropyl-1,3-thiazol-2-yl)-1,3-dioxo-1,3-dihydro-2-benzofuran-5-carboxamide;
N-(5-isopropyl-1,3-thiazol-2-yl)-1H-indole-5-carboxamide;
N-(5-isopropyl-1,3-thiazol-2-yl)-1H-indole-4-carboxamide;
N-(5-isopropyl-1,3-thiazol-2-yl)-1-methyl-2-phenyl-1H-indole-5-carboxamide;
2-butyl-N-(5-isopropyl-1,3-thiazol-2-yl)-1-methyl-1H-indole-5-carboxamide;
N-(5-isopropyl-1,3-thiazol-2-yl)-1H-indole-6-carboxamide;
N-(5-isopropyl-1,3-thiazol-2-yl)-5-methoxy-1H-indole-2-carboxamide;
1-allyl-2-butyl-N-(5-isopropyl-1,3-thiazol-2-yl)-1H-indole-5-carboxamide;
N-(5-isopropyl-1,3-thiazol-2-yl)-1-methyl-1H-indole-2-carboxamide;
1-benzyl-N-(5-isopropyl-1,3-thiazol-2-yl)-2-phenyl-1H-indole-5-carboxamide;
N-(5-isopropyl-1,3-thiazol-2-yl)-1H-1,2,3-benzotriazole-5-carboxamide;
N-(5-isopropyl-1,3-thiazol-2-yl)-3,5-dimethyl-4-isoxazolecarboxamide;
N-(5-isopropyl-1,3-thiazol-2-yl)-3-thiophenecarboxamide;
N-(5-isopropyl-1,3-thiazol-2-yl)-3-methyl-2-thiophenecarboxamide;
N-(5-isopropyl-1,3-thiazol-2-yl)-5-methyl-2-thiophenecarboxamide;
5-bromo-N-(5-isopropyl-1,3-thiazol-2-yl)-2-thiophenecarboxamide;
N-(5-isopropyl-1,3-thiazol-2-yl)-3-[(2,3,3-trichloroacryloyl)amino]-2-thiophenecarboxamide;
N-(5-isopropyl-1,3-thiazol-2-yl)-2-furamide;
N-(5-isopropyl-1,3-thiazol-2-yl)-5-(4-nitrophenyl)-2-furamide;
N-(5-isopropyl-1,3-thiazol-2-yl)-5-(2-nitrophenyl)-2-furamide;
5-(4-chlorophenyl)-N-(5-isopropyl-1,3-thiazol-2-yl)-2-furamide;
N-(5-isopropyl-1,3-thiazol-2-yl)-5-[3-(trifluoromethyl)phenyl]-2-furamide;
5-(4-chloro-2-nitrophenyl)-N-(5-isopropyl-1,3-thiazol-2-yl)-2-furamide;
N-(5-isopropyl-1,3-thiazol-2-yl)-5-(4-methyl-2-nitrophenyl)-2-furamide
5-[2-chloro-5-(trifluoromethyl)phenyl]-N-(5-isopropyl-1,3-thiazol-2-yl)-2-furamide;
tert-butyl (1S)-2-[(5-isopropyl-1,3-thiazol-2-yl)amino]-1-methyl-2-oxoethylcarbamate
tert-butyl (1S,2S)-1-{[(5-isopropyl-1,3-thiazol-2-yl)amino]carbonyl}-2-methylbutylcarbamate
tert-butyl 2-[(5-isopropyl-1,3-thiazol-2-yl)amino]-2-oxoethylcarbamate tert-butyl (1S)-5-amino-1-([[(5-isopropyl-1,3-thiazol-2-yl)amino]carbonyl}pentylcarbamate
tert-butyl 4-[(imino{[(4-methylphenyl)sulfonyl]amino}methyl)amino]-1-{[(5-isopropyl-1,3-thiazol-2-yl)amino]carbonyl}butylcarbamate
tert-butyl 1-{[(5-isopropyl-1,3-thiazol-2-yl)amino]carbonyl}-3-(tritylamino)propylcarbamate
tert-butyl (1S)-1-(benzyloxymethyl)-2-[(5-isopropyl-1,3-thiazol-2-yl)amino]-2-oxoethylcarbamate
tert-butyl (1S)-1-benzyl-2-[(5-isopropyl-1,3-thiazol-2-yl)amino]-2-oxoethylcarbamate
tert-butyl (1R)-2-[(5-isopropyl-1,3-thiazol-2-yl)amino]-2-oxo-1-(benzylthiomethyl)ethylcarbamate
benzyl (3S)-3-[(tert-butoxycarbonyl)amino]-4-[(5-isopropyl-1,3-thiazol-2-yl)amino]-4-oxobutanoate
tert-butyl (2S)-2-{[(5-isopropyl-1,3-thiazol-2-yl)amino]carbonyl}-1-pyrrolidinecarboxylate
tert-butyl (1S)-1-(1H-indol-3-ylmethyl)-2-[(5-isopropyl-1,3-thiazol-2-yl)amino]-2-oxoethylcarbamate
tert-butyl (1S)-1-{[(5-isopropyl-1,3-thiazol-2-yl)amino]carbonyl}-3-(methylsulfanyl)propylcarbamate
tert-butyl (1S)-2-benzyloxy-1-{[(5-isopropyl-1,3-thiazol-2-yl)amino]carbonyl}propylcarbamate
tert-butyl (1S)-1-(4-benzyloxybenzyl)-2-[(5-isopropyl-1,3-thiazol-2-yl)amino]-2-oxoethylcarbamate
tert-butyl (1S)-1-{[(5-isopropyl-1,3-thiazol-2-yl)amino]carbonyl}-2-methylpropylcarbamate
tert-butyl (1S)-1-{[(5-isopropyl-1,3-thiazol-2-yl)amino]carbonyl}-3-methylbutylcarbamate and
benzyl (4S)-4-[(tert-butoxycarbonyl)amino]-5-[(5-isopropyl-1,3-thiazol-2-yl)amino]-5-oxopentanoate.

Following the same procedure as reported in Example 3, the compounds described in the table (I) below can be prepared:

TABLE I

| MOLSTRUCTURE | mp °C. | $^1$H-NMR | Solvent |
|---|---|---|---|
| | | 12.23(s broad, 1H, NHCOCH$_2$), 8.22–7.62(m, 4H, Ar), 7.15 (s, 1H, H4thiaz), 3.91(s, 2H, NHCOCH$_2$), 3.08(m, 1H, CHMe$_2$), 1.22(d, 6H, CHMe$_2$) | DMSO-d$^6$ |
| | | 9.81(s broad, 1H, NHCOCH$_2$), 7.5–7.3(m, 4H, Ar), 7.11(s, 1H, H4thiaz), 4.83(s, 1H, NHCOCH), 3.44(s, 3H, Ome) 3.11(m, 1H, CHMe$_2$), 1.3(d, 6H, CHMe$_2$) | DMSO-d$^6$ |
| | 124–125 | 12.06(s broad, 1H, NHCO), 7.13 (s, 1H, H4thiaz) 6.92–6.81(m, 3H, Ar), 3.72(s, 3H, OMe), 3.70(s, 3H, OMe), 3.61(s, 2H, NHCOCH$_2$), 3.07(m, 1H, CHMe$_2$), 1.22(d, 6H, CHMe$_2$) | DMSO-d$^6$ |
| Chiral | 77–78 | 12.05(s broad, 1H, NHCO), 7.38–7.29(m, 5H, Ar), 7.12(s, 1H, H4thiaz), 4.95(s, 1H, CHOMe), 3.23(s, 2H, CHOMe), 3.05(m, 1H, CHMe$_2$), 1.20(d, 6H, CHMe$_2$) | DMSO-d$^6$ |

TABLE I-continued

| MOLSTRUCTURE | mp ° C. | ¹H-NMR | Solvent |
|---|---|---|---|
| 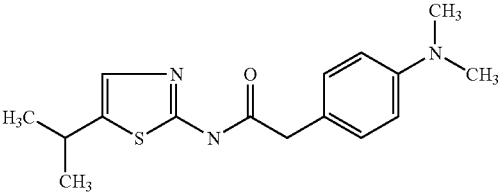 | 136–137 | 12.08(s broad, 1H, NHCOCH₂), 7.28 (d, 2H, Ar), 7.13(s, 1H, H4thiaz), 7.1(d, 2H, Ar), 3.65 (s, 2H, NHCOCH₂), 3.06(m, 1H, CHMe₂), 2.98(s, 6H, NMe₂), 1.22 (d, 6H, CHMe₂) | DMSO-d⁶ |
| 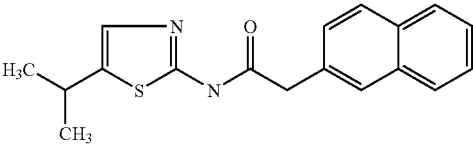 | 130–131 | 12.22(s, 1H, NHCO), 7.85–7.48 (m, 7H, Ar), 7.14(s, 1H, H4thiaz), 3.89(s, 2H, CH₂CO), 3.07(m, 1H, CHMe₂), 1.22(d, 6H, CHMe₂) | DMSO-d⁶ |
| 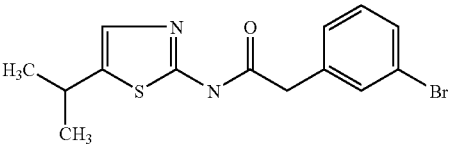 | 130–131 | 12.16(s, 1H, NHCO), 7.52–7.29 (m, 4H, Ar), 7.14(s, 1H, H4thiaz), 3.73(s, 2H, CH₂CO), 3.08(m, 1H, CHMe₂), 1.22(d, 6H, CHMe₂) | DMSO-d⁶ |
| 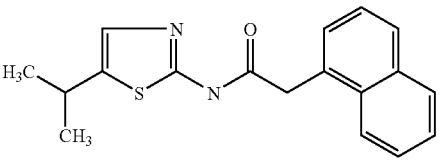 | 177–178 | 8.07–7.48(m, 7H, Ar), 7.15 (s, 1H, H4thiaz), 4.22(s, 2H, CH₂CO), 3.06(m, 1H, CHMe₂), 1.20(d, 6H, CHMe₂) | DMSO-d⁶ |
| 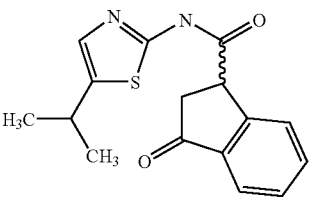 | 223–224 | 12.61(s, 1H, NHCO), 7.69–7.51 (m, 4H, Ar), 7.19(s, 1H, H4thiaz), 4.55(dd, 1H, CHCO), 3.08(m, 1H, CHMe₂), 2.89(m, 2H, COCH₂CH), 1.22(d, 6H, CHMe₂) | DMSO-d⁶ |
| 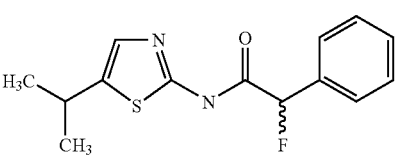 | 105–106 | 12.50(s, 1H, NHCO), 7.53–7.51 (m, 5H, Ar), 7.18(s, 1H, H4thiaz), 6.12(d, 1H, J_{H–F}=46.8, CHF), 3.09(m, 1H, CHMe₂), 1.22 (d, 6H, CHMe₂) | DMSO-d⁶ |
| 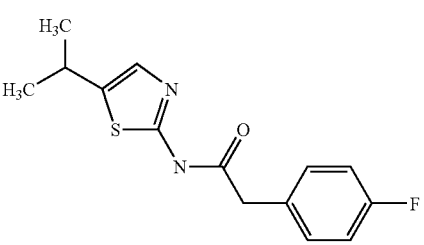 | 150–152 | 11.20(s broad, 1H, NHCO), 7.28–7.07(m, 5H, Ar+H4thiaz), 3.80 (s, 2H, CH₂CO), 3.13(m, 1H, CHMe₂), 1.32(d, 6H, CHMe₂) | DMSO-d⁶ |

TABLE I-continued

| MOLSTRUCTURE | mp ° C. | ¹H-NMR | Solvent |
|---|---|---|---|
| 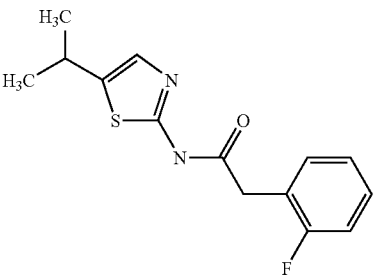 | 164–166 | 11.45(s broad, 1H, NHCO), 7.37–7.14(m, 5H, Ar+H4thiaz), 3.88 (s, 2H, NHCOCH₂), 3.12(m, 1H, CHMe₂), 1.32(d, 6H, CHMe₂) | DMSO-d⁶ |
| 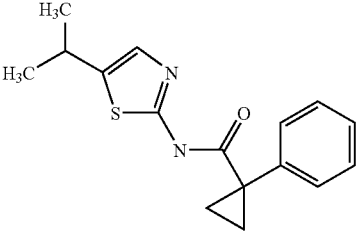 | 98–100 | 8.35(s broad, 1H, NHCO), 7.40 (m, 5H, Ar), 6.99(s, 1H, H4thiaz), 3.10(m, 1H, CHMe₂), 1.78(m, 2H, CH₂), 1.29(m, 2H, CH₂), 1.25(d, 6H, CHMe₂) | CDCl₃ |
| 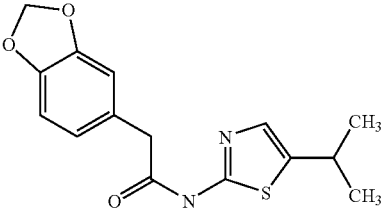 | 130–132 | 12.06(s broad), 1H, NHCOCH₂), 7.13 (s, 1H, H4thiaz), 6.86–6.75(m, 3H, Ar), 5.96(s, 2H, OCH₂O), 3.60(s, 2H, NNCOCH₂), 3.05(m, 1H, CHMe₂), 1.22(d, 6H, CHMe₂) | DMSO-d⁶ |
| 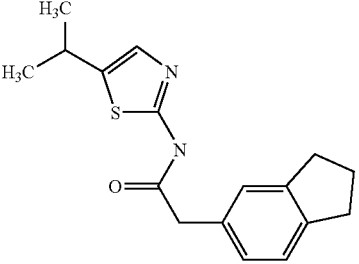 | 100–102 | 12.1(s broad, 1H, NHCOCH₂), 7.2–7(m, 4H, Ar+H4thiaz), 3.64(s, 2H, NHCOCH₂), 3.07(m, 1H, CHMe₂), 2.8–1.97(m, 6H, —CH₂CH₂CH₂—), 1.22(d, 6H, CHMe₂) | DMSO-d⁶ |
| 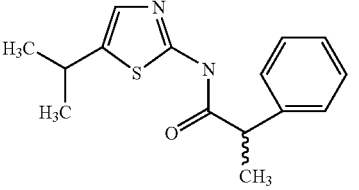 | 98–100 | 12.06(s broad, 1H, NHCO), 7.3 (m, 5H, Ar), 7.03(s, 1H, H4thiaz), 3.79(q, 1H, CHMe), 3.10 (m, 1H, CHMe₂), 1.59(d, 3H, CHMe), 1.30(d, 6H, CHMe₂) | DMSO-d⁶ |
| 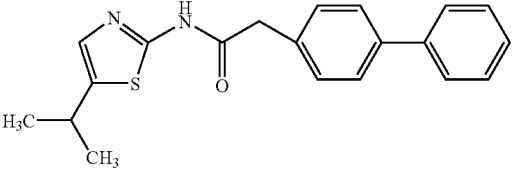 | 167–169 | 10(s broad, 1H, NHCOCH₂), 7.6–7.4 (m, 9H, Ar), 7.04(s, 1H, H4thiaz), 3.84(s, 2H, NHCOCH₂), 3.11(m, 1H, CHMe₂), 1.31(d, 6H, CHMe₂) | DMSO-d⁶ |

TABLE I-continued

| MOLSTRUCTURE | mp ° C. | ¹H-NMR | Solvent |
|---|---|---|---|
| Chiral, 5-isopropyl-thiazol-2-yl N-acyl with CH(CH₃)Ph | 115–116 | 12.06(s broad, 1H, NHCO), 7.26 (m, 5H, Ar), 6.99(s, 1H, H4thiaz), 3.79(q, 1H, CHMe), 3.10 (m, 1H, CHMe₂), 1.59(d, 3H, CHMe), 1.30(d, 6H, CHMe₂) | DMSO-d⁶ |
| Chiral, 5-isopropyl-thiazol-2-yl N-acyl with CH(CH₃)Ph | 112–114 | 12.06(s broad, 1H, NHCO), 7.33 (m, 5H, Ar), 7.11(s, 1H, H4thiaz), 3.93(q, 1H, CHMe), 3.07 (m, 1H, CHMe₂), 1.40(d, 3H, CHMe), 1.22(d, 6H, CHMe₂) | DMSO-d⁶ |
| 5-isobutyl-thiazol-2-yl amide with 4-(NMe₂)phenylacetyl | 124–126 | 12.01(s broad, 1H, NHCO), 7.11–6–65(m, 5H, Ar+H4thiaz), 3.55 (s, 2H, NHCOCH₂), 2.83(s, 6H, NMe₂), 2.56(d, 2H, CH₂iPr), 1.74 (m, 1H, CHMe₂), 0.87(d, 6H, CHMe₂) | DMSO-d⁶ |
| 5-isobutyl-thiazol-2-yl amide with 3,4-methylenedioxyphenylacetyl | 139–141 | 9.90(s broad, 1H, NHCO), 7.04 (s, 1H, H4thiaz), 6.78(m, 3H, Ar), 5.96(s, 2H, OCH₂O), 3.72(s, 2H, NHCOCH₂), 2.60(d, 2H, CH₂iPr), 1.85(m, 1H, CHMe₂), 0.93 (d, 6H, CHMe₂) | CDCl₃ |
| 5-benzyl-thiazol-2-yl amide with 4-(NMe₂)phenylacetyl | 175–177 | 12.0(s broad, 1H, NHCO), 7.28 (m, 6H, CH₂Ph+H4thiaz), 7.08–6.64 (m, 4H, Ar), 4.04(s, 2H, CH₂Ph), 3.53(s, 2H, NHCOCH₂), 2.82(s, 6H, NMe₂) | DMSO-d⁶ |
| 5-isopropyl-thiazol-2-yl amide with 3-(2-methoxyethoxy)phenylacetyl | 88–90 | 12.08(s broad, 1H, NHCO), 7.20–6.81(m, 5H, Ar+H4thiaz), 4.01 (dd, 2H, OCH₂CH₂OMe), 3.68(s, 2H, NHCOCH₂), 3.61(dd, 2H OCH₂CH₂OMe), 3.3(s, 3H, OCH₂CH₂OMe), 3.05(m, 1H, CHMe₂), 1.22(s, 6H, CHMe₂) | DMSO-d⁶ |
| 5-isopropyl-thiazol-2-yl amide with 4-chloro-3-sulfamoylbenzoyl | 230–231 | 12.81(s broad, 1H, NHCO), 8.63–7.79(m, 3H, Ar), 7.71(s, 2H, NH₂), 7.24(s, 1H, H4thiaz), 3.12 (m, 1H, CHMe₂), 1.27(d, 6H, CHMe₂) | DMSO-d⁶ |
| 5-isopropyl-thiazol-2-yl amide with 4-fluorobenzoyl | 181–182 | 12.47(s broad, 1H, NHCO), 8.13–7.37(m, 4H, Ar), 7.23(s, 1H, H4thiaz), 3.13(m, 1H, CHMe₂), 1.27(d, 6H, CHMe₂) | DMSO-d⁶ |

TABLE I-continued

| MOLSTRUCTURE | mp °C. | $^1$H-NMR | Solvent |
|---|---|---|---|
| (5-isopropylthiazol-2-yl)-NHCO-(3-nitrophenyl) | | 12.0(s broad, 1H, NHCO), 8.89–7.82(m, 4H, Ar), 7.27(s, 1H, H4thiaz), 3.13(m, 1H, CHMe$_2$), 1.28(d, 6H, CHMe$_2$) | DMSO-d$^6$ |
| (5-isopropylthiazol-2-yl)-NHCO-(2,4-dichloro-5-sulfamoylphenyl) | 263–264 | 12.74(s broad, 1H, NHCO), 8.11–8.0(2s, 2H, Ar), 7.82(s, 2H, NH$_2$), 7.24(s, 1H, H4thiaz), 3.15(m, 1H, CHMe$_2$), 1.27(d, 6H, CHMe$_2$) | DMSO-d$^6$ |
| (5-isopropylthiazol-2-yl)-NHCO-(4-chlorophenyl) | 204–206 | 12.6(s broad, 1H, NHCO), 8.06–7.60(m, 3H, Ar), 7.23(s, 1H, H4thiaz), 3.12(m, 1H, CHMe$_2$), 1.27(d, 6H, CHMe$_2$) | DMSO-d$^6$ |
| (5-isopropylthiazol-2-yl)-NHCO-(3-nitro-4-methylsulfonylphenyl) | 148–150 | 8.54–8.31(m, 3H, Ar), 6.98 (s, 1H, H4thiaz), 3.43(s, 3H, SO$_2$Me) 3.14(m, 1H, CHMe$_2$), 1.35 (d, 6H, CHMe$_2$) | CDCl$_3$ |
| (5-isopropylthiazol-2-yl)-NHCO-(4-methoxycarbonylphenyl) | 173–175 | 8.16–8.06(2d, 4H, Ar), 7.25 (s, 1H, H4thiaz), 3.88(s, 3H, COOMe), 3.14(m, 1H, CHMe$_2$), 1.28 (d, 6H, CHMe$_2$) | DMSO-d$^6$ |
| (5-isopropylthiazol-2-yl)-NHCO-(2-chloro-5-nitrophenyl) | 164–166 | 8.50–7.86(m, 3H, Ar), 7.24 (s, 1H, H4thiaz), 3.15(m, 1H, CHMe$_2$), 1.28(d, 6H, CHMe$_2$) | DMSO-d$^6$ |
| (5-isopropylthiazol-2-yl)-NHCO-(3-chloro-4-(4-methylpiperazin-1-yl)phenyl) | 178–179 | 12.4(s broad, 1H, NHCO), 8.12–7.21(m, 3H, Ar), 7.22(s, 1H, H4thiaz), 3.2–2.48(m, 5H, CHMe$_2$+ piperazine), 2.22(s, 3H, NMe), 1.27(d, 6H, CHMe$_2$) | DMSO-d$^6$ |

TABLE I-continued

| MOLSTRUCTURE | mp °C. | ¹H-NMR | Solvent |
|---|---|---|---|
| (isopropyl-thiazole-NHCO-2,5-dichlorophenyl) | | 12.6(s broad, 1H, NHCO), 7.73–7.57(m, 3H, Ar), 7.22(s, 1H, H4thiaz), 3.15(m, 1H, CHMe₂), 1.27(d, 6H, CHMe₂) | DMSO-d⁶ |
| (isopropyl-thiazole-NHCO-phenyl-COMe) | | 12.6(s broad, 1H, NHCO), 8.16–8.05(m, 4H, Ar), 7.24(s, 1H, H4thiaz), 3.13(m, 1H, CHMe₂), 2.62(s, 3H, COMe), 1.28(d, 6H, CHMe₂) | DMSO-d⁶ |
| (isopropyl-thiazole-NHCO-CH₂-indol-3-yl) | 207–209 | 9.4(s broad, 1H, NHCO), 8.3(s, 1H, NH), 7.55–6.98(m, 6H, indole+H4thiaz), 3.96(s, 2H, COCH₂), 3.10(m, 1H, CHMe₂), 1.30 (d, 6H, CHMe₂) | CDCl₃ |
| (isopropyl-thiazole-NHCO-CH₂-thiophen-3-yl) | 116–118 | 9.80(s broad, 1H, NHCO), 7.37–7.05(m, 3H, Ar), 7.04(d, 1H, H4thiaz), 3.84(s, 2H, COCH₂), 3.11 (m, 1H, CHMe₂), 1.32(d, 6H, CHMe₂) | CDCl₃ |
| (isopropyl-thiazole-NHCO-CH₂-thiophen-2-yl) | 148–150 | 10.20(s broad, 1H, NHCO), 7.28–7.01(m, 4H, Ar+H4thiaz), 4.02 (s, 2H, COCH₂), 3.13(m, 1H, CHMe₂), 1.32(d, 6H, CHMe₂) | CDCl₃ |
| (isopropyl-thiazole-NH-CO-CH₂-(2-methylindol-3-yl)) | 170–172 | 12.05(s broad, 1H, NHCO), 10.82 (s, 1H, NH), 7.48–6.90(m, 5H, indole+H4thiaz), 3.74(s, 2H, COCH₂), 3.06(m, 1H, CHMe₂), 2.36 (s, 3H, Me), 1.21(d, 6H, CHMe₂) | DMSO-d⁶ |

| MOLSTRUCTURE | mp ° C. | ¹H-NMR | Solvent |
|---|---|---|---|
| | 163–165 | 12.07(s broad, 1H, NHCO), 7.57–7.01(m, 6H, indole+H4thiaz), 3.79(s, 2H, COCH₂), 3.74(s, 3H, NMe), 3.05(m, 1H, CHMe₂), 1.21 (d, 6H, CHMe₂) | DMSO-d⁶ |
| | 155–157 | 10.20(s broad, 1H, NHCO), 7.88–7.40(m, 5H, Ar), 6.95(s, 1H, H4thiaz), 4.04(s, 2H, COCH₂), 3.07 (m, 1H, CHMe₂), 1.27(d, 6H, CHMe₂) | DMSO-d⁶ |
| | 234–236 | 11.3(s broad, 1H, NHCO), 7.52–6.28(m, 5H, Ar+H4thiaz), 3.93 (s, 2H, COCH₂), 3.87(s, 3H, OMe), 3.10(m, 1H, CHMe₂), 1.27(d, 6H, CHMe₂) | DMSO-d⁶ |
| | 161–163 | 12.19(s, 1H, NHCO), 8.49–7.34 (m, 4H, Ar), 7.12(s, 1H, H4thiaz), 2.56(d, 2H, CH₂iPr), 1.75(m, 1H, CHMe₂), 0.86(d, 6H, CHMe₂) | DMSO-d⁶ |
| | 166–168 | 12.20(s, 1H, NHCO), 8.48–7.24 (m, 10H, 2Xar+H4thiaz), 4.06(s, 2H, CH₂Ph), 3.77(s, 2H, CH₂CO) | DMSO-d⁶ |
| | 164–167 | 8.63–7.9(m, 5H, Ar), 7.11(s, 1H, H4thiaz), 3.85(s, 2H, COCH₂), 3.15(m, 1H, CHMe₂), 1.29(d, 6H, CHMe₂) | CDCl3 |
| | | 11.6(s broad, 1H, NHCO), 7.10 (s, 1H, H4thiaz), 3.67(s, 3H, CH₃OCO), 3.15(m, 1H, CHMe₂), 2.60(m, 2H, CH₂CH₂CH₂), 2.46(m, 2H, CH₂CH₂CH₂), 2.09(m, 2H, CH₂CH₂CH₂), 1.34(d, 6H, CHMe₂) | CDCl₃ |

TABLE I-continued

| MOLSTRUCTURE | mp °C. | ¹H-NMR | Solvent |
|---|---|---|---|
| [5-isopropylthiazol-2-yl amide of 4-phenyl-3-butenoic acid] | 114–117 | 10.6(s broad, 1H, NHCO), 7.36 (m, 5H, Ar), 7.10(s, 1H, H4thiaz), 6.61(d, 1H, J=15.8, CH=CHPh), 6.36(dt, 1H, J=15.8, 7.3, CH=CHPh), 3.43(dd, 2H, J=7.3, 1.3, COCH$_2$), 3.14(m, 1H, CHMe$_2$), 1.33(d, 6H, CHMe$_2$) | CDCl$_3$ |
| [5-isopropylthiazol-2-yl amide of (5-bromoindol-3-yl)acetic acid] | 217–220 | 12.09(s broad, 1H, NHCO), 11.5 (s, 1H, NH), 7.78–7.16(m, 4H, indole), 7.13(s, 1H, H4thiaz), 3.78(s, 2H, COCH$_2$), 3.07(m, 1H, CHMe$_2$), 1.21(d, 6H, CHMe$_2$) | DMSO-d$^6$ |
| [5-isopropylthiazol-2-yl amide of (5-fluoroindol-3-yl)acetic acid] | 222–225 dec. | 12.07(s, 1H, NHCO), 11.03(s, 1H, NH), 7.3–6.80(m, indole+ H4thiaz), 3.77(s, 2H, COCH$_2$), 3.06(m, 1H, CHMe$_2$), 1.22(d, 6H, CHMe$_2$) | DMSO-d$^6$ |
| [5-isopropylthiazol-2-yl amide of (5-chlorobenzothiophen-3-yl)acetic acid] | 172–173 | 12.25(s, 1H, NHCO), 8.02–7.4(m, 4H, Ar), 7.15(s, 1H, H4thiaz), 4.0(s, 2H, COCH$_2$), 3.07(m, 1H, CHMe$_2$), 1.22(d, 6H, CHMe$_2$) | DMSO-d$^6$ |
| [5-isopropylthiazol-2-yl amide of (5-methoxyindol-3-yl)acetic acid] | 203–204 | 12.05(s, 1H, NHCO), 10.77(s, 1H, NH), 7.22–6.70(m, 5H, indole+H4thiaz), 3.75(s, 2H, COCH$_2$), 3.72(s, 3H, OMe), 3.07 (m, 1H, CHMe$_2$), 1.22(d, 6H, CHMe$_2$) | DMSO-d$^6$ |
| [5-isopropylthiazol-2-yl amide of 3-(indol-3-yl)propanoic acid] | 163–164 | 12.89(s, 1H, NHCO), 10.75(s, 1H, NH), 7.12–6.97(m, 5H, indole+H4thiaz), 3.10(m, 1H, CHMe$_2$), 3.01(t, 2H, CH$_2$CH$_2$CO), 2.78(t, 2H, CH$_2$CH$_2$CO), 1.25(d, 6H, CHMe$_2$) | DMSO-d$^6$ |
| [5-isopropylthiazol-2-yl amide of 2,6-dichloronicotinic acid] | 186–187 | 12.7(s broad, 1H, NHCO), 8.18 (d, 1H, J=7.8, Ar), 7.71(d, 1H, J=7.8, Ar), 7.24(s, 1H, H4thiaz), 3.15(m, 1H, CHMe$_2$), 1.27(d, 6H, CHMe$_2$) | DMSO-d$^6$ |

TABLE I-continued

| MOLSTRUCTURE | mp °C. | ¹H-NMR | Solvent |
|---|---|---|---|
| | | 10.8(s broad, 1H, N<u>H</u>CO), 7.45 (s, 1H, H4thiaz), 3.33(m, 1H, C<u>H</u>Me₂), 2.54(m, 2H, C<u>H</u>₂CHMe₂), 2.42(m, 1H, CH₂C<u>H</u>Me₂), 1.53(d, 6H, CH₂CH<u>Me</u>₂), 1.21(d, 6H, CH<u>Me</u>₂) | CDCl₃ |
| | | 12.4(s broad, 1H, N<u>H</u>CO), 8.05–7.51(m, 5H, Ph), 7.23(s, 1H, H4thiaz), 3.13(m, 1H, C<u>H</u>Me₂), 1.28(d, 6H, CH<u>Me</u>₂) | DMSO-d⁶ |
| | | 11.8(s broad, 1H, N<u>H</u>CO), 7.11 (s, 1H, H4thiaz), 3.08(m, 1H, C<u>H</u>Me₂), 2.25(d, 2H, C<u>H</u>₂CO), 2.42 (m, 1H, CH₂C<u>H</u>Me₂), 1.23(d, 6H, CH<u>Me</u>₂), 1.8–0.8(m, 11H, cyclohexyl) | DMSO-d⁶ |
| | | 8.13(d, 1H, H3fur), 7.84(d, 1H, H5fur), 7.25(d, 1H, H4thiaz), 6.69(dd, 1H, H4fur), 7.45(s, 1H, H4thiaz), 3.20(m, 1H, C<u>H</u>Me₂), 1.39(d, 6H, CH<u>Me</u>₂) | CDCl₃ |
| | | 12.7(s broad, 1H, N<u>H</u>CO), 7.54–6.82(m, 3H, H4thiaz+furane), 3.10(m, 1H, C<u>H</u>Me₂), 1.26(d, 6H, CH<u>Me</u>₂), | DMSO-d⁶ |

What is claimed is:

1. A compound which is a 2-amino-1,3-thiazole derivative of formula (I)

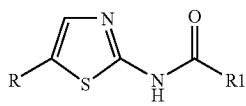

wherein R is isopropyl;
$R_1$ is an optionally further substituted group selected from:
i) straight or branched $C_1$–$C_8$ alkyl or $C_2$–$C_6$ alkenyl;
ii) 3 to 6 membered carbocycle or 5 to 7 membered heterocycle ring;
iii) aryl or arylcarbonyl;
iv) arylalkyl with from 1 to 8 carbon atoms within the straight or branched alkyl chain;
v) arylalkenyl with from 2 to 6 carbon atoms within the straight or branched alkenyl chain;
vi) an optionally protected amino acid residue; or a pharmaceutically acceptable salt thereof.

2. A compound of formula (I), according to claim 1, wherein $R_1$ is an optionally substituted group selected from straight or branched $C_1$–$C_4$ alkyl or alkenyl, aryl or arylalkyl with from 1 to 4 carbon atoms within the alkyl chain or it is an optionally protected amino acid residue.

3. A process for producing a compound of formula (I), as defined in claim 1, which process comprises reacting a compound of formula (II)

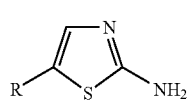

with a compound of formula (III)

(III)

wherein R and R$_1$ are as defined in claim 1 and X is hydroxy or a suitable leaving group; and, if desired, converting a 2-amino-1,3-thiazole derivative of formula (I) into another such derivative of formula (I), and/or into a salt thereof.

4. A process according to claim 3 wherein X is hydroxy, bromine or chlorine.

5. A pharmaceutical composition comprising one or more pharmaceutically acceptable carriers and/or diluents and, as the active principle, an effective amount of a compound of formula (I) as defined in claim 1.

6. A compound of formula (I) according to claim 1, whenever appropriate in the form of a pharmaceutically acceptable salt, selected from the group consisting of:

N-(5-isopropyl-1,3-thiazol-2-yl)-2-(3-hydroxyphenyl)acetamide;
N-(5-isopropyl-1,3-thiazol-2-yl)-2-(3-methoxyphenyl)acetamide;
N-(5-isopropyl-1,3-thiazol-2-yl)-2-(3-chlorophenyl)acetamide;
N-(5-isopropyl-1,3-thiazol-2-yl)-2-(4-hydroxyphenyl)acetamide;
N-(5-isopropyl-1,3-thiazol-2-yl)-2-(3,4-dihydroxyphenyl)acetamide;
N-(5-isopropyl-1,3-thiazol-2-yl)-2-(4-hydroxy-3-methoxyphenyl)acetamide;
N-(5-isopropyl-1,3-thiazol-2-yl)-2-(4-methoxyphenyl)acetamide;
N-(5-isopropyl-1,3-thiazol-2-yl)-2-(4-chlorophenyl)acetamide;
N-(5-isopropyl-1,3-thiazol-2-yl)-2-phenyl-acetamide;
N-(5-isopropyl-thiazol-2-yl)-4-sulfamoyl-benzamide;
N-(5-isopropyl-1,3-thiazol-2-yl)-butanamide;
2-[3-(3-chloropropoxy)phenyl]-N-(5-isopropyl-1,3-thiazol-2-yl)acetamide;
2-[3-(2-chloroethoxy)phenyl]-N-(5-isopropyl-1,3-thiazol-2-yl)acetamide;
2-(4-aminophenyl)-N-(5-isopropyl-1,3-thiazol-2-yl)acetamide;
4-amino-N-(5-isopropyl-1,3-thiazol-2-yl)benzamide;
2-(2-amino-1,3-thiazol-4-yl)-N-(5-isopropyl-1,3-thiazol-2-yl)acetamide;
N-(5-isopropyl-1,3-thiazol-2-yl)-2-{3-[3-(4-morpholinyl)propoxy]phenyl} acetamide;
N-(5-isopropyl-1,3-thiazol-2-yl)-2-{3-[3-(4-morpholinyl)ethoxy]phenyl}acetamide;
N-(5-isopropyl-1,3-thiazol-2-yl)-2-(3-[3-(1-pirrolidinyl)propoxy]phenyl)acetamide;
N-(5-isopropyl-1,3-thiazol-2-yl)-2-{3-[3-(4-methyl-1-piperazinyl)propoxy]phenyl}acetamide;
2-{3-[2-(dimethylamino)ethoxy]phenyl}-N-(5-isopropyl-1,3-thiazol-2-yl)acetamide;
2-{3-[3-(dimethylamino)propoxy]phenyl}-N-(5-isopropyl-1,3-thiazol-2-yl)acetamide;
N-(5-isopropyl-1,3-thiazol-2.-yl)-2-[3-(2-methoxyethoxy)phenyl]acetamide;
3-chloro-N-(5-isopropyl-1,3-thiazol-2-yl)-4-(4-methylpiperazinyl)benzamide;
2-anilino-N-(5-isopropyl-1,3-thiazol-2-yl)acetamide;
(R)-N-(5-isopropyl-1,3-thiazol-2-yl)-2-phenylpropanamide;
(S)-N-(5-isopropyl-1,3-thiazol-2-yl)-2-phenylpropanamide;
N-(5-isopropyl-1,3-thiazol-2-yl)benzamide;
2,5-dichloro-N-(5-isopropyl-1,3-thiazol-2-yl)benzamide;
3,5-dichloro-N-(5-isopropyl-1,3-thiazol-2-yl)benzamide;
3,4-dichloro-N-(5-isopropyl-1,3-thiazol-2-yl)benzamide;
2,4-dichloro-N-(5-isopropyl-1,3-thiazol-2-yl)benzamide;
2,3-dichloro-N-(5-isopropyl-1,3-thiazol-2-yl)benzamide;
3-iodio-N-(5-isopropyl-1,3-thiazol-2-yl)benzamide;
2-iodio-N-(5-isopropyl-1,3-thiazol-2-yl)benzamide;
4-iodio-N-(5-isopropyl-1,3-thiazol-2-yl)benzamide;
3-bromo-N-(5-isopropyl-1,3-thiazol-2-yl)benzamide;
4-chloro-2-fluoro-N-(5-isopropyl-1,3-thiazol-2-yl)benzamide;
5-bromo-2-chloro-N-(5-isopropyl-1,3-thiazol-2-yl)benzamide;
3-chloro-N-(5-isopropyl-1,3-thiazol-2-yl)benzamide;
2-chloro-N-(5-isopropyl-1,3-thiazol-2-yl)benzamide;
4-chloro-N-(5-isopropyl-1,3-thiazol-2-yl)benzamide;
3-fluoro-N-(5-isopropyl-1,3-thiazol-2-yl)benzamide;
2-fluoro-N-(5-isopropyl-1,3-thiazol-2-yl)benzamide;
4-fluoro-N-(5-isopropyl-1,3-thiazol-2-yl)benzamide;
2,4-difluoro-N-(5-isopropyl-1,3-triazol-2-yl)benzamide;
3,4-difluoro-N-(5-isopropyl-1,3-thiazol-2-yl)benzamide;
2,3,4,5,6-pentafluoro-N-(5-isopropyl-1,3-thiazol-2-yl)benzamide;
N-(5-isopropyl-1,3-thiazol-2-yl)-4-methyl-3-nitrobenzamide;
N-(5-isopropyl-1,3-thiazol-2-yl)-5-methyl-2-nitrobenzamide;
N-(5-isopropyl-1,3-thiazol-2-yl)-3-methyl-2-nitrobenzamide;
N-(5-isopropyl-1,3-thiazol-2-yl)-3,5-dimethyl-4-nitrobenzamide;
N-(5-isopropyl-1,3-thiazol-2-yl)-4-methoxy-2-nitrobenzamide;
N-(5-isopropyl-1,3-thiazol-2-yl)-3-methoxy-2-nitrobenzamide;
N-(5-isopropyl-1,3-thiazol-2-yl)-4-methoxy-3-nitrobenzamide;
N-(5-isopropyl-1,3-thiazol-2-yl)-3-methoxy-4-nitrobenzamide;
N-(5-isopropyl-1,3-thiazol-2-yl)-3,5-dinitrobenzamide;
5-{[(5-isopropyl-1,3-thiazol-2-yl)amino]carbonyl}-2-nitrophenyl octanoate;
N-(5-isopropyl-1,3-thiazol-2-yl)-3-nitrobenzamide;
N-(5-isopropyl-1,3-thiazol-2-yl)-2-nitrobenzamide;
N-(5-isopropyl-1,3-thiazol-2-yl)-4-nitrobenzamide;
N-(5-isopropyl-1,3-thiazol-2-yl)-4-(methylsulfonyl)-3-nitrobepzamide;
4-chloro-N-(5-isopropyl-1,3-thiazol-2-yl)-3-nitrobenzamide;
6-chloro-N-(5-isopropyl-1,3-thiazol-2-yl)-3-nitrobenzamide;
4-chloro-N-(5-isopropyl-1,3-thiazol-2-yl)-2-nitrobenzamide;
2-chloro-N-(5-isopropyl-1,3-thiazol-2-yl)-4-nitrobenzamide;
5-chloro-N-(5-isopropyl-1,3-thiazol-2-yl)-2-nitrobenzamide;
2-bromo-N-(5-isopropyl-1,3-thiazol-2-yl)-5-nitrobenzamide;
4-fluoro-N-(5-isopropyl-1,3-thiazol-2-yl)-3-nitrobenzamide;
4-fluoro-N-(5-isopropyl-1,3-thiazol-2-yl)-2-nitrobenzamide;
N-(5-isopropyl-1,3-thiazol-2-yl)-2-nitro-4-(trifluoromethyl)benzamide;
N-(5-isopropyl-1,3-thiazol-2-yl)-3,5-bis(trifluoromethyl)benzamide;

N-(5-isopropyl-1,3-thiazol-2-yl)-2,6-bis(trifluoromethyl)benzamide;
N-(5-isopropyl-1,3-thiazol-2-yl)-2-(trifluoromethyl)benzamide;
N-(5-isopropyl-1,3-thiazol-2-yl)-3-(trifluoromethyl)benzamide;
3-fluoro-N-(5-isopropyl-1,3-thiazol-2-yl)-4-(trifluoromethyl)benzamide;
2-fluoro-N-(5-isopropyl-1,3-thiazol-2-yl)-3-(trifluoromethyl)benzamide;
5-fluoro-N-(5-isopropyl-1,3-thiazol-2-yl)-3-(trifluoromethyl)benzamide;
2-fluoro-N-(5-isopropyl-1,3-thiazol-2-yl)-4-(trifluoromethyl)benzamide;
4-fluoro-N-(5-isopropyl-1,3-thiazol-2-yl)-3-(trifluoromethyl)benzamide;
methyl 4-([(5-isopropyl-1,3-thiazol-2-yl)amino]carbonyl}benzoate;
methyl 2-([(5-isopropyl-1,3-thiazol-2-yl)amino]carbonyl)benzoate;
4-cyano-N-(5-isopropyl-1,3-thiazol-2-yl)benzamide;
3-cyano-N-(5-isopropyl-1,3-thiazol-2-yl)benzamide;
N-(5-isopropyl-1,3-thiazol-2-yl)-3-methylbenzamide;
N-(5-isopropyl-1,3-thiazol-2-yl)-2-methylbenzamide;
N-(5-isopropyl-1,3-thiazol-2-yl)-4-methylbenzamide;
N-(5-isopropyl-1,3-thiazol-2-yl)-4-vinylbenzamide;
N-(5-isopropyl-1,3-thiazol-2-yl)-4-(2-phenylethynyl)benzamide;
N-(5-isopropyl-1,3-thiazol-2-yl)-3-methoxy-4-methylbenzamide;
2-benzyl-N-(5-isopropyl-1,3-thiazol-2-yl)benzamide;
N-(5-isopropyl-1,3-thiazol-2-yl)-2-phenethylbenzamide;
N-(5-isopropyl-1,3-thiazol-2-yl)-2-phenylbenzamide;
N-(5-isopropyl-1,3-thiazol-2-yl)-4-phenylbenzamide;
4-(tert-butyl)-N-(5-isopropyl-1,3-thiazol-2-yl)benzamide;
N-(5-isopropyl-1,3-thiazol-2-yl)-4-isopropylbenzamide;
N-(5-isopropyl-1,3-thiazol-2-yl)-4-pentylbenzamide;
3-fluoro-N-(5-isopropyl-1,3-thiazol-2-yl)-4-methylbenzamide;
N-(5-isopropyl-1,3-thiazol-2-yl)-3,4-dimethylbenzamide;
N-(5-isopropyl-1,3-thiazol-2-yl)-3,5-dimethylbenzamide;
4-acetyl-N-(5-isopropyl-1,3-thiazol-2-yl)benzamide;
N-(5-isopropyl-1,3-thiazol-2-yl)-4-(methylsulfonyl)benzamide;
5-(aminosulfonyl)-2,4-dichloro-N-(5-isopropyl-1,3-thiazol-2-yl)benzamide;
5-(aminosulfonyl)-4-chloro-N-(5-isopropyl-1,3-thiazol-2-yl)benzamide;
3-fluoro-N-(5-isopropyl-1,3-thiazol-2-yl)-4-methoxybenzamide;
3-chloro-N-(5-isopropyl-1,3-thiazol-2-yl)-4-methoxybenzamide;
5-chloro-N-(5-isopropyl-1,3-thiazol-2-yl)-2-methoxybenzamide;
N-(5-isopropyl-1,3-thiazol-2-yl)-4-methoxybenzamide;
N-(5-isopropyl-1,3-thiazol-2-yl)-3-methoxybenzamide;
N-(5-isopropyl-1,3-thiazol-2-yl)-2-methoxybenzamide;
N-(5-isopropyl-1,3-thiazol-2-yl)-3,4-dimethoxybenzamide;
N-(5-isopropyl-1,3-thiazol-2-yl)-3,5-dimethoxybenzamide;
N-(5-isopropyl-1,3-thiazol-2-yl)-2,4-dimethoxybenzamide;
N-(5-isopropyl-1,3-thiazol-2-yl)-2,3-dimethoxybenzamide;
N-(5-isopropyl-1,3-thiazol-2-yl)-3-phenoxybenzamide;
N-(5-isopropyl-1,3-thiazol-2-yl)-2-phenoxybenzamide;
N-(5-isopropyl-1,3-thiazol-2-yl)-4-phenoxybenzamide;
2-ethoxy-N-(5-isopropyl-1,3-thiazol-2-yl)benzamide;
4-ethoxy-N-(5-isopropyl-1,3-thiazol-2-yl)benzamide;
N-(5-isopropyl-1,3-thiazol-2-yl)-3,4,5-trimethoxybenzamide;
3,4-diethoxy-N-(5-isopropyl-1,3-thiazol-2-yl)benzamide;
3,4,5-triethoxy-N-(5-isopropyl-1,3-thiazol-2-yl)benzamide;
N-(5-isopropyl-1,3-thiazol-2-yl)-3-methoxy-4-(methoxymethoxy)benzamide;
4-butoxy-N-(5-isopropyl-1,3-thiazol-2-yl)benzamide;
N-(5-isopropyl-1,3-thiazol-2-yl)-4-propoxybenzamide;
4-isopropoxy-N-(5-isopropyl-1,3-thiazol-2-yl)benzamide;
N-(5-isopropyl-1,3-thiazol-2-yl)-1,3-benzodioxole-5-carboxamide;
4-(benzyloxy)-N-(5-isopropyl-1,3-thiazol-2-yl)benzamide;
4-(2-cyclohexen-1-yloxy)-N-(5-isopropyl-1,3-thiazol-2-yl)benzamide;
N-(5-isopropyl-1,3-thiazol-2-yl)-4(trifluoromethoxy)benzamide;
4-(difluoromethoxy)-N-(5-isopropyl-1,3-thiazol-2-yl)benzamide;
N-(5-isopropyl-1,3-thiazol-2-yl)-4(methylsulfanyl)benzamide;
2-[(4-chlorophenyl)sulfinyl)-N-(5-isopropyl-1,3-thiazol-2-yl)benzamide;
N-(5-isopropyl-1,3-thiazol-2-yl)-2-[(4-nitrophenyl)sulfinyl]benzamide;
N-(5-isopropyl-1,3-thiazol-2-yl)-4-[(4-methylphenyl)sulfonyl]-3-nitrobenzamide;
N-(5-isopropyl-1,3-thiazol-2-yl)-3 [(trifluoromethyl)sulfanyl]benzamide;
N-(5-isopropyl-1,3-thiazol-2-yl)-2-methoxy-4-(methylsulfanyl)benzamide;
2-[(2-cyanophenyl)sulfanyl]-N-(5-isopropyl-1,3-thiazol-2-yl)benzamide;
N-1,N-1-diethyl-3,6-difluoro-N-2-(5-isopropyl-1,3-thiazol-2-yl)phthalamide;
4-formyl-N-(5-isopropyl-1,3-thiazol-2-yl)benzamide;
2-formyl-N-(5-isopropyl-1,3-thiazol-2-yl)benzamide;
4-{[(2,5-dimethoxyanilino)carbonyl]amino}-N-(5-isopropyl-1,3-thiazol-2-yl)benzamide;
4-(hydroxymethyl)-N-(5-isopropyl-1,3-thiazol-2-yl)benzamide;
4-{[(5-isopropyl-1,3-thiazol-2-yl)amino]carbonyl}-2-nitrobenzyl acetate;
4-{[(5-isopropyl-1,3-thiazol-2-yl)amino]carbonyl}-2-nitrobenzyl 4-(acetylamino)-3-iodobenzoate;
4-(acetylamino)-N-(5-isopropyl-1,3-thiazol-2-yl)benzamide;
N-(5-isopropyl-1,3-thiazol-2-yl)-4-[(2-phenylacetyl)amino]benzamide;
4-(acetylamino)-3-iodo-N-(5-isopropyl-1,3-thiazol-2-yl)benzamide;
4-amino-N-(5-isopropyl-1,3-thiazol-2-yl)benzamide;
4-(dimethylamino)-N-(5-isopropyl-1,3-thiazol-2-yl)benzamide;
3-(dimethylamino)-N-(5-isopropyl-1,3-thiazol-2-yl)benzamide;
2-(methylamino)-N-(5-isopropyl-1,3-thiazol-2-yl)benzamide;
N-(5-isopropyl-1,3-thiazol-2-yl)-2-[3-(trifluoromethyl)anilino]benzamide;

3-{[(5-bromo-1,3-dioxo-1,3-dihydro-2H-isoindol-2-yl) methyl]amino}-N-(5-isopropyl-1,3-thiazol-2-yl)benzamide;
N-(5-isopropyl-1,3-thiazol-2-yl)-4-(1H-pyrrol-1-yl)benzamide;
2,6-dichloro-N-(5-isopropyl-1,3-thiazol-2-yl)isonicotinamide;
2-(4-bromophenyl)-6-(4-iodophenyl)-N-(5-isopropyl-1,3-thiazol-2-yl)isonicotinamide;
N-(5-isopropyl-1,3-thiazol-2-yl)-2-[3-(trifluoromethyl) anilino)nicotinamide;
2,6-dichloro-N-(5-isopropyl. 1,3-thiazol-2-yl)nicotinamide;
5,6-dichloro-N-(5-isopropyl-1,3-thiazol-2-yl)nicotinamide;
2-chloro-N-(5-isopropyl-1,3-thiazol-2-yl)-6-methylnicotinamide;
2,6-dichloro-5-fluoro-N-(5-isopropyl-1,3-thiazol-2-yl) nicotinamide;
N-(5-isopropyl-1,3-thiazol-2-yl)-2-phenoxynicotinamide;
N-(5-isopropyl-1,3-thiazol-2-yl)-6-(2,2,2-trifluoroethoxy)nicotinamide;
N-(5-isopropyl-1,3-thiazol-2-yl)-2,6-dimethoxynicotinamide;
N-(5-isopropyl-1,3-thiazol-2-yl)-2-quinoxalinecarboxamide;
N-(5-isopropyl-1,3-thiazol-2-yl)-5-methyl-2-pyrazinecarboxamide;
N-(5-isopropyl-1,3-thiazol-2-yl)-8-quinolinecarboxamide;
N-(5-isopropyl-1,3-thiazol-2-yl)-2-phenyl-4-quinolinecarboxamjde;
N-(5-isopropyl-1,3-thiazol-2-yl)-5-methyl-1-phenyl-1H-pyrazole-4-carboxamide;
N-(5-isopropyl-1,3-thiazol-2-yl)-5-methyl-1H-pyrazole-3-carboxamide;
N-(5-isopropyl-1,3-thiazol-2-yl)-1H-pyrazole-4-carboxamide;
N-(5-isopropyl-1,3-thiazol-2-yl)-5-methyl-2-phenyl-2H-1,2,3-triazole-4-carboxamide;
2-[(2,1,3-benzoxadiazol-5-yloxy)methyl]-N-(5-isopropyl-1,3-thiazol-2-yl)-4-methyl-1,3-thiazole-5-carboxamide;
N-(5-isopropyl-1,3-thiazol-2-yl)-9H-fluorene-1-carboxamide;
N-(5-isopropyl-1,3-thiazol-2-yl)-7-methoxy-1-benzofrran2-carboxide;
N-(5-isopropyl-1,3-thiazol-2-yl)-1-[(4-methylphenyl)sulfonyl]-1H-pyrrole-3-carboxamide;
2-ethoxy-N-(5-isopropyl-1,3-thiazol-2-yl)-1-naphthamide;
4-fluoro-N-(5-isopropyl-1,3-thiazol-2-yl)-1-naphthamide;
N-(5-isopropyl-1,3-thiazol-2-yl)-2-naphthamide;
N-(5-isopropyl-1,3-thiazol-2-yl)-9,10-dioxo-9,10-dihydro-2-anthracenecarboxamide;
N-(5-isopropyl-1,3-thiazol-2-yl)-9-oxo-9H-fluorene-4-carboxamide;
N-(5-isopropyl-1,3-thiazol-2-yl)-9-oxo-9H-fluorene-1-carboxamide;
N-(5-isopropyl-1,3-thiazol-2-yl)-8-oxo-5,6,7,8-tetrahydro-2-naphthalenecarboxarmde;
N-(5-isopropyl-1,3-thiazol-2-yl)-1,3-dioxo-1,3-dihydro-2-benzofuran-5-carboxamide;
N-(5-isopropyl-1,3-thiazol-2-yl)-1H-indole-5-carboxamide;
N-(5-isopropyl-1,3-thiazol-2-yl)-1H-indole-4-carboxamide;
N-(5-isopropyl-1,3-thiazol-2-yl)-1-methyl-2-phenyl-1H-indole-5-carboxamide;
2-butyl-N-(5-isopropyl-1,3-thiazol-2-yl)-1-methyl-1H-indole-5-carboxamide;
N-(5-isopropyl-1,3-thiazol-2-yl)-1H-indole-6-carboxamide;
N-(5-isopropyl-1,3-thiazol-2-yl)-5-methoxy-1H-indole-2-carboxamide;
1-allyl-2-butyl-N-(5-isopropyl-1,3-thiazol-2-yl)-1H-indole-5-carboxamide;
N-(5-isopropyl-1,3-thiazol-2-yl)-1-methyl-1H-indole-2-carboxamide;
1-benzyl-N-(5-isopropyl-1,3-thiazol-2-yl)-2-phenyl-1H-indole-5-carboxamide;
N-(5-isopropyl-1,3-thiazol-2-yl)-1H-1,2,3-benzotriazole-5-carboxamide;
N-(5-isopropyl-1,3-thiazol-2-yl)-3,5-dimethyl-4-isoxazo 1-carboxamide;
N-(5-isopropyl-1,3-thiazol-2-yl)-3-thiophenecarboxamide;
N-(5-isopropyl-1,3-thiazol-2-yl)-3-methyl-2-thiophenecarboxarmde;
N-(5-isopropyl-1,3-thiazol-2-yl)-5-methyl-2-thiophenecarboxamide;
5-bromo-N-(5-isopropyl-1,3-thiazol-2-yl)-2-thiophenecarboxamide;
N-(5-isopropyl-1,3-thiazol-2-yl)-3-[(2,3,3-trichloroacryloyl)amino]-2-thiophenecarboxamide;
5-bromo-N-(5-isopropyl-1,3-thiazol-2-yl)-2-furamide;
N-(5-isopropyl-1,3-thiazol-2-yl)-2-furamide;
N-(5-isopropyl-1,3-thiazol-2-yl)-5-(4-nitrophenyl)-2-furamide;
N-(5-isopropyl-1,3-thiazol-2-yl)-5-(2-nitrophenyl)-2-furamide;
5-(4-chlorophenyl)-N-(5-isopropyl-1,3-thiazol-2-yl)-2-furamide;
N-(5-isopropyl-1,3-thiazol-2-yl)-5-[3-(trifluoromethyl) phenyly2ffiramide;
5-(4-chloro-2-nitrophenyl)-N-(5-isopropyl-1,3-thiazol-2-yl)-2-furamide;
N-(5-isopropyl-1,3-thiazol-2-yl)-5-(4-methyl-2-nitrophenyl)-2-furamide;
5-[2-chloro-5-(trifluoromethyl)phenyl-N-(5-isopropyl-1,3-thiazol-2-yl)-2-furamide;
tert-butyl (1R)-2-[(5-isopropyl-1,3-thiazol-2-yl)amino]-2-oxo-1-phenylethylcarbamate;
(1R)-2-[(5-isopropyl-1,3-thiazol-2-yl)amino]-2-oxo-1-phenylethyl acetate;
(1S)-2-[(5-isopropyl-1,3-thiazol-2-yl)amino]-2-oxo-1-phenylethyl acetate;
(R,S)-2-fluoro-N-(5-isopropyl-1,3-thiazol-2-yl)-2-phenylacetamide;
(R)-2-fluoro-N-(5-isopropyl-1,3-thiazol-2-yl)-2-phenylacetamide;
(S)-2-fluoro-N-(5-isopropyl-1,3-thiazol-2-yl)-2-phenylacetamide;
2-(acetylamino)-N-(5-isopropyl-1,3-thiazol-2-yl)-2-phenylacetamide;
(R,S)-2-(methoxy)-N-(5-isopropyl-1,3-thiazol-2-yl)-2-phenylacetamide;
(R)-2-(methoxy)-N-(5-isopropyl-1,3-thiazol-2-yl)-2-phenylacetamide;
(S)-2-(methoxy)-N-(5-isopropyl-1,3-thiazo]-2-yl)-2-phenylacetamide;

3,3,3-trifluoro-N-(5-isopropyl-1,3-thiazol-2-yl)-2-methoxy-2-phenylpropanamide;
N-(5-isopropyl-1,3-thiazol-2-yl)-2-(1-naphthyl)acetamide;
N-(5-isopropyl-1,3-thiazol-2-yl)-2-(2-naphthyl)acetamide;
2-(1H-indol-3-yl)-N-(5-isopropyl-1,3-thiazol-2-yl)acetamide;
2-(1,3-benzodioxol-4-yl)-N-(5-isopropyl-1,3-thiazol-2-yl)acetamide;
2-(2,4-dinitrophenyl)-N-(5-isopropyl-1,3-thiazol-2-yl)acetamide;
N-(5-isopropyl-1,3-thiazol-2-yl)-2-(2-methyl-1H-indol-3-yl)acetamide;
N-(5-isopropyl-1,3-thiazol-2-yl)-2-(1-methyl-1H-indol-3-yl)acetamide;
N-(5-isopropyl-1,3-thiazol-2-yl)-2-(5-methoxy-1H-indol-3-yl)acetamide;
N-(5-isopropyl-1,3-thiazol-2-yl)-2-(5-benzyloxy-1H-indol-3-yl)acetamide;
N-(5-isopropyl-1,3-thiazol-2-yl)-2-(3-methoxy-2-methyl-1H-indol-3-yl)acetamide;
2-(1H-indol-3-yl)-N-(5-isopropyl-1,3-thiazol-2-yl)-0.2-oxoacetamide;
2-(5-bromo-1H-indol-3-yl)-N-(5-isopropyl-1,3-thiazol-2-yl)acetamide;
2-(5-fluoro-1H-indol-3-yl)-N-(5-isopropyl-1,3-thiazol-2-yl)acetamide;
2-[1-(4-chlorobenzoyl)-5-methoxy-2-methyl-1H-indol-3-yl]-N-(5-isopropyl-1,3-thiazol-2-yl)acetamide;
3-(1H-indol-3-yl)-N-(5-isopropyl-1,3-thiazol-2-yl)propanamide;
4-(1H-indol-3-yl)-N-(5-isopropyl-1,3-thiazol-2-yl)butanamide;
N-(5-isopropyl-1,3-thiazol-2-yl)-3-(2-thienyl)propanamide;
N-(5-isopropyl-1,3-thiazol-2-yl)-2-(2-thienyl)acetamide;
N-(5-isopropyl-1,3-thiazol-2-yl)-2-oxo-2-(2-thienyl)acetamide;
N-(5-isopropyl-1,3-thiazol-2-yl)-2-(3-thienyl)acetamide;
2-(5-chloro-1-benzothiophen-3-yl)-N-(5-isopropyl-1,3-thiazol-2-yl)acetamide;
2-(1-benzothiophen-3-yl)-N-(5-isopropyl-1,3-thiazol-2-yl)acetamide;
2-[2-(formylamino)-1,3-thiazol-4-yl]-N-(5-isopropyl-1,3-thiazol-2-yl)-2-(methoxyimino)acetamide;
2-{2-[(2-chloroacetyl)amino]-1,3-thiazol-4-yl}-N-(5-isopropyl-1,3-thiazol-2-yl)-2-(methoxyimino)acetamide;
2-chloro-N-(4-(2-[(5-isopropyl-1,3-thiazol-2-yl)amino]-2-oxoethyl}-1,3-thiazol-2-287.ethyl-2-({[2-[(5-isopropyl-1,3-thiazol-2-yl)amino]-2-oxo-1-(1H-pyrazol-3-yl)ethylidene]amino}oxy)acetate;
2-(2-furyl)-N-(5-isopropyl-1,3-thiazol-2-yl)-2-oxoacetamide;
2-(5-bromo-3-pyridinyl)-N-(5-isopropyl-1,3-thiazol-2-yl)acetamide;
N-(5-isopropyl-1,3-thiazol-2-yl)-2-(7-methoxy-2-oxo-2H-chromen-4-yl)acetamide;
N-(5-isopropyl-1,3-thiazol-2-yl)-4-phenyl-3-butenamide;
N-(5-isopropyl-1,3-thiazol-2-yl)-4-oxo-4-(4-methyl-phenyl)butanamide;
N-(5-isopropyl-1,3-thiazol-2-yl)-4-(4-nitrophenyl)butanamide;
N-(5-isopropyl-1,3-thiazol-2-yl)-4-phenylbutanamide;
benzyl 4-[(5-isopropyl-1,3-thiazol-2-yl)amino]-4-oxobutylcarbamatemethyl 5-[(5-isopropyl-1,3-thiazol-2-yl)amino]-5-oxopentanoate;
4-(1,3-dioxo-1,3-dihydro-2H-isoindol-2-yl)-N-(5-isopropyl-1,3-thiazol-2-yl)butanamide;
N-(5-isopropyl-1,3-thiazol-2-yl)-4-(4-methoxy-1-naphthyl)-4-oxobutanamide;
3-(2-chlorophenoxy)-N-(5-isopropyl-1,3-thiazol-2-yl)propanamide;
3-(4-methylphenoxy)-N-(5-isopropyl-1,3-thiazol-2-yl)propanamide;
3-cyclopentyl-N-(5-isopropyl-1,3-thiazol-2-yl)propanamide;
3-cyclohexyl-N-(5-isopropyl-1,3-thiazol-2-yl)propanamide;
N-(5-isopropyl-1,3-thiazol-2-yl)-4-methylpentanamide;
3-(4-chlorophenyl)-N-(5-isopropyl-1,3-thiazol-2-yl)propanamide;
3-(4-methoxyphenyl)-N-(5-isopropyl-1,3-thiazol-2-yl)propanamide;
3-chloro-N-(5-isopropyl-1,3-thiazol-2-yl)propanamide;
3-phenyl-N-(5-isopropyl-1,3-thiazol-2-yl)propanamide;
2-cyclohexyl-N-(5-isopropyl-1,3-thiazol-2-yl)acetamide;
N-(5-isopropyl-1,3-thiazol-2-yl)-3-methylbutanamide;
N-(5-isopropyl-1,3-thiazol-2-yl)-5-oxo-5-phenylpentanamide;
2-[(5-isopropyl-1,3-thiazol-2-yl)amino]-2-oxoyl-phenyl-ethyl acetate;
N-(5-isopropyl-1,3-thiazol-2-yl)-2-[4-(1-oxo-1,3-dihydro-2H-isoindol-2-yl)phenyl]propanamide;
1-(4-chlorophenyl)-N-(5-isopropyl-1,3-thiazol-2-yl)cyclopentanecarboxamide;
1-phenyl-N-(5-isopropyl-1,3-thiazol-2-yl)cyclopentanecarboxamide;
2-(3-bromo-4-methoxyphenyl)-N-(5-isopropyl 1,3-thiazol-2-yl)acetamide;
2-(2-nitro-4-trifluoromethylphenyl)-N-(5-isopropyl. 1,3-thiazol-2-yl)acetamide;
5-cyclohexyl 1-(4-{2-[(5-isopropyl-1,3-thiazol-2-yl)amino]-2-oxoethyl}benzyl)-(2S)-2-[(tert-butoxycarbonyl)amino]pentanedioate;
2-(5,6-dimethyl-1H-benzimidazol-1-yl)-.N-(5-isopropyl-1,3-thiazol-2-yl)acetamide;
2-[5-(4-chlorophenyl)-2H-1,2,3,4-tetraazol-2-yl]-N-(5-isopropyl-1,3-thiazol-2-yl)acetamide;
N-(5-isopropyl-1,3-thiazol-2-yl)-2-[5-(1-pyrrolidinyl)-2H-1,2,3,4-tetraazol-2-yl]acetamide;
N-(5-isopropyl-1,3-thiiazol-2-yl)-2-(3-methyl-1-benzothiophen-2-yl)acetamide;
N-(5-isopropyl-1,3-thiazol-2-yl)-4,4-bis(4-methylphenyl)-3-butenamide;
2-cyclopropyl-N-(5-isopropyl-1,3-thiazol-2-yl)acetamide;
N-{4-bromo-6-[(5-isopropyl-1,3-thiazol-2-yl)amino]-6-oxohexyl}benzamide;
2-cyclopentyl-N-(5-isopropyl-1,3-thiazol-2-yl)acetamide;
benzyl 6-[(5-isopropyl-1,3-thiazol-2-yl)amino)-6-oxohexylcarbamate;
N-1-(5-isopropyl-1,3-thiazol-2-yl)-N-4-(2-propynyl)-2-butenediamide;
4-(2,4-dimethylphenyl)-N-(5-isopropyl-1,3-thiazol-2-yl)-4-oxobutanamide;
4-(4-benzyloxyphenyl)-N-(5-isopropyl-1,3.-thiazol-2-yl)-4-oxobutanamide;
4-(thiphen-2-yl)-N-(5-isopropyl-1,3-thiazol-2-yl)-4-oxobutanamide;
benzyl 2-{[(benzyloxy)carbonyl]amino}-5-[(5-isopropyl-1,3-thiazol-2-yl)amino]-5-oxopentanoate;

4-(1H-indol-3-yl)-N-{3-[(5-isopropyl-1,3-thiazol-2-yl)amino]-3-oxopropyl}butanamide;
4-{[(5-isopropyl-1,3-thiazol-2-yl)amino]carbonyl}phenyl 4-chlorobenzenesulfonate;
N-(5-isopropyl-1,3-thiazol-2-yl)-4-{[(2-methoxyanilino)carbonyl)amino}benzamide;
4-{[2-(isopropylsulfonyl)acetyl]amino}-N-(5-isopropyl-1,3-thiazol-2-yl)benzamide;
N-(5-isopropyl-1,3-thiazol-2-yl)-4-{[2-(phenylsulfanyl)acetyl]amino}benzamide;
4-[(diethylamino)sulfonyl]-N-(5-isopropyl-1,3-thiazol-2-yl)benzamide;
2-bromo-N-(5-isopropyl-1,3-thiazol-2-yl)benzamide;
3,5-difluoro-N-(5-isopropyl-1,3-thiazol-2-yl)benzamide;
3-{[(2-fluoroanilino)carbonyl]amino}-N-(5-isopropyl-1,3-thiazol-2-yl)benzamide;
N-(5-isopropyl-1,3-thiazol-2-yl)-1-phenyl-5-propyl-1H-pyrazole-4-carboxamide;
3-chloro-4-(isopropylsulfonyl)-N-(s-isopropyl-t,3-thiazol-2-yl)-5-(methylsulfanyl)-2-thiophenecarboxamide;
3-iodo-4-(isopropylsulfonyl)-N-(5-isopropyl-1,3-thiazol-2-yl)-5-(methylsulfanyl)-2-thiophenecarboxamide;
2-{[(4-chlorophenyl)sulfonyl]methyl}-N-(5-isopropyl-1,3-thiazol-2-yl)-4-methyl-1,3-thiazole-5-carboxamide;
5-(4-chlorophenyl)-N-(5-isopropyl-1,3-thiazol-2-yl)-2-(trifluoromethyl)-3-furamide;
N-(5-isopropyl-1,3-thiazol-2-yl)-2-(2,3,4,5,6-pentafluorophenyl)acetamide;
N-(5-isopropyl-1,3-thiazol-2-yl)-2-(2-fluorophenyl)acetamide;
N-(5-isopropyl-1,3-thiazol-2-yl)-2-(2-bromophenyl)acetamide;
N-(5-isopropyl-1,3-thiazol-2-yl)-2-(2-chlorophenyl)acetamide;
N-(5-isopropyl-1,3-thiazol-2-yl)-2-(2-nitrophenyl) acetamide;
N-(5-isopropyl-1,3-thiazol-2-yl)-2-(2-trifluoromethylphenyl)acetamide;
N-(5-isopropyl-1,3-thiazol-2-yl)-2-(2-methoxyphenyl)acetamide;
N-(5-isopropyl-1,3-thiazol-2-yl)-2-(2,5-dimethoxyphenyl)acetamide;
N-(5-isopropyl-1,3-thiazol-2-yl)-2-(2,5-difluorophenyl)acetamide;
N-(5-isopropyl-1,3-thiazol-2-yl)-2-(3,4,5-trimethoxyphenyl)acetamide;
N-(5-isopropyl-1,3-thiazol-2-yl)-2-(2,6-dichlorophenyl)acetamide;
N-(5-isopropyl-1,3-thiazol-2-yl)-2-(2-chloro-6-fluorophenyl)acetamide;
N-(5-isopropyl-1,3-thiazol-2-yl)-2-(3,5-dimethoxyphenyl)acetamide;
N-(5-isopropyl-1,3-thiazol-2-yl)-2-(3,5-difluorophenyl)acetamide;
N-(5-isopropyl-1,3-thiazol-2-yl)-2-(2,5-bistrifluoromethylphenyl)acetamide;
N-(5-isopropyl-1,3-thiazol-2-yl)-2-(4-methylthiophenyl)acetamide;
N-(5-isopropyl-1,3-thiazol-2-yl)-2-(4-methoxyphenyl)acetamide;
N-(5-isopropyl-1,3-thiazol-2-yl)-2-(4-bromophenyl)acetamide;
N-(5-isopropyl-1,3-thiazol-2-yl)-2-(4-chlorophenyl)acetamide;
N-(5-isopropyl-1,3-thiazol-2-yl)-2-(4-fluorophenyl)acetamide;
N-(5-isopropyl-1,3-thiazol-2-yl)-2-(4-nitrophenyl)acetamide;
N-(5-isopropyl-1,3-thiazol-2-yl)-2-(4-trifluoromethylphenyl)acetamide;
N-(5-isopropyl-1,3-thiazol-2-yl)-2-(4-methylphenyl)acetamide;
N-(5-isopropyl-1,3-thiazol-2-yl)-2-(4-dimethylaminophenyl)acetamide;
2-[1,1'-biphenyl]-4-yl-N-(5-isopropyl-1,3-thiazol-2-yl)acetamide;
N-(5-isopropyl-1,3-thiazol-2-yl)-2-(3-trifluoromethylphenyl)acetamide;
N-(5-isopropyl-1,3-thiazol-2-yl)-2-(3-bromophenyl)acetamide;
N-(5-isopropyl-1,3-thiazol-2-yl)-2-(3-chlorophenyl)acetamide;
N-(5-isopropyl-1,3-thiazol-2-yl)-2-(3-nitrophenyl)acetamide;
N-(5-isopropyl-1,3-thiazol-2-yl)-2-(3-methoxyphenyl)acetamide;
N-(5-isopropyl-1,3-thiazol-2-yl)-2-(2,4-dinitrophenyl)acetamide;
N-(5-isopropyl-1,3-thiazol-2-yl)-2-(2,4-dichlorophenyl)acetamide;
N-(5-isopropyl-1,3-thiazol-2-yl)-2-(2,4-difluorophenyl)acetamide;
N-(5-isopropyl-1,3-thiazol-2-yl)-2-(4-benzyloxy-3-methoxyphenyl)acetamide;
N-(5-isopropyl-1,3-thiazol-2-yl)-2-(3,4-dichlorophenyl)acetamide;
N-(5-isopropyl-1,3-thiazol-2-yl)-2-(3,4-difluorophenyl)acetamide;
N-(5-isopropyl-1,3-thiazol-2-yl)-2-(3,4-dimethoxyphenyl)acetamide;
2-(2,3-dihydro-1H-inden-5-yl)-N-(5-isopropyl-1,3-thiazol-2-yl)acetamide;
N-(5-isopropyl-1,3-thiazol-2-yl)-1-phenylcyclopropanecarboxamide;
2-cyclopentyl-N-(5-isopropyl-1,3-thiazol-2-yl)-2-phenylacetamide;
2-cyclohexyl-N-(5-isopropyl-1,3-thiazol-2-yl)-2-phenylacetamide;
N-(5-isopropyl-1,3-thiazol-2-yl)-2,2-diphenylacetamide;
N-(5-isopropyl-1,3-thiazol-2-yl)-2-(2-nitrophenoxy)acetamide;
N-(5-isopropyl-1,3-thiazol-2-yl)-2-(4-nitrophenyl)propanamide;
N-(5-isopropyl-1,3-thiazol-2-yl)-2-phenyl)propanamide;
N-(5-isopropyl-1,3-thiazol-2-yl)-2-(4-isobutylphenyl)propanamide;
N-(5-isopropyl-1,3-thiazol-2-yl)-2-oxo-2-phenylacetamide;
N-(5-isopropyl-1,3-thiazol-2-yl)-3-methyl-2-phenylpentanamide;
(E,Z)-N-(5-isopropyl-1,3-thiazol-2-yl)-2-phenyl-2-butenamide;
N-(5-isopropyl-1,3-thiazol-2-yl)bicyclo[4.2.0]octa-1,3,5-triene-7-carboxamide;
N-(5-isopropyl-1,3-thiazol-2-yl)-3-oxo-1-indanecarboxamide;
N-(5-isopropyl-1,3-thiazol-2-yl)-2-phenyl)butanamide;
tert-butyl (1S)-2-[(5-isopropyl-1,3-thiazol-2-yl)amino]-1-methyl-2-oxoethylcarbamate;
tert-butyl (1S,2S)-1-{[(5-isopropyl-1,3-thiazol-2-yl)amino]carbonyl}-2-methylbutylcarbamate;
tert-butyl 2-[(5-isopropyl-1,3-thiazol-2-yl)amino]-2-oxoethylcarbamate;

tert-butyl (1S)-5-amino-1-{[(5-isopropyl-1,3-thiazol-2-yl)amino]carbonyl}pentylcarbamate;

tert-butyl 4-[(imino {[(4-methylphenyl)sulfonyl]amino}methyl)amino]-1-{[(5-isopropyl-1,3-thiazol-2-yl)amino]carbonyl}butylcarbamate;

tert-butyl 1-{[(5-isopropyl-1,3-thiazol-2-yl)amino]carbonyl}-3-(tritylamino)propylcarbamate; tert-butyl (1S)-1-(benzyloxymethyl)-2-[(5-isopropyl-1,3-thiazol-2-yl)amino]-2-oxoethylcarbamate;

tert-butyl (1S)-1-benzyl-2-[(5-isopropyl-1,3-thiazol-2-yl)amino]-2-oxoethylcarbamate;

tert-butyl (1R)-2-[(5-isopropyl-1,3-thiazol-2-yl)amino]-2-oxo-1-(benzylthiomethyl)ethylcarbamate;

benzyl (3S)-3-[(tert-butoxycarbonyl)amino]-4-[(5-isopropyl-1,3-thiazol-2-yl)amino]-4-oxobutanoate;

tert-butyl (2S)-2-{[(5-isopropyl-1,3-thiazol-2-yl)amino]carbonyl)-1-pyrrolidinecarboxylate;

tert-butyl (1S)-1-(1H-indol-3-ylmethyl)-2-[(5-isopropyl-1,3-thiazol-2-yl)amino]-2-oxoethylcarbamate;

tert-butyl (1S)-1-{[(5-isopropyl-1,3-thiazol-2-yl)amino]carbonyl)-3-(methylsulfanyl)propylcarbamate;

tert-butyl (1S)-2-benzyloxy-1-{[(5-isopropyl-1,3-thiazol-2-yl)amino]carbonyl)propylcarbamate;

tert-butyl (1S)-1-(4-benzyloxybenzyl)-2-[(5-isopropyl-1,3-thiazol-2-yl)amino]-2-oxoethylcarbamate;

tert-butyl (1S)-1-{[(5-isopropyl-1,3-thiazol-2-yl)amino7Jcarbonyl)-2-methylpropytcarbamate;

tert-butyl (1S)-1-{[(5-isopropyl-1,3-thiazol-2-.yl)amino]carbonyl)-3-methylbutylcarbamate and;

benzyl (4S)-4-[(tert-butoxycarbonyl)amino]-5-[(5-isopropyl-1,3-thiazol-2-yl)amino]-5-oxopentanoate;

and the pharmaceutically acceptable salts thereof.

7. A compound of formula (I) according to claim 1, wherein $R_1$ is optionally substituted in any of the free positions by one or more groups selected from the group consisting of halogen, nitro, oxo groups (=O), carboxy, cyano, alkyl, perfluorinated alkyl, alkenyl, alkynyl, cycloalkyl, aryl, heterocycyl, amino groups and derivatives thereof, carbonylamino groups and derivatives thereof, oxygen-substituted oximes, hydroxy group and derivatives thereof, carbonyl groups and derivatives thereof and sulfonated derivatives.

8. A compound of formula (I) according to claim 7, wherein said derivatives of amino groups are alkylamino, alkoxycarbonylalkylamino, dialkylamino, arylamino, diarylamino or aryleurido.

9. A compound of formula (I) according to claim 7, wherein said derivatives of carbonylamino groups are hydrogencarbonylamino (HCONH—), alkylcarbonylamino, alkenylcarbonyl amino, alkenylcarbonylamino, arylcarbonylamino or alkoxycarbonylamino.

10. A compound of formula (I) according to claim 7, wherein said oxygensubstituted oximes are alkoxycarbonylalkoxyimino or alkoxyimino.

11. A compound of formula (I) according to claim 7, wherein said derivatives of hydrocy groups are alkoxy, alkylcarbonyloxy, arylcarbonyloxy or cycloalkenyloxy.

12. A compound of formula (I) according to claim 7, wherein said derivatives of carbonly groups are alkylcarbonyl, arylcarbonyl, alkoxycarbonyl, aryloxycarbonyl cycloalkyloxycarbonyl, alkylaminocarbonyl or dialkylaminocarbonyl.

13. A compound of formula (I) according to claim 1, wherein said sulfonated derivatives are alkylthio, arylthio, alkylsulphonyl, arylsulphonyl, alkylsulphinyl, arylsulphinyl, arylsulphonyloxy, aminosulfonyl, alkylaminosulphonyl or dialkylaminosulphonyl.

\* \* \* \* \*